US012123006B2

(12) United States Patent
Liu et al.

(10) Patent No.: US 12,123,006 B2
(45) Date of Patent: Oct. 22, 2024

(54) BASE EDITING TOOL AND USE THEREOF

(71) Applicant: SHANGHAITECH UNIVERSITY, Shanghai (CN)

(72) Inventors: Yajing Liu, Shanghai (CN); Shisheng Huang, Shanghai (CN); Xingxu Huang, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 157 days.

(21) Appl. No.: 17/323,603

(22) Filed: May 18, 2021

(65) Prior Publication Data

US 2022/0372497 A1 Nov. 24, 2022

(51) Int. Cl.
*C12N 15/62* (2006.01)
*C07K 14/775* (2006.01)
*C12N 9/22* (2006.01)

(52) U.S. Cl.
CPC .......... *C12N 15/625* (2013.01); *C07K 14/775* (2013.01); *C12N 9/22* (2013.01); *C07K 2319/09* (2013.01)

(58) Field of Classification Search
CPC ...... C12N 15/625; C12N 9/22; C07K 14/775; C07K 2319/09; C07K 2319/00
See application file for complete search history.

(56) References Cited

U.S. PATENT DOCUMENTS

| | | | | |
|---|---|---|---|---|
| 10,167,457 | B2 * | 1/2019 | Liu | A61P 21/02 |
| 2017/0121693 | A1 * | 5/2017 | Liu | A61P 13/02 |
| 2018/0127780 | A1 * | 5/2018 | Liu | C12N 7/00 |
| 2020/0172885 | A1 * | 6/2020 | Joung | C12N 15/102 |
| 2020/0190493 | A1 * | 6/2020 | Liu | A61K 38/43 |
| 2021/0017506 | A1 * | 1/2021 | Guffy | C12N 15/907 |

FOREIGN PATENT DOCUMENTS

| | | | | |
|---|---|---|---|---|
| WO | WO-2018165629 A1 * | 9/2018 | | C07K 14/47 |
| WO | WO-2018176009 A1 * | 9/2018 | | C12N 15/102 |
| WO | WO-2020156575 A1 * | 8/2020 | | C12N 15/102 |

OTHER PUBLICATIONS

Tufts, CRISPR/Cas9, 2019, retrieved from: https://sites.tufts.edu/crispr/genome-editing/nickases/ (Year: 2019).*

Liu et al., A Cas-embedding strategy for minimizing off-target effects of DNA base editors, Nov. 2020, Nature Communications, vol. 11, pp. 1-9 (Year: 2020).*

Eid et al., CRISPR base editors: genome editing without double-stranded breaks, 2018, Biochemical Journal, vol. 475, pp. 1955-1964 (Year: 2018).*

Hodel et al., Dissection of a Nuclear Localization Signal, 2001, The Journal of Biological Chemistry, vol. 276, No. 2, pp. 1317-1325 (Year: 2001).*

Zong et al., Efficient C-to-T base editing in plants using a fusion of nCas9 and human APOBEC3A, 2018, Nature Biotechnology, vol. 36, No. 10, pp. 950-954 (Year: 2018).*

Luo et al., CRISPR/Cas9-deaminase enables robust base editing in Rhodobacter sphaeroides 2.4.1., 2020, Microbial Cell Factories, vol. 19, Issue 93, pp. 1-14 (Year: 2020).*

Li et al., Docking sites inside Cas9 for adenine base editing diversification and RNA off-target elimination, 2020, Nature Communications, vol. 11, pp. 1-11) (Year: 2020).*

* cited by examiner

*Primary Examiner* — Jeffrey Stucker
*Assistant Examiner* — Brittney E Donoghue
(74) *Attorney, Agent, or Firm* — Harness, Dickey & Pierce, P.L.C.

(57) ABSTRACT

The present disclosure relates to the field of biotechnology, in particular to a base editing tool and use thereof. The present disclosure provides a fusion protein comprising a first nCas9 fragment, a chimeric insertion fragment, a second nCas9 fragment and two UGI fragments from N-terminus to C-terminus, wherein the chimeric insertion fragment is selected from APOBEC1 fragment or APOBEC3A fragment. The present disclosure provides a novel base editing tool that is compatible with insertion of various deaminases on the chimeric sites of nCas9. Compared with nCas9 terminal fusion base editor, the base editing tool of the present invention significantly reduce of off-targeting on both DNA and RNA, while maintaining specific targeted base editing efficiency, with higher specificity and favorable industrialization prospects.

17 Claims, 8 Drawing Sheets

Specification includes a Sequence Listing.

BASE EDITING TOOL AND USE THEREOF

REFERENCE TO A SEQUENCE LISTING

This application contains references to amino acid sequences and/or nucleic acid sequences that are included in a Sequence Listing. The Sequence Listing, which is included in the content of the ASCII text file named "17424-000087-US Sequence Listing.txt" which is 374,248 bytes in size and was created on Mar. 22, 2024 and included herewith is incorporated herein by reference in its entirety.

FIELD

The present disclosure relates to the field of biotechnology, in particular to a base editing tool and use thereof.

BACKGROUND

Since CRISPR/Cas9 was published in 2013 for its application in gene editing in eukaryotic cells, gene editing technology based on CRISPR/Cas9 system has been greatly developed. This system merely consists of two parts: a guide RNA (gRNA) responsible for locating the target site sequence, and a Cas9 protein as an endonuclease. The combination of two parts can cleave target sites of interest with high efficacy and specificity, resulting in DNA double-strain break (DSB), which allows people to use non-homologous end joining (NHEJ) pathway of the cell itself to produce DNA fragment deletions or induce frameshift mutation, thereby resulting in gene knock-out. People can also use homology directed repair (HDR) pathway of a cell to perform precise substitution or knock-in of DNA fragment at target sites.

With the gradual deepening of research on CRISPR system, researchers have discovered that there are various problems with the gene editing based on DSBs. Firstly, the product of editing is uncontrollable. The repair product of NHEJ pathway at DSB sites on cellular DNA is random, sometimes only very small fragments are lost and no frameshift mutation is caused. Therefore, although DSBs can be produced, high knockout efficiency cannot be guaranteed. Secondly, the editing efficiency based on HDR repair pathway is always low, which is difficult to achieve high efficiency of gene editing in vivo. Finally, the off-target effects of CRISPR/Cas9 system can also result in irreversible sequence alteration on other sites in genome during editing process. The vast majority of human genetic diseases are caused by single base mutation. Therefore, the development of technologies that can edit single base precisely to address the above issues would be of great benefits to basic research and clinical disease treatment.

In 2017, a Cas9-based single base editing (BE) tool was reported in Nature by David R Liu's lab at Harvard. This system utilizes the fusion of nCas9, APOBEC1 and UGI to efficiently achieve targeted single base editing from cytosine (C) to thymine (T). The single base editing technology has attracted wide attention and application once published, and researchers have achieved efficient editing in different cell lines as well as in plants and animals.

With the wide application of cleavage editing technology, researchers have been developing an off-target detection technology with higher precision and sensitivity, for detecting BE with more strict requirements. In 2019, Yang Hui's lab and Gao Caixia's lab independently reported the gRNA-independent DNA off-target produced by CBE in *Science* respectively. In cultured cell line, the random off-target produced in each cell is different, and the off-target sites will be diluted in a cell population, making them undetectable. Yang Hui's team has developed a more sensitive unbiased off-target assay, GOTI, to detect the off-target effects of BE3. The method amplifies off-target sites by using mouse embryonic development cleverly, thus facilitating detection. Considering that the random off-targets on DNA are unpredictable and irreversible, this off-target phenomenon attracts public worry about the future of CBE in clinical therapeutic application. In the same year, Keith Joung's lab and Yang Hui's lab reported in Nature that CBE is severely off-target on the transcriptome, and BE3 can induce hundreds of gene mutations such as proto-oncogene and tumor suppressor genes, and may also result in other mutations that seriously harm health. Although RNAs in eukaryotic cells will not be inherited, theoretically all RNAs will involve in the regulations of cellular functions directly or by expressing proteins. Therefore, the production of off-target mutations also has a direct impact on cells.

The off-target editing of BE on RNA can be partially eliminated by amino acid mutation of deaminase. However, this method cannot guarantee success completely, for elimination of off-target editing may be accompanied by loss of efficiency on target editing. In addition, de novo evolution and verification are required for each deaminase, thus the workload of this method is great. Moreover, the random off-targeting caused by BE3 on DNA remains a problem. Therefore, it is urgent to develop a general, convenient and cost-effective evolutionary technology or strategy to reduce RNA or DNA off-targeting caused by BE3.

SUMMARY

Considering the shortcomings described in prior art, the object of the present disclosure is to provide a base editing tool and use thereof, to solve the problems in the prior art.

In order to achieve the above-mentioned and other related objects, one aspect of the present disclosure is to provide a fusion protein comprising a first nCas9 fragment, a chimeric insertion fragment, a second nCas9 fragment and two UGI fragments from N-terminus to C-terminus, wherein the chimeric insertion fragment is selected from an APOBEC1 fragment or an APOBEC3A fragment.

In some embodiments of the present disclosure, the first nCas9 fragment has an amino acid sequence comprising:

a) an amino acid sequence of SEQ ID NO: 1; or, b) an amino acid sequence having at least 80% sequence identity to SEQ ID NO: 1 and retaining the function of the amino acid sequence defined in a), preferably retaining on-target activity of nCas9;

and/or, the second nCas9 fragment has an amino acid sequence comprising:

c) an amino acid sequence of SEQ ID NO: 2; or, d) an amino acid sequence having at least 80% sequence identity to SEQ ID NO: 2 and retaining the function of the amino acid sequence defined in c), preferably retaining nCas9 on-target activity.

In some embodiments of the present disclosure, the APOBEC1 fragment has an amino acid sequence comprising:

e) an amino acid sequence of SEQ ID NO: 3; or, f) an amino acid sequence having at least 80% sequence identity to SEQ ID NO: 3 and retaining the function of the amino acid sequence defined in e), preferably retaining cytosine deaminase activity.

In some embodiments of the present disclosure, the APOBEC3A fragment has an amino acid sequence comprising:

i) an amino acid sequence of SEQ ID NO: 4; or, j) an amino acid sequence having at least 80% sequence identity to SEQ ID NO: 4 and retaining the function of the amino acid sequence defined in i), preferably retaining cytosine deaminase activity.

In some embodiments of the present disclosure, the UGI fragment has an amino acid sequence comprising:

k) an amino acid sequence of SEQ ID NO: 5; or, l) an amino acid sequence having at least 80% sequence identity to SEQ ID NO: 4 and retaining the function of the amino acid sequence defined in k), preferably retaining the activity of inhibiting the glycosylation of uracil DNA.

In some embodiments of the present disclosure, the fusion protein further comprises a nuclear localization signal fragment; preferably, the nuclear localization signal fragment comprises an amino acid sequence of SEQ ID NO: 6.

In some embodiments of the present disclosure, the fusion protein further comprises a flexible linker peptide fragment; preferably, the flexible linker peptide fragment comprises an amino acid sequence of SEQ ID NO: 7 or SEQ ID NO.8.

In some embodiments of the present disclosure, the fusion protein has an amino acid sequence as shown in SEQ ID NO: 9 or 10.

Another aspect of the present disclosure is to provide an isolated polynucleotide encoding the fusion protein described herein.

Another aspect of the present disclosure is to provide a construct comprising the isolated polynucleotide described above.

Another aspect of the present disclosure is to provide an expression system comprising the construct described above or having the polynucleotide described above integrated into its genome.

In some embodiments of the present disclosure, the host cell of the expression system is selected from eukaryotic cells or prokaryotic cells, preferably selected from mouse cells or human cells; more preferably selected from mouse brain neuroma cells, human embryonic kidney cells, human cervical cancer cells, human colon cancer cells, or human osteosarcoma cells; more preferably selected from N2a cells, HEK293FT cells, Hela cells, HCT116 cells or U20S cells.

Another aspect of the present disclosure is to provide a use of the fusion protein, the isolated polynucleotide, the construct or the expression system described above in gene editing.

In some embodiments of the present disclosure, the use is specifically a use in gene editing in eukaryotes.

Another aspect of the present disclosure is to provide a base editing system comprising the fusion protein described herein, wherein the base editing system further comprises sgRNA.

Another aspect of the present disclosure is to provide a method for gene editing comprising performing gene editing by the fusion protein described above, or the base editing system described above.

DETAILED DESCRIPTION

Figure 1:
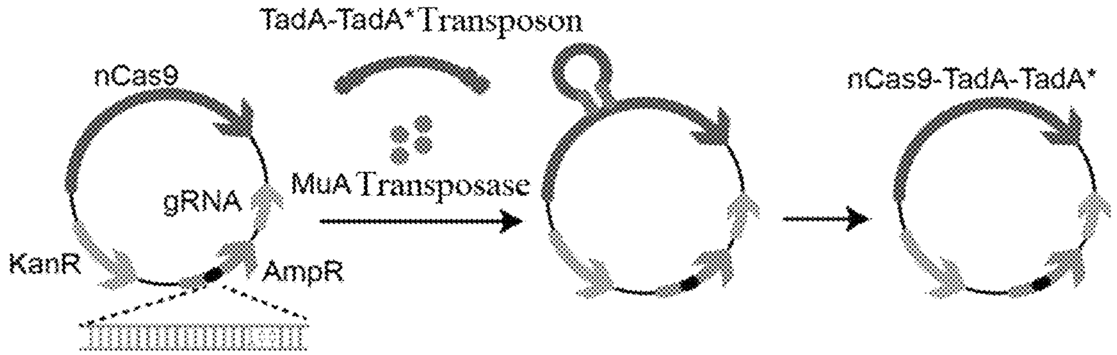
FIG. 1 is a schematic diagram of the present disclosure showing the construction of an nCas9 random insertion library based on Mu transposase.

After considerable exploratory research, the inventors of the present disclosure find that having a fusion functional fragment chimerized at proper locations within the nCas9 protein can extremely reduce the off-targeting caused by BE on both RNA and DNA at the same time, without affecting the on-target editing efficiency of BE, and on this basis, the present disclosure has been completed.

The first aspect of the present disclosure is to provide a fusion protein comprising a first nCas9 fragment, a chimeric insertion fragment, a second nCas9 fragment and two UGI fragments from N-terminus to C-terminus, and the chimeric insertion fragment is selected from an APOBEC1 fragment or an APOBEC3A fragment. The fusion protein substitutes 1048Thr-1063Ile of nCas9 (GenBank: MK048158.1) with a chimeric insertion fragment, and performs base editing at target sites in the guidance of sgRNA, which can extremely reduce the off-targeting caused by BE on RNA and DNA at the same time, without affecting the on-target editing efficiency of BE.

In the fusion protein provided by the present disclosure, the first nCas9 fragment may have an amino acid sequence comprising: a) an amino acid sequence of SEQ ID NO: 1; or, b) an amino acid sequence having at least 80% sequence identity to SEQ ID NO: 1 and retaining the function of the amino acid sequence defined in a). In particular, the amino acid sequence in b) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 1, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 1. For example, the first nCas9 fragment and the second nCas9 fragment still have the on-target activity of nCas9 after being combined, and specifically may have the activity of being able to target DNA under the guidance of a suitable gRNA. The amino acid sequence in b) may have at least 80%, 85%, 90%, 93%, 95%, 97% or 99% identity to SEQ ID NO: 1. Generally, the first nCas9 fragment is derived from *Streptococcus pyogenes*.

The term "sequence identity" in the present disclosure generally refers to the percentage of identical amino acid residues in sequences which may be aligned for purposes of comparison, and the identity of two or more target sequences can be calculated by calculation software known in the art, e.g., a software from NCBI.

In the fusion protein provided by the present disclosure, the second nCas9 fragment may have an amino acid sequence comprising: c) an amino acid sequence of SEQ ID NO: 2; or, d) an amino acid sequence having at least 80% sequence identity to SEQ ID NO: 2 and retaining the function of the amino acid sequence defined in c). In particular, the amino acid sequence in d) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 2, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 2. For example, the first nCas9 fragment and the second nCas9 fragment still have the on-target activity of nCas9 after being combined, and specifically may have the activity of being able to target DNA under the guidance of a suitable gRNA. The amino acid sequence in d) may have at least 80%, 85%, 90%, 93%, 95%, 97% or 99% identity to SEQ ID NO: 2. Generally, the second nCas9 fragment is derived from *E. coli* (*Streptococcus pyogenes*).

In the fusion protein provided by the present disclosure, the APOBEC1 fragment may have an amino acid sequence comprising: e) an amino acid sequence of SEQ ID NO: 3; or, f) an amino acid sequence having at least 80% sequence identity to SEQ ID NO: 3 and retaining the function of the amino acid sequence defined in e). In particular, the amino acid sequence in d) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 3, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 3. For example, the APOBEC1 fragment may have cytosine deaminase activity, and specifically may have the function of deaminating cytosine (C) to uracil (U). The amino acid sequence in f) may have at least 80%, 85%, 90%, 93%, 95%, 97% or 99% identity to SEQ ID NO: 3. Generally, the APOBEC1 fragment is derived from rat.

In the fusion protein provided by the present disclosure, the APOBEC3A fragment may have an amino acid sequence comprising: g) an amino acid sequence of SEQ ID NO: 4; or, h) an amino acid sequence having at least 80% sequence identity to SEQ ID NO: 4 and retaining the function of the amino acid sequence defined in g). In particular, the amino acid sequence in the h) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 4, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 4. For example, the APOBEC3A may have cytosine deaminase activity, and specifically may have the function of deaminating cytosine (C) to uracil (U). The amino acid sequence in h) has at least 80%, 85%, 90%, 93%, 95%, 97% or 99% identity to SEQ ID NO: 4. Generally, the APOBEC3A fragment is derived from human.

The fusion protein provided by the present disclosure may comprise two independent UGI fragments. The two UGI fragments may each independently have an amino acid sequence comprising: i) an amino acid sequence of SEQ ID NO: 5; or, j) an amino acid sequence having at least 80% sequence identity to SEQ ID NO: 5 and retaining the function of the amino acid sequence defined in i). In particular, the amino acid sequence in the j) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 5, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 5. For example, the two UGI fragments may have the activity of inhibiting glycosylation of uracil DNA. The amino acid sequence in j) may have at least 80%, 85%, 90%, 93%, 95%, 97% or 99% identity to SEQ ID NO: 5. Generally, the UGI fragments are derived from *Bacillus subtilis* bacteriophage.

In the fusion protein provided by the present disclosure, the substitution, deletion or addition can be the substitution of conservative amino acid. The "substitution of conservative amino acid" refers to the substitution of an amino acid residue by another amino acid residue having a similar side chain. Families of amino acid residues having similar side chains have been known to person skilled in the art, e.g. including but not limited to basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan) isoleucine), and aromatic side chains (e.g., tyrosine, phenylalanine, tryptophan, histidine). Non-limiting specific cases of conservative amino acid substitutions are provided in the Table below. The numbers in Table 1 (Amino Acid Similarity Matrix) indicate the similarity between two amino acids, when the number is 0 or higher, it is considered a conservative amino acid substitution, and Table 2 shows a scheme of exemplary conservative amino acid substitution.

TABLE 1

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE 2

| Amino Acid | Conservative substitution |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, He, D-Ile, Met, D-Met |

The fusion protein provided by the present disclosure may further comprise a nuclear localization signal fragment (BPNLS fragment), and the nuclear localization signal fragment generally can interact with nuclear import carrier, so that the protein can be transported into nucleus. The nuclear localization signal fragment can be located at the N-terminus of the first nCas9 fragment, and at the C-terminus of the second UGI fragment of the two UGI fragments, i.e., there is a BPNLS fragment at each end of the intact fusion protein. The BPNLS fragment can comprise an amino acid sequence of SEQ ID NO: 6.

The fusion protein provided by the present disclosure may further comprise a flexible linker peptide fragment. The flexible linker peptide fragment is generally a kind of flexible, linear and bendable amino acid fragment, which generally make a certain activity space between two proteins linked. For example, the flexible linker peptide fragment can be an XTEN peptide fragment, etc. The flexible linker peptide fragment (e.g., XTEN peptide fragment) can be located between the first nCas9 fragment and the chimeric fragment (ABOBEC1 or APOBEC3A), or between the chimeric fragment (ABOBEC1 or APOBEC3A) and the second nCas9 fragment. The XTEN peptide fragment can comprise an amino acid sequence of SEQ ID NO: 7. Another example of the flexible linker peptide fragment can be a GS peptide fragment, etc. The flexible linker peptide fragment (e.g., GS peptide fragment) can be located between the second nCas9 fragment and the first UGI of the two UGI fragments, or between the two UGI fragments. The flexible linker peptide fragment can comprise an amino acid sequence of SEQ ID NO: 8.

The fusion protein provided by the present disclosure can comprise a BPNLS peptide fragment, a first nCas9 fragment, a XTEN peptide fragment, APOBEC1, XTEN peptide fragment, a second nCas9 fragment, a GS peptide fragment and two UGI fragments from N-terminus to C-terminus. In a specific example of the present disclosure, the fusion protein can comprise a BPNLS peptide fragment, a first nCas9 fragment, a XTEN peptide fragment, APOBEC1, a XTEN peptide fragment, a second nCas9 fragment, a GS peptide fragment and two UGI fragments from N-terminus to C-terminus, and the fusion protein has an amino acid sequence of SEQ ID NO: 9.

The fusion protein provided by the present disclosure can comprise a BPNLS peptide fragment, a first nCas9 fragment, a XTEN peptide fragment, APOBEC3A, a XTEN peptide fragment, a second nCas9 fragment, a GS peptide fragment and two UGI fragments from N-terminus to C-terminus. In a specific example of the present disclosure, the fusion protein can comprise a BPNLS peptide fragment, a first nCas9 fragment, a XTEN peptide fragment, APOBEC3A, a XTEN peptide fragment, a second nCas9 fragment, a GS peptide fragment and two UGI fragments from N-terminus to C-terminus, and the fusion protein has an amino acid sequence of SEQ ID NO: 10.

The second aspect of the present disclosure is to provide an isolated polynucleotide encoding the fusion protein as provided by the first aspect of the present disclosure.

The third aspect of the present disclosure is to provide a construct containing the isolated polynucleotide as provided in the second aspect of the present disclosure. The construct can generally be obtained by inserting the isolated polynucleotide into proper expression vectors, and person skilled in the art can select proper expression vectors, e.g., the expression vector can include, but not limited to, pCMV expression vector, pSV2 expression vector, etc.

The fourth aspect of the present disclosure is to provide an expression system comprising the construct provided in the third aspect of the present disclosure or having the polynucleotide provided in the second aspect of the present disclosure integrated into its genome. The expression system can be a host cell expressing the fusion protein mentioned above, and the fusion protein can cooperate with sgRNA so that the fusion protein can be localized to target region, and base editing of the target region can be realized. In another specific example, the host cells can be eukaryotic cells and/or prokaryotic cells, specifically cells from mice or human; more specifically mouse brain neuroma cells, human embryonic kidney cells, human cervical cancer cells, human colon cancer cells, or human osteosarcoma cells, etc.; more specifically N2a cells, HEK293FT cells, Hela cells, HCT116 cells or U20S cells.

The fifth aspect of the present disclosure is to provide a use of the fusion protein as provided in the first aspect of the present disclosure, the isolated polynucleotide as provided in the second aspect of the present disclosure, the construct as provided in the third aspect of the present disclosure, or the expression system as provided in the fourth aspect of the present disclosure in gene editing, preferably a use in gene editing in eukaryotes; the eukaryotes can specifically be metazoa, specifically including but not limited to human, mice, etc. The use can specifically include, but not limited to, C-to-T base editing-, etc. These base editing can be applied to edit splice acceptor/donor sites to regulate RNA splicing, or applied in model (e.g. disease model, cell model, animal model, etc.) construction or in treatment of human diseases, etc. In one specific example of the present disclosure, the edited object can be an embryo, a cell, etc.

The sixth aspect of the present disclosure is to provide a base editing system comprising the fusion protein as provided in the first aspect of the present disclosure, wherein the base editing system further comprises sgRNA. A person skilled in the art can choose appropriate sgRNA targeting specific sites according to target editing region of a gene. For example, the sequence of a sgRNA can generally be at least partially complementary to the target region, and thereby can cooperate with the fusion protein, so that the fusion protein can be localized to target region to realize base editing in target region, e.g., it can be a cytosine deaminase reaction in which cytosine (C) is deaminated to thymine (T).

The seventh aspect of the present disclosure is to provide a method for base editing comprising: performing gene editing by the fusion protein as provided in the first aspect of the present disclosure, or the base editing system as provided in the sixth aspect of the present disclosure. For example, the method for base editing can comprise: culturing the expression system provided in the fourth aspect of the present disclosure under appropriate conditions, thus expressing the fusion protein, and the fusion protein can perform base editing on target region in the presence of sgRNA which cooperated with the fusion protein and targeting target region. The method for providing the presence of the sgRNA is known to a person skilled in the art, e.g., it can be culturing an expression system which can express the sgRNA under appropriate conditions, and the expression system can include a host cell containing the expression vector comprising the polynucleotide encoding the sgRNA, or a host cell having the polynucleotide encoding the sgRNA integrated into its genome. In one specific example of the present disclosure, the sgRNA and the fusion protein can be expressed in the same host cell, and the host cell can be a target cell. In another specific example of the present disclosure, the gene editing is gene editing in vitro.

The present disclosure provides a novel base editing tool, which can be compatible with insertion of various deaminases by the chimeric sites on nCas9. The tool shows significant decrease in off-target cases on DNA and RNA compared with nCas9 terminus fusion base editor while maintaining specific target base editing efficiency, which has higher specificity and good industrialization prospect.

The following specific examples illustrate the embodiments of the present disclosure, and a person skilled in the art can easily understand other advantages and effects of the present disclosure according to the content disclosed in the present specification. The present disclosure can also be carried out or applied by other different specific embodiments, and various details in the present specification can be based on different opinions and applications, and various modifications or changes can be made without departing from the spirit of the present disclosure.

Before further describing the specific embodiments of the present disclosure, it can be understood that the protection scope of the present disclosure is not limited to the following specific particular embodiments; it can also be understood that the terms used in the embodiments of the present disclosure are used for describing the specific particular embodiments, rather than limiting the scope of protection of the present disclosure. In the specification and claims of the present disclosure, unless specified otherwise in the content, the term "a", "an" or "this" in singular form cover the plural form thereof.

When numerical ranges are given in the embodiments, it can be understood that the two endpoints of each numerical range and any value between the two endpoints can be selected, unless specified otherwise in the present disclosure. Unless defined otherwise, all technical and scientific terms used in the present disclosure have the same meanings commonly understood by those of skill in the art. In addition to the specific methods, devices, and materials used in the embodiments, according to the knowledge in the prior art and the description of the present disclosure, those of skill in the art can also use any prior art methods, devices, and materials which are similar or equal to the methods, devices, and materials described in the embodiments of the present disclosure to realize the present disclosure.

Unless specified otherwise, the experimental methods, detection methods, and preparation methods disclosed in the present disclosure all use conventional molecular biological, biochemical, chromatin structure and analysis, analytical chemical, cell culture, and recombinant DNA technology in the art, and other conventional technology in related fields. The technologies have been completely described in existing documents. For details, please refer to: Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed) Humana Press, Totowa, 1999, etc.

Example 1

1. Construction of TadA-TadA* Transposon Based on MuA Transposase

The sequence of TadA-TadA* transposon (SEQ ID NO: 11) was synthesized by Shanghai Biosune Biotechnology Co., Ltd., and amplified by PCR using high-fidelity enzyme kit (Vazyme, P501-d2). The forward primer was: GGTCTCTGATCCGGCGCACGAA (SEQ ID NO: 71); the reverse primer was: GGTCTCTGATCCGGCGCACGAA (SEQ ID NO: 72);

The amplification system used is as follows:

TABLE 3

| | |
|---|---|
| Water | Add water to 20 µL |
| 2× buffer | 5 µL |
| dNTP | 1 µL |
| Forward primer (10 µM) | 2 µL |
| Reverse primer (10 µM) | 2 µL |
| Synthesized template of TadA-TadA* transposon | 1 ng |
| High-fidelity enzyme | 1 µL |

The PCR procedure used are as follows:

TABLE 4

| | | |
|---|---|---|
| 1 cycle | 98° C. | 3 min |
| 35 cycle | 95° C. | 20 s |
| | 68° C. | 30 s |
| | 72° C. | set with (an extension of) 30 s/kb |
| 1 cycle | 72° C. | 5 min |
| 1 cycle | 4° C. | ∞ |

The PCR amplification product was purified and recovered by AxyPrep PCR Clean-up kit (Axygen, AP-PCR-500G) for later use.

2. Construction of sgRNA

The sgRNA used in detecting on-target editing efficiency of ABE (Adenine base editing) in eukaryote was ABE-site1. The sgRNAs used for subsequent detection of ABE and CE-ABE (centrally encapsulate ABE) at eight endogenous loci in HEK293T cells were site 2-site 9. The sgRNAs used for subsequent detection of ABE and CE-ABE at twelve endogenous loci in N2a cells were site10-site 21. The sequences of the loci are of SEQ ID NO: 12-32. The sgRNAs used in detecting CE-CBE and CE-A3A, namely site 22-site 32, are all endogenous gene loci in targeting HEK293T cells. The sequences of the loci are of SEQ ID NO: 57-67. The forward primers and reverse primers with 20 bases complementarily paired to target site sequences, and dissolve them to 100 µM with sterile water. The primers were ligated to a pGL3-U6-sgRNA (Addgene #51133) vector after annealing to construct target specific sgRNAs.

The annealing system used is as follows:

TABLE 5

| | |
|---|---|
| Forward primer | 4.5 µL |
| Reverse primer | 4.5 µL |
| 10× NEB buffer2 | 1 µL |

The annealing procedure used is as follows:

TABLE 6

| | |
|---|---|
| 95° C. | 5 min |
| 95-85° C. | −2° C./s |
| 85-25° C. | −0.1° C./s |
| 4° C. | ∞ |

The pGL3-U6-sgRNA (Addgene #51133) plasmid was digested with BsaI (NEB, R0535S) to obtain a linearized sgRNA vector. The enzymatic digestion system used is as follows:

TABLE 7

| | |
|---|---|
| Water | Add water to 50 µL |
| PGL3-U6 plasmid | 10 µg |
| 10× cutsmart buffer | 5 µL |
| BsaI Enzyme | 5 µL |

The above reaction system was prepared, and then subjected to reaction for 5 h at 37° C., the digested product was subjected to gel recovery with AxyPrep DNA gel recovery kit (Axygen, AP-GX-250G) to obtain a linearized vector. 50 ng of the linearized vector was ligated to 3 µL of the annealing product with T4 ligase (NEB, M0202S), and incubated for 2 h at 16° C., after transformation and plating, and correct target-specific sgRNA was verified by Sanger sequencing. The ligation system was as follows:

TABLE 8

| | |
|---|---|
| Water | Add water to 10 µL |
| Linear fragment of PGL3-U6-BsaI digestion | 20 ng |
| Annealing product | 1 µL |
| Solution I | 5 µL |

The ligation product was subjected to transfection subsequently, and recovered for 30 min, then plated on a LB agar plate with ampicillin resistance and incubated overnight at 37° C. Single clones were selected and sequenced to validate the sgRNA site1-site21 used for the detection of ABE.

3. Construction of a Recipient Plasmid for Random Insertion of MuA Transposase

The primers used for plasmid construction were all synthesized by Shanghai Biosune Biotechnology Co., Ltd.

Firstly, the pCMV-ABEmax (Addgene, #112095) plasmid was used as a template, with the forward primer: GACAAGAAGTACAGCATCGGCC (SEQ ID NO: 73); and the reverse primer: GCTGTACTTCTTGT-CACTGCTGACTTTCCGCTTCTTC (SEQ ID NO: 74) to obtain a fragment of 7629 bp in length. The PCR amplification product was purified and recovered by AxyPrep PCR Clean-up kit (Axygen, AP-PCR-500G), and the fragment was subjected to recombination with Gibson Assembly Master Mix recombinant kit (NEB, E2611S). The reaction system used is as follows:

TABLE 9

| | |
|---|---|
| Gibson Assembly Master Mix (2×) | 5 µL |
| 7629 bp PCR fragment | 200 ng |
| Sterile water | Add water to 10 µL |

The reaction solutions were mixed and incubated for 1 h at 50° C., subjected to transfection subsequently, recovered for 30 min, and plated on a LB agar plate with ampicillin resistance, incubated overnight at 37° C. Single clones were selected for verification by sequencing to obtain a pCMV-nCas9 plasmid (SEQ ID NO: 33). The successfully constructed plasmid (SEQ ID NO: 33) was subjected to plasmid extraction with AxyPrep plasmids miniprep kit (Axygen, AP-MN-P-250G).

SEQ ID NO: 33 was used as a template, the forward primer is:

GAAGAAGCGGAAAGTCGACAAGAAGTACAG-CATCGG (SEQ ID NO: 75), the reverse primer is: CTGAGCTAGCTGT-CAACGAGCCCCAGCTGGTTCTTT (SEQ ID NO: 76); PCR amplification was carried out to obtained a nCas9 fragment with length of 4507 bp;

The PET30 plasmid was used as a template, the forward primer is: CTCACTGATTAAGCAT-TGGTAAGCGCGGAACCCCTATTTGTT (SEQ ID NO: 77), the reverse primer is: CCGTTTCATGGTGG-CATGTATATCTCCTTCTTAAAGT-TAAACAAAATT (SEQ ID NO: 78); PCR amplification was carried out to obtained a KanR fragment with length of 4620 bp;

The pGL3-U6-sgRNA plasmid was used as a template, the forward primer was: GTATAATACTAGTGCTCTTGCCCGGCGT-CAATACGTTTTAGAGCTAGAAAT AGCAAGTT (SEQ ID NO: 79), the reverse primer is: gttagcagccg-gatcaaaaaaagcaccgactcgg (SEQ ID NO: 80); PCR amplification was carried out to obtain a U6-sgRNA fragment with length of 132 bp; Then the U6-sgRNA fragment was used as a template, the forward primer is: TTGACAGCTAGCTCAGTCCTAGGTATAATACTA GTGCTCTTGCC (SEQ ID NO: 81), the reverse primer is: GTTAGCAGCCGGAT-CAAAAAAAGCACCGACTCGG (SEQ ID NO: 82); PCR amplification was carried out to obtain a J23119promoter-gRNA fragment with length of 154 bp;

The pCMV-ABEmax (Addgene, #112095) plasmid was used as a template, the forward primer is: CTTTTCGGGGAAATGTGGGAAATGTGCGCG-GAACC (SEQ ID NO: 83), the reverse primer is: CCCGGCGTCAATACGGGATA (SEQ ID NO: 84); PCR amplification was carried out to obtain an AmpR-1 fragment with length of 386 bp;

The pCMV-ABEmax (Addgene, #112095) plasmid was used as a template, the forward primer is: GTAT-TGACGCCGGGTAAGAGCAACTCGGTCGCCGC (SEQ ID NO: 85), the reverse primer is: TTAC-CAATGCTTAATCAGTGAGGCACC (SEQ ID NO: 86); PCR amplification was carried out to obtain an AmpR-2 fragment with length of 620 bp.

The PCR above was all carried out with Vazyme high-fidelity enzyme kit (Vazyme, P501-d2), and the reaction system used is as follows:

TABLE 10

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Template | 1 ng |

The PCR procedure is used as follows:

TABLE 11

| | | |
|---|---|---|
| 1 cycle | 98° C. | 3 min |
| 35 cycle | 95° C. | 20 s |
| | 68° C. | 30 s |
| | 72° C. | set with (an extension of) 30 s/kb |
| 1 cycle | 72° C. | 5 min |
| 1 cycle | 4° C. | ∞ |

All the PCR amplification products above were purified and recovered by AxyPrep PCR Clean-up kit (Axygen, AP-PCR-500G), and the fragments were subjected to recombination with Gibson Assembly Master Mix recombinant kit (NEB, E2611S), and the reaction system used is as follows:

TABLE 12

| | |
|---|---|
| Gibson Assembly Master Mix (2×) | 10 μL |
| nCas9 fragment (4507 bp) | 80 ng |
| KanR fragment (4620 bp) | 80 ng |
| J23119 promoter-gRNA fragment (154 bp) | 10 ng |
| AmpR-1 fragment (386 bp) | 20 ng |
| AmpR-2 fragment (620 bp) | 30 ng |
| Sterile water | Add water to 20 μL |

The reaction solutions were mixed and incubated for 1 h at 50° C., subjected to transfection subsequently, recovered for 30 min, and plated on a LB agar plate with kanamycin resistance, incubated overnight at 37° C. Single clones were selected for sequencing verification to obtain a pET-nCas9-gRNA-AmpR (A118X)-KanR plasmid (SEQ ID NO: 34). The successfully constructed plasmid (SEQ ID NO: 34) was subjected to plasmid extraction with AxyPrep plasmids miniprep kit (Axygen, AP-MN-P-250G).

4. Construction of In Vitro Random Insertion Library

The fragment of TadA-TadA* transposon, pET-nCas9-gRNA-AmpR (A118X)-KanR plasmid (SEQ ID NO: 34) and MuA transposase (Thermo Fisher, F-701) obtained by PCR were reacted in vitro to form an insertion plasmid library having random insertion of the fragment of TadA-TadA* transposon in a plasmid, and the detailed process is shown in FIG. 1.

The detailed reaction system used is as follows:

TABLE 13

| | |
|---|---|
| TadA-TadA* fragment | 250 ng |
| SEQ34 plasmid | 500 ng |
| MuA transposase | 1 μL |
| 5× Reaction Buffer for MuA Transposase | 4 μL |
| Water | Add water to 20 μL |

The reaction solution was incubated for 1 h at 30° C. to achieve random insertion, then incubated for 10 min at 75° C. to inactivate MuA transposase. Then DNA was purified by precipitation with isopropanol, and resuspended in 5 μL of deionized water, and electro-transfected into 100 μL of BL21 (DE3) Electro (Shanghai Weidi Biotechnology, EE1002) competent cells. Then 1 mL of SOC medium was added, and the bacteria was cultured for 1 h at 37° C. The bacteria mentioned above was recovered for 1 h in SOC medium after transformation, followed by spreading on several LB agar plates containing 10 μg/mL of kanamycin, and incubating for 16 h at 37° C. Then the bacterial colonies were scraped from the plates, followed by plasmid extraction with AxyPrep plasmids miniprep kit (Axygen, AP-MN-P-250G). The extracted MuA random insertion plasmid library was sequenced by Novogene Bioinformation Institution (Beijing, China), using Illumina HiSeq X Ten (2×150PE) to sequence the constructed transposon library. Firstly, all data readers were mapped to the main chain sequence by BWA v0.7.16 with default parameters. Broken reads were extracted, followed by mapping to the insertion sequence. All mapped reads were checked, and the break-points were recorded as insert loci. The final random insertion of the insertion library was obtained, in particular, the insert loci on nCas9 was calculated in terms of the C-terminus of the amino acid (e.g., the insertion occurs at the 5th Aspartic acid at C-terminus, and this insert loci is 5). After statistics, it was found that the coverage rate of the random insertion library based on MuA is very high, at least one insertion was occurred at 99.99% of amino acid sites on nCas9, and the insertion frequency (F) and insert loci (L) was ordering from small to large as follows:

TABLE 14

| | | | | | | | | | | | | | | | |
|---|---|---|---|---|---|---|---|---|---|---|---|---|---|---|---|
| L | 202 | 234 | 255 | 281 | 382 | 393 | 429 | 559 | 625 | 639 | 750 | 793 | 887 | 955 | 965 |
| F | 0 | 0 | 0 | 0 | 0 | 0 | 0 | 0 | 0 | 0 | 0 | 0 | 0 | 0 | 0 |
| L | 1062 | 1192 | 1317 | 103 | 184 | 228 | 233 | 235 | 431 | 472 | 529 | 535 | 586 | 588 | 678 |
| F | 0 | 0 | 0 | 1 | 1 | 1 | 1 | 1 | 1 | 1 | 1 | 1 | 1 | 1 | 1 |
| L | 794 | 1055 | 1064 | 1157 | 1280 | 12 | 37 | 55 | 96 | 268 | 546 | 554 | 568 | 609 | 850 |
| F | 1 | 1 | 1 | 1 | 1 | 2 | 2 | 2 | 2 | 2 | 2 | 2 | 2 | 2 | 2 |
| L | 933 | 1136 | 1194 | 1208 | 1232 | 1324 | 15 | 67 | 248 | 262 | 291 | 337 | 460 | 574 | 662 |
| F | 2 | 2 | 2 | 2 | 2 | 2 | 3 | 3 | 3 | 3 | 3 | 3 | 3 | 3 | 3 |
| L | 708 | 718 | 781 | 928 | 935 | 1037 | 1060 | 1067 | 1347 | 58 | 78 | 224 | 396 | 428 | 481 |
| F | 3 | 3 | 3 | 3 | 3 | 3 | 3 | 3 | 3 | 4 | 4 | 4 | 4 | 4 | 4 |
| L | 497 | 636 | 650 | 661 | 668 | 680 | 695 | 726 | 729 | 730 | 763 | 826 | 846 | 1000 | 1007 |
| F | 4 | 4 | 4 | 4 | 4 | 4 | 4 | 4 | 4 | 4 | 4 | 4 | 4 | 4 | 4 |
| L | 1124 | 1216 | 163 | 289 | 332 | 349 | 487 | 527 | 563 | 664 | 733 | 791 | 798 | 835 | 911 |
| F | 4 | 4 | 5 | 5 | 5 | 5 | 5 | 5 | 5 | 5 | 5 | 5 | 5 | 5 | 5 |
| L | 941 | 1006 | 1054 | 1080 | 1149 | 1359 | 26 | 63 | 169 | 225 | 277 | 279 | 290 | 351 | 389 |
| F | 5 | 5 | 5 | 5 | 5 | 5 | 6 | 6 | 6 | 6 | 6 | 6 | 6 | 6 | 6 |
| L | 410 | 462 | 491 | 566 | 571 | 572 | 673 | 741 | 868 | 920 | 948 | 971 | 1058 | 1066 | 1089 |
| F | 6 | 6 | 6 | 6 | 6 | 6 | 6 | 6 | 6 | 6 | 6 | 6 | 6 | 6 | 6 |
| L | 1141 | 1173 | 1321 | 1362 | 194 | 226 | 286 | 288 | 356 | 371 | 455 | 492 | 530 | 570 | 633 |
| F | 6 | 6 | 6 | 6 | 7 | 7 | 7 | 7 | 7 | 7 | 7 | 7 | 7 | 7 | 7 |
| L | 666 | 701 | 704 | 724 | 862 | 907 | 973 | 1029 | 1078 | 1097 | 1176 | 1303 | 1323 | 1357 | 49 |
| F | 7 | 7 | 7 | 7 | 7 | 7 | 7 | 7 | 7 | 7 | 7 | 7 | 7 | 7 | 8 |
| L | 60 | 97 | 160 | 218 | 295 | 457 | 638 | 641 | 706 | 840 | 866 | 896 | 1045 | 1233 | 1290 |
| F | 8 | 8 | 8 | 8 | 8 | 8 | 8 | 8 | 8 | 8 | 8 | 8 | 8 | 8 | 8 |
| L | 20 | 40 | 122 | 141 | 155 | 206 | 221 | 253 | 296 | 329 | 415 | 424 | 439 | 542 | 548 |
| F | 9 | 9 | 9 | 9 | 9 | 9 | 9 | 9 | 9 | 9 | 9 | 9 | 9 | 9 | 9 |
| L | 600 | 618 | 696 | 768 | 777 | 854 | 857 | 892 | 918 | 999 | 1228 | 1256 | 1284 | 1298 | 1325 |
| F | 9 | 9 | 9 | 9 | 9 | 9 | 9 | 9 | 9 | 9 | 9 | 9 | 9 | 9 | 9 |
| L | 1364 | 153 | 254 | 287 | 314 | 342 | 391 | 828 | 869 | 886 | 990 | 1021 | 1101 | 1226 | 1244 |
| F | 9 | 10 | 10 | 10 | 10 | 10 | 10 | 10 | 10 | 10 | 10 | 10 | 10 | 10 | 10 |
| L | 1270 | 1272 | 1274 | 1286 | 1289 | 1318 | 172 | 176 | 250 | 273 | 350 | 358 | 377 | 536 | 557 |
| F | 10 | 10 | 10 | 10 | 10 | 10 | 11 | 11 | 11 | 11 | 11 | 11 | 11 | 11 | 11 |
| L | 610 | 674 | 746 | 762 | 770 | 788 | 848 | 861 | 906 | 934 | 953 | 32 | 101 | 128 | 212 |
| F | 11 | 11 | 11 | 11 | 11 | 11 | 11 | 11 | 11 | 11 | 11 | 12 | 12 | 12 | 12 |
| L | 310 | 340 | 495 | 499 | 510 | 621 | 627 | 648 | 651 | 681 | 789 | 899 | 905 | 949 | 1001 |
| F | 12 | 12 | 12 | 12 | 12 | 12 | 12 | 12 | 12 | 12 | 12 | 12 | 12 | 12 | 12 |
| L | 1031 | 1044 | 1172 | 1212 | 1240 | 1241 | 1257 | 11 | 31 | 237 | 246 | 258 | 297 | 526 | 539 |
| F | 12 | 12 | 12 | 12 | 12 | 12 | 12 | 13 | 13 | 13 | 13 | 13 | 13 | 13 | 13 |
| L | 573 | 580 | 604 | 753 | 878 | 891 | 1065 | 1238 | 1252 | 1326 | 1327 | 22 | 45 | 95 | 118 |
| F | 13 | 13 | 13 | 13 | 13 | 13 | 13 | 13 | 13 | 13 | 13 | 14 | 14 | 14 | 14 |
| L | 140 | 168 | 241 | 247 | 256 | 275 | 308 | 325 | 419 | 430 | 433 | 613 | 647 | 692 | 702 |
| F | 14 | 14 | 14 | 14 | 14 | 14 | 14 | 14 | 14 | 14 | 14 | 14 | 14 | 14 | 14 |
| L | 735 | 751 | 811 | 859 | 951 | 969 | 1015 | 1069 | 1119 | 1180 | 1191 | 1245 | 1319 | 1361 | 88 |
| F | 14 | 14 | 14 | 14 | 14 | 14 | 14 | 14 | 14 | 14 | 14 | 14 | 14 | 14 | 15 |
| L | 98 | 147 | 173 | 240 | 283 | 338 | 406 | 422 | 534 | 544 | 593 | 659 | 685 | 691 | 774 |
| F | 15 | 15 | 15 | 15 | 15 | 15 | 15 | 15 | 15 | 15 | 15 | 15 | 15 | 15 | 15 |
| L | 804 | 853 | 923 | 947 | 1014 | 1036 | 1177 | 1182 | 1224 | 1333 | 1345 | 1363 | 9 | 47 | 92 |
| F | 15 | 15 | 15 | 15 | 15 | 15 | 15 | 15 | 15 | 15 | 15 | 15 | 16 | 16 | 16 |
| L | 94 | 104 | 106 | 109 | 236 | 244 | 305 | 402 | 441 | 464 | 494 | 635 | 667 | 679 | 698 |
| F | 16 | 16 | 16 | 16 | 16 | 16 | 16 | 16 | 16 | 16 | 16 | 16 | 16 | 16 | 16 |
| L | 709 | 759 | 832 | 836 | 964 | 1009 | 1086 | 1087 | 1236 | 14 | 43 | 72 | 179 | 197 | 276 |
| F | 16 | 16 | 16 | 16 | 16 | 16 | 16 | 16 | 16 | 17 | 17 | 17 | 17 | 17 | 17 |
| L | 284 | 327 | 335 | 482 | 484 | 502 | 602 | 737 | 749 | 809 | 813 | 942 | 981 | 986 | 1046 |
| F | 17 | 17 | 17 | 17 | 17 | 17 | 17 | 17 | 17 | 17 | 17 | 17 | 17 | 17 | 17 |
| L | 1107 | 1151 | 1158 | 1190 | 1210 | 1243 | 1300 | 2 | 16 | 18 | 66 | 130 | 171 | 209 | 242 |
| F | 17 | 17 | 17 | 17 | 17 | 17 | 17 | 18 | 18 | 18 | 18 | 18 | 18 | 18 | 18 |
| L | 313 | 359 | 409 | 442 | 486 | 682 | 712 | 748 | 796 | 898 | 957 | 979 | 995 | 1134 | 1264 |
| F | 18 | 18 | 18 | 18 | 18 | 18 | 18 | 18 | 18 | 18 | 18 | 18 | 18 | 18 | 18 |
| L | 1366 | 24 | 52 | 56 | 71 | 162 | 229 | 293 | 298 | 369 | 414 | 470 | 500 | 504 | 676 |
| F | 18 | 19 | 19 | 19 | 19 | 19 | 19 | 19 | 19 | 19 | 19 | 19 | 19 | 19 | 19 |
| L | 677 | 874 | 888 | 925 | 961 | 1104 | 1126 | 1132 | 1188 | 1193 | 1329 | 1368 | 13 | 89 | 186 |
| F | 19 | 19 | 19 | 19 | 19 | 19 | 19 | 19 | 19 | 19 | 19 | 19 | 20 | 20 | 20 |
| L | 207 | 208 | 261 | 274 | 278 | 292 | 317 | 318 | 352 | 420 | 473 | 537 | 612 | 637 | 755 |
| F | 20 | 20 | 20 | 20 | 20 | 20 | 20 | 20 | 20 | 20 | 20 | 20 | 20 | 20 | 20 |
| L | 775 | 803 | 837 | 849 | 871 | 880 | 897 | 921 | 938 | 1049 | 1072 | 1111 | 1147 | 1171 | 1205 |
| F | 20 | 20 | 20 | 20 | 20 | 20 | 20 | 20 | 20 | 20 | 20 | 20 | 20 | 20 | 20 |
| L | 1213 | 1305 | 1367 | 178 | 195 | 213 | 220 | 243 | 263 | 270 | 363 | 461 | 478 | 547 | 619 |

TABLE 14-continued

| | | | | | | | | | | | | | | | |
|---|---|---|---|---|---|---|---|---|---|---|---|---|---|---|---|
| F | 20 | 20 | 20 | 21 | 21 | 21 | 21 | 21 | 21 | 21 | 21 | 21 | 21 | 21 | 21 |
| L | 645 | 683 | 783 | 858 | 867 | 875 | 963 | 993 | 998 | 1108 | 1343 | 3 | 59 | 112 | 174 |
| F | 21 | 21 | 21 | 21 | 21 | 21 | 21 | 21 | 21 | 21 | 21 | 22 | 22 | 22 | 22 |
| L | 196 | 198 | 239 | 339 | 421 | 444 | 513 | 543 | 551 | 587 | 594 | 611 | 687 | 760 | 844 |
| F | 22 | 22 | 22 | 22 | 22 | 22 | 22 | 22 | 22 | 22 | 22 | 22 | 22 | 22 | 22 |
| L | 913 | 985 | 992 | 1002 | 1076 | 1109 | 1123 | 1125 | 1153 | 1156 | 1184 | 1230 | 1291 | 143 | 177 |
| F | 22 | 22 | 22 | 22 | 22 | 22 | 22 | 22 | 22 | 22 | 22 | 22 | 22 | 23 | 23 |
| L | 187 | 271 | 323 | 334 | 368 | 468 | 516 | 552 | 556 | 584 | 711 | 715 | 806 | 927 | 1030 |
| F | 23 | 23 | 23 | 23 | 23 | 23 | 23 | 23 | 23 | 23 | 23 | 23 | 23 | 23 | 23 |
| L | 1130 | 1159 | 1282 | 1315 | 1320 | 75 | 85 | 125 | 211 | 227 | 265 | 266 | 282 | 285 | 294 |
| F | 23 | 23 | 23 | 23 | 23 | 24 | 24 | 24 | 24 | 24 | 24 | 24 | 24 | 24 | 24 |
| L | 304 | 331 | 398 | 407 | 427 | 459 | 479 | 560 | 576 | 595 | 656 | 671 | 870 | 902 | 936 |
| F | 24 | 24 | 24 | 24 | 24 | 24 | 24 | 24 | 24 | 24 | 24 | 24 | 24 | 24 | 24 |
| L | 1027 | 33 | 81 | 117 | 215 | 357 | 426 | 545 | 663 | 689 | 890 | 974 | 980 | 1034 | 1063 |
| F | 24 | 25 | 25 | 25 | 25 | 25 | 25 | 25 | 25 | 25 | 25 | 25 | 25 | 25 | 25 |
| L | 1081 | 1114 | 1122 | 1295 | 1322 | 1342 | 7 | 44 | 126 | 148 | 452 | 498 | 585 | 653 | 684 |
| F | 25 | 25 | 25 | 25 | 25 | 25 | 26 | 26 | 26 | 26 | 26 | 26 | 26 | 26 | 26 |
| L | 717 | 864 | 960 | 988 | 1071 | 1084 | 1185 | 1247 | 1294 | 1335 | 27 | 121 | 167 | 183 | 364 |
| F | 26 | 26 | 26 | 26 | 26 | 26 | 26 | 26 | 26 | 26 | 27 | 27 | 27 | 27 | 27 |
| L | 489 | 507 | 883 | 908 | 929 | 962 | 997 | 1079 | 1133 | 1148 | 1152 | 1206 | 1304 | 1341 | 1344 |
| F | 27 | 27 | 27 | 27 | 27 | 27 | 27 | 27 | 27 | 27 | 27 | 27 | 27 | 27 | 27 |
| L | 158 | 190 | 192 | 249 | 343 | 365 | 564 | 620 | 743 | 785 | 945 | 954 | 967 | 1047 | 1116 |
| F | 28 | 28 | 28 | 28 | 28 | 28 | 28 | 28 | 28 | 28 | 28 | 28 | 28 | 28 | 28 |
| L | 1117 | 1131 | 1195 | 1214 | 46 | 64 | 170 | 180 | 257 | 260 | 280 | 354 | 390 | 477 | 688 |
| F | 28 | 28 | 28 | 28 | 29 | 29 | 29 | 29 | 29 | 29 | 29 | 29 | 29 | 29 | 29 |
| L | 700 | 705 | 722 | 773 | 881 | 912 | 989 | 1056 | 1118 | 1203 | 1223 | 1253 | 21 | 25 | 135 |
| F | 29 | 29 | 29 | 29 | 29 | 29 | 29 | 29 | 29 | 29 | 29 | 29 | 30 | 30 | 30 |
| L | 149 | 152 | 175 | 383 | 404 | 418 | 569 | 623 | 742 | 771 | 830 | 860 | 1033 | 1189 | 6 |
| F | 30 | 30 | 30 | 30 | 30 | 30 | 30 | 30 | 30 | 30 | 30 | 30 | 30 | 30 | 31 |
| L | 69 | 150 | 193 | 264 | 437 | 480 | 512 | 643 | 744 | 761 | 847 | 885 | 904 | 922 | 1025 |
| F | 31 | 31 | 31 | 31 | 31 | 31 | 31 | 31 | 31 | 31 | 31 | 31 | 31 | 31 | 31 |
| L | 1074 | 5 | 205 | 219 | 222 | 223 | 272 | 385 | 397 | 423 | 454 | 517 | 626 | 675 | 690 |
| F | 31 | 32 | 32 | 32 | 32 | 32 | 32 | 32 | 32 | 32 | 32 | 32 | 32 | 32 | 32 |
| L | 728 | 855 | 956 | 1022 | 1094 | 1181 | 1225 | 1246 | 1269 | 1275 | 54 | 61 | 165 | 311 | 596 |
| F | 32 | 32 | 32 | 32 | 32 | 32 | 32 | 32 | 32 | 32 | 33 | 33 | 33 | 33 | 33 |
| L | 657 | 727 | 807 | 818 | 824 | 842 | 910 | 983 | 1251 | 4 | 34 | 111 | 251 | 321 | 330 |
| F | 33 | 33 | 33 | 33 | 33 | 33 | 33 | 33 | 33 | 34 | 34 | 34 | 34 | 34 | 34 |
| L | 367 | 408 | 603 | 831 | 991 | 1023 | 1106 | 1242 | 1268 | 99 | 132 | 299 | 326 | 384 | 405 |
| F | 34 | 34 | 34 | 34 | 34 | 34 | 34 | 34 | 34 | 35 | 35 | 35 | 35 | 35 | 35 |
| L | 425 | 467 | 508 | 528 | 605 | 716 | 786 | 808 | 1161 | 1365 | 90 | 105 | 376 | 447 | 501 |
| F | 35 | 35 | 35 | 35 | 35 | 35 | 35 | 35 | 35 | 35 | 36 | 36 | 36 | 36 | 36 |
| L | 632 | 738 | 745 | 970 | 1016 | 1073 | 1120 | 1121 | 1221 | 1261 | 1346 | 93 | 145 | 400 | 413 |
| F | 36 | 36 | 36 | 36 | 36 | 36 | 36 | 36 | 36 | 36 | 36 | 37 | 37 | 37 | 37 |
| L | 453 | 505 | 523 | 561 | 606 | 823 | 838 | 882 | 42 | 48 | 379 | 440 | 541 | 601 | 740 |
| F | 37 | 37 | 37 | 37 | 37 | 37 | 37 | 37 | 38 | 38 | 38 | 38 | 38 | 38 | 38 |
| L | 889 | 994 | 1035 | 1052 | 1102 | 1135 | 1150 | 1174 | 1196 | 1207 | 1262 | 30 | 57 | 91 | 110 |
| F | 38 | 38 | 38 | 38 | 38 | 38 | 38 | 38 | 38 | 38 | 38 | 39 | 39 | 39 | 39 |
| L | 133 | 395 | 399 | 403 | 655 | 686 | 829 | 856 | 876 | 1050 | 1139 | 1146 | 1179 | 1254 | 137 |
| F | 39 | 39 | 39 | 39 | 39 | 39 | 39 | 39 | 39 | 39 | 39 | 39 | 39 | 39 | 40 |
| L | 216 | 232 | 252 | 301 | 589 | 614 | 644 | 903 | 917 | 919 | 982 | 1128 | 1263 | 1296 | 1297 |
| F | 40 | 40 | 40 | 40 | 40 | 40 | 40 | 40 | 40 | 40 | 40 | 40 | 40 | 40 | 40 |
| L | 1328 | 107 | 119 | 312 | 316 | 319 | 362 | 370 | 411 | 412 | 506 | 629 | 703 | 787 | 792 |
| F | 40 | 41 | 41 | 41 | 41 | 41 | 41 | 41 | 41 | 41 | 41 | 41 | 41 | 41 | 41 |
| L | 795 | 1012 | 1276 | 51 | 302 | 320 | 322 | 336 | 540 | 579 | 713 | 810 | 909 | 1088 | 448 |
| F | 41 | 41 | 41 | 42 | 42 | 42 | 42 | 42 | 42 | 42 | 42 | 42 | 42 | 42 | 43 |
| L | 463 | 465 | 483 | 575 | 720 | 725 | 966 | 975 | 987 | 1003 | 1160 | 1197 | 1285 | 1337 | 146 |
| F | 43 | 43 | 43 | 43 | 43 | 43 | 43 | 43 | 43 | 43 | 43 | 43 | 43 | 43 | 44 |
| L | 309 | 341 | 386 | 493 | 558 | 615 | 631 | 790 | 879 | 894 | 1011 | 1175 | 80 | 245 | 344 |
| F | 44 | 44 | 44 | 44 | 44 | 44 | 44 | 44 | 44 | 44 | 44 | 44 | 45 | 45 | 45 |
| L | 734 | 747 | 766 | 805 | 819 | 901 | 930 | 946 | 1008 | 1043 | 1234 | 1310 | 1312 | 432 | 665 |
| F | 45 | 45 | 45 | 45 | 45 | 45 | 45 | 45 | 45 | 45 | 45 | 45 | 45 | 46 | 46 |
| L | 1024 | 1155 | 1167 | 50 | 114 | 115 | 204 | 328 | 348 | 378 | 654 | 714 | 778 | 834 | 839 |
| F | 46 | 46 | 46 | 47 | 47 | 47 | 47 | 47 | 47 | 47 | 47 | 47 | 47 | 47 | 47 |
| L | 852 | 877 | 915 | 939 | 1013 | 1017 | 1162 | 1231 | 1281 | 116 | 345 | 347 | 469 | 496 | 515 |
| F | 47 | 47 | 47 | 47 | 47 | 47 | 47 | 47 | 47 | 48 | 48 | 48 | 48 | 48 | 48 |
| L | 555 | 591 | 799 | 1095 | 1178 | 1202 | 1248 | 1255 | 70 | 123 | 333 | 731 | 772 | 1096 | 1113 |
| F | 48 | 48 | 48 | 48 | 48 | 48 | 48 | 48 | 49 | 49 | 49 | 49 | 49 | 49 | 49 |
| L | 1154 | 1186 | 1215 | 23 | 324 | 374 | 475 | 598 | 769 | 780 | 958 | 1028 | 1140 | 1301 | 29 |
| F | 49 | 49 | 49 | 50 | 50 | 50 | 50 | 50 | 50 | 50 | 50 | 50 | 50 | 50 | 51 |
| L | 138 | 142 | 191 | 446 | 522 | 524 | 767 | 1115 | 1235 | 120 | 458 | 567 | 607 | 900 | 1100 |
| F | 51 | 51 | 51 | 51 | 51 | 51 | 51 | 51 | 51 | 52 | 52 | 52 | 52 | 52 | 52 |
| L | 1129 | 1143 | 1199 | 1200 | 87 | 161 | 200 | 693 | 699 | 719 | 1059 | 1082 | 8 | 83 | 217 |
| F | 52 | 52 | 52 | 52 | 53 | 53 | 53 | 53 | 53 | 53 | 53 | 53 | 54 | 54 | 54 |
| L | 392 | 474 | 490 | 549 | 1110 | 1187 | 1340 | 231 | 372 | 375 | 466 | 503 | 597 | 776 | 833 |
| F | 54 | 54 | 54 | 54 | 54 | 54 | 54 | 55 | 55 | 55 | 55 | 55 | 55 | 55 | 55 |
| L | 841 | 943 | 1227 | 1302 | 1360 | 35 | 210 | 388 | 434 | 642 | 723 | 916 | 972 | 1103 | 1201 |
| F | 55 | 55 | 55 | 55 | 55 | 56 | 56 | 56 | 56 | 56 | 56 | 56 | 56 | 56 | 56 |
| L | 1258 | 1309 | 1356 | 79 | 124 | 182 | 355 | 394 | 825 | 1349 | 346 | 387 | 660 | 843 | 931 |
| F | 56 | 56 | 56 | 57 | 57 | 57 | 57 | 57 | 57 | 57 | 58 | 58 | 58 | 58 | 58 |
| L | 1032 | 1099 | 1145 | 1355 | 102 | 181 | 185 | 199 | 373 | 435 | 779 | 872 | 1019 | 1026 | 1075 |

TABLE 14-continued

| | | | | | | | | | | | | | | | |
|---|---|---|---|---|---|---|---|---|---|---|---|---|---|---|---|
| F | 58 | 58 | 58 | 58 | 59 | 59 | 59 | 59 | 59 | 59 | 59 | 59 | 59 | 59 | 59 |
| L | 1311 | 1336 | 315 | 538 | 820 | 822 | 865 | 932 | 978 | 1204 | 1239 | 1271 | 136 | 139 | 154 |
| F | 59 | 59 | 60 | 60 | 60 | 60 | 60 | 60 | 60 | 60 | 60 | 60 | 61 | 61 | 61 |
| L | 485 | 697 | 959 | 984 | 1048 | 1068 | 86 | 156 | 366 | 509 | 863 | 1070 | 1091 | 1142 | 1220 |
| F | 61 | 61 | 61 | 61 | 61 | 61 | 62 | 62 | 62 | 62 | 62 | 62 | 62 | 62 | 62 |
| L | 1292 | 1313 | 1354 | 53 | 113 | 189 | 646 | 827 | 851 | 873 | 977 | 1004 | 1198 | 259 | 471 |
| F | 62 | 62 | 62 | 63 | 63 | 63 | 63 | 63 | 63 | 63 | 63 | 63 | 63 | 64 | 64 |
| L | 488 | 707 | 976 | 84 | 640 | 669 | 797 | 996 | 1083 | 1183 | 1338 | 514 | 582 | 732 | 1085 |
| F | 64 | 64 | 64 | 65 | 65 | 65 | 65 | 65 | 65 | 65 | 65 | 66 | 66 | 66 | 66 |
| L | 1265 | 38 | 736 | 739 | 801 | 884 | 1042 | 1127 | 201 | 443 | 511 | 710 | 1331 | 36 | 353 |
| F | 66 | 67 | 67 | 67 | 67 | 67 | 67 | 67 | 68 | 68 | 68 | 68 | 68 | 69 | 69 |
| L | 361 | 670 | 968 | 1229 | 1259 | 73 | 238 | 562 | 694 | 782 | 815 | 1163 | 1273 | 10 | 306 |
| F | 69 | 69 | 69 | 69 | 69 | 70 | 70 | 70 | 70 | 70 | 70 | 70 | 70 | 71 | 71 |
| L | 307 | 634 | 1005 | 1353 | 65 | 131 | 134 | 151 | 214 | 816 | 1010 | 1098 | 1237 | 144 | 1144 |
| F | 71 | 71 | 71 | 71 | 72 | 72 | 72 | 72 | 72 | 72 | 72 | 72 | 72 | 73 | 73 |
| L | 127 | 436 | 592 | 77 | 401 | 758 | 765 | 1350 | 590 | 658 | 754 | 1057 | 1314 | 578 | 649 |
| F | 74 | 74 | 74 | 75 | 75 | 75 | 75 | 75 | 76 | 76 | 76 | 76 | 76 | 77 | 77 |
| L | 1330 | 1211 | 1219 | 450 | 802 | 944 | 1278 | 1339 | 62 | 100 | 445 | 553 | 41 | 476 | 599 |
| F | 77 | 78 | 78 | 79 | 79 | 79 | 79 | 79 | 80 | 80 | 80 | 80 | 81 | 81 | 81 |
| L | 1169 | 1358 | 230 | 300 | 303 | 518 | 1166 | 1209 | 1348 | 1112 | 1283 | 1250 | 17 | 68 | 203 |
| F | 81 | 81 | 82 | 82 | 82 | 82 | 82 | 82 | 82 | 83 | 83 | 84 | 85 | 85 | 85 |
| L | 565 | 577 | 1170 | 1287 | 28 | 784 | 1222 | 1293 | 19 | 800 | 821 | 1351 | 108 | 416 | 845 |
| F | 86 | 86 | 86 | 86 | 87 | 87 | 87 | 87 | 88 | 88 | 88 | 88 | 89 | 90 | 90 |
| L | 1051 | 1061 | 1288 | 914 | 1077 | 752 | 757 | 1105 | 360 | 451 | 1352 | 74 | 817 | 940 | 1249 |
| F | 90 | 90 | 90 | 91 | 91 | 92 | 92 | 92 | 93 | 93 | 94 | 96 | 97 | 97 | 97 |
| L | 159 | 721 | 924 | 164 | 380 | 76 | 438 | 926 | 1299 | 1316 | 188 | 616 | 1307 | 521 | 583 |
| F | 98 | 98 | 99 | 101 | 101 | 102 | 102 | 102 | 102 | 102 | 103 | 103 | 103 | 104 | 105 |
| L | 129 | 630 | 1041 | 1164 | 1260 | 157 | 1093 | 1138 | 1334 | 624 | 1277 | 1308 | 764 | 456 | 1218 |
| F | 106 | 106 | 107 | 107 | 107 | 108 | 111 | 113 | 113 | 114 | 114 | 114 | 116 | 117 | 117 |
| L | 950 | 1279 | 937 | 1137 | 449 | 532 | 82 | 608 | 1168 | 1332 | 417 | 622 | 652 | 269 | 1266 |
| F | 118 | 118 | 119 | 119 | 120 | 121 | 122 | 122 | 123 | 124 | 125 | 126 | 126 | 128 | 128 |
| L | 581 | 628 | 672 | 525 | 550 | 812 | 39 | 381 | 756 | 166 | 267 | 1092 | 1020 | 952 | 617 |
| F | 131 | 132 | 132 | 133 | 133 | 133 | 134 | 136 | 137 | 138 | 138 | 138 | 141 | 144 | 146 |
| L | 1039 | 1165 | 1038 | 1053 | 519 | 814 | 1217 | 1018 | 893 | 1040 | 520 | 531 | 1306 | 533 | 1267 |
| F | 149 | 151 | 162 | 162 | 163 | 168 | 172 | 179 | 182 | 182 | 189 | 190 | 211 | 213 | 218 |
| L | 895 | 1090 | | | | | | | | | | | | | |
| F | 228 | 280 | | | | | | | | | | | | | |

5. Screening for Expression Plasmids with Functional Chimerized Fusion ABE Protein in *E. coli*

Figure 2:
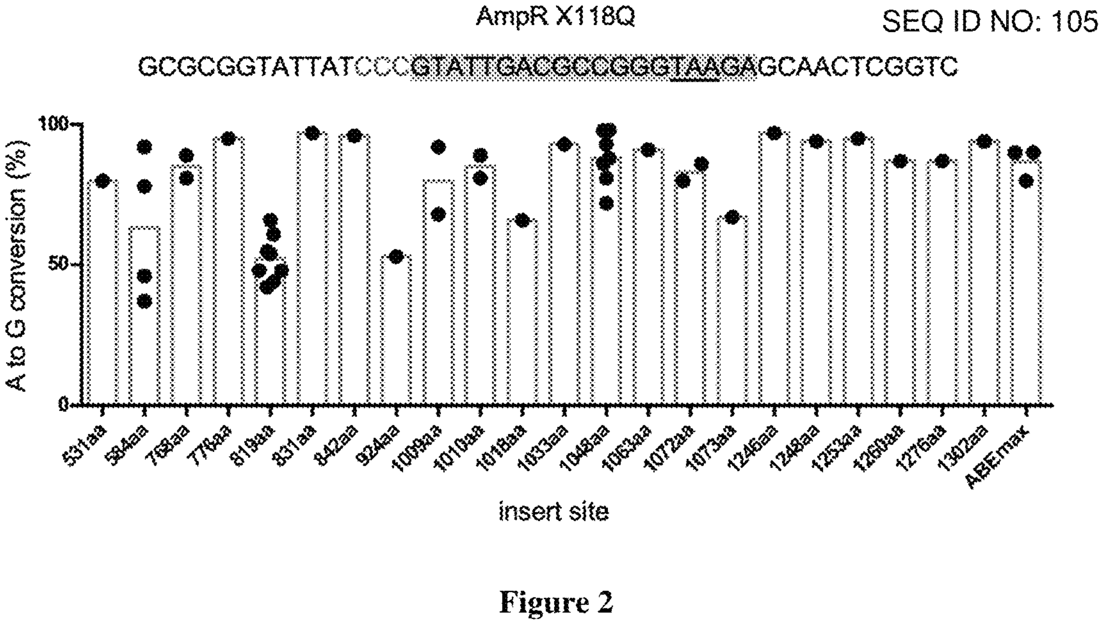
FIG. 2 is a schematic diagram of the present disclosure showing the screened nCas9 effective insertion sites and their base editing efficiency.

The bacteria was spread on several LB agar plates containing 10 μg/mL of kanamycin, and incubated for 16 h at 37° C. after above-mentioned transformation and 1 h of recovery in SOC medium. Then the bacterial colonies were scraped from the plates, resuspended in 100 mL of LLB containing 500 μM of IPTG. The culture was incubated for 10-12 h to induce the expression of nCas9 and repair the mutation on AmpR (A118X). Then cells with a reduced amount (5 mL, 1 mL, 500 μL, 100 μL) were seeded into 15 cm LB agar plates containing 10 μg/mL of ampicillin and 10 μg/mL of kanamycin. The plates were incubated overnight at 37° C., and then bacteria colonies were selected and subjected to Sanger sequencing for estimating the base editing on AmpR (A118X) and determining the insert loci of TadA-TadA*. Loci were selected as follows, and the specific positions were 51, 62, 63, 249, 531, 584, 719, 768, 770, 776, 782, 790, 808, 819, 831, 832, 842, 893, 924, 1009, 1010, 1018, 1033, 1050, 1051, 1063, 1072, 1073, 1090, 1227, 1246, 1248, 1253, 1260, 1263, 1276, 1290, 1302 and 1346, and the fragment of TadA-TadA* was inserted at the C-terminus of these loci. After ampicillin-resistance screening, and sequencing analysis of AmpR (A118X) site repair, it was found that the loci mentioned above with insertion of TadA-TadA* could form the chimeric fusion version of ABE with the function of base editing, and the corresponding insertion sites and efficiency of base editing are shown in FIG. 2.

6. Detection of Mutation Efficiency in *E. coli*

Figure 3:
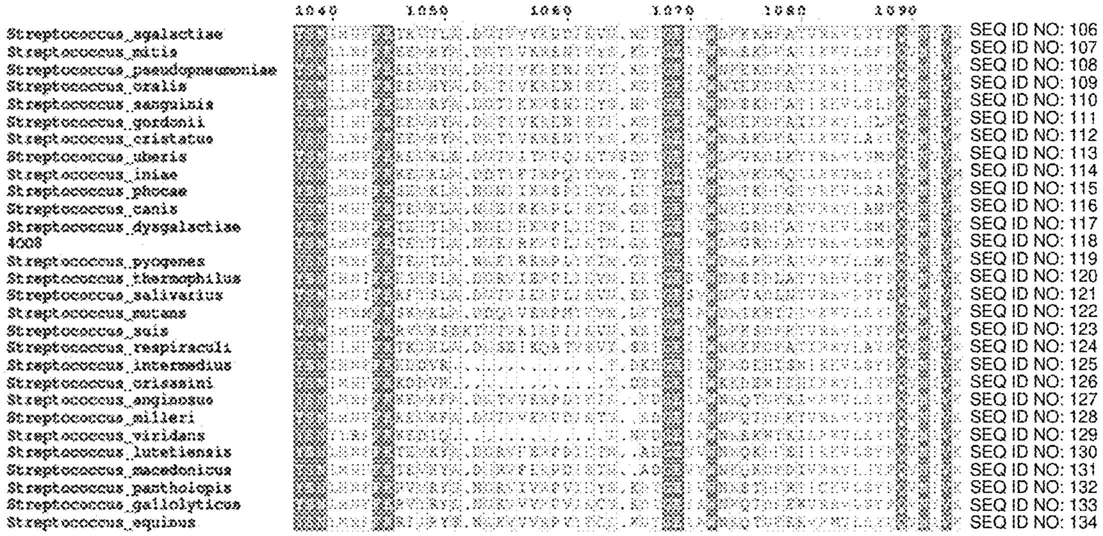
FIG. 3 is a schematic diagram of the present disclosure showing the comparison of non-conservative regions of the homologs of SpCas9.

Firstly, *E. coli* of the electro-transfected random insertion library was well spread on agarose plates containing antibiotic ampicillin, and incubated overnight in an incubator. Positive colonies were selected, and subjected to Sanger sequencing analysis with primer (cttttcggggaaatgtgggaaatgtgcgcggaacc) (SEQ ID NO: 87) and primer (cggatgcctagacaggtgttcaa) (SEQ ID NO: 88) for the determination of the mutation efficiency of adenine at the A118X locus and the corresponding insertion position of the fragment of TadA-TadA* on nCas9 (FIG. 2). In the 43 insertion sites recovered from the screening library, 9 sites are clustered in the short fragment (16-aa), which are located in 1048Thr, 1050Ile, 1051Thr, 1052Leu, 1054Asn, 1056Glu, 1057Ile, 1059Lys and 1063Ile. The accumulation of these sites in the screening library is specific, because in the unscreened library, these sites were inserted only 61, 39, 90, 38, 5, 29, 76, 53 and 25 times respectively, much less than some positions, such as other sites unrecovered after screening (e.g., 1090Pro insert 280 times). Therefore, a fragment of 16 amino acids has great tolerance to exogenous fragment insertion, and can be unnecessary to the function of nCas9. This fragment is non-conservation in 28 SpCas9 orthologs (FIG. 3). Thus, during the following construction of eukaryotic expression vectors, 1048Thr-1063Ile region was substituted with TadA-TadA* to generate CE-ABE$^{1048\text{-}1063}$.

7. Comparison of On-Target Editing Efficiency of ABEmax and Various CE-ABE in Human Cells After functional CE-ABE was obtained by screening in prokaryocytes, the on-target base editing efficiency of CE-ABE in HEK293T cells were further detected, and the process is used as follows:

Firstly, eukaryotic expression vectors of CE-ABE were constructed respectively:

After being successfully inserted into the 43 fragments of TadA-TadA* mentioned above, the editors with the function of adenine deamination were subjected to PCR amplification using the forward primer (agggagagccgccaccatgaaacggacagccgac) (SEQ ID NO: 89) and the reverse primer (tcctcttcttcttgggctcgaattcgctgccgtcggc) (SEQ ID NO: 90), to obtain 20 fragments of CE-ABE.

The pCMV-ABEmax plasmid was amplified using the forward primer (ggtggcggctctccctatagtgagtc) (SEQ ID NO: 91) and the reverse primer (cccaagaagaagaggaaagtctaacc) (SEQ ID NO: 92) to obtain the fragment of SEQ ID NO: 35.

The fragments were amplified by PCR with Vazyme high-fidelity enzyme kit (Vazyme, P501-d2). The PCR reaction system used as follows:

TABLE 15

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysates | 3-5 μL |

The PCR procedure used is as follows:

TABLE 16

| | | |
|---|---|---|
| 1 cycle | 98° C. | 3 min |
| 10 cycle | 95° C. | 20 s |
| | 68° C. | 30 s, −1° C./cycle |
| | 72° C. | 4 min |
| 25 cycle | 95° C. | 20 s |
| | 58° C. | 30 s |
| | 72° C. | 4 min |
| 1 cycle | 72° C. | 5 min |
| 1 cycle | 4° C. | ∞ |

The PCR amplification products were purified and recovered by AxyPrep PCR Clean-up kit (Axygen, AP-PCR-500G), and subjected to recombination reaction, then the fragments were recombinated by Gibson Assembly Master Mix recombinant kit (NEB, E2611S), and the reaction system used is as follows:

TABLE 17

| | |
|---|---|
| Gibson Assembly Master Mix (2×) | 5 μL |
| PCR fragment of CE-ABE | 150 ng |
| PCR fragment of CMV-ABE (SEQ ID NO: 35) | 50 ng |
| Sterile water | Add water to 10 μL |

The reaction solutions were mixed and incubated for 1 h at 50° C., and subjected to transformation subsequently, recovered for 30 min, and spread on a LB agar plate with ampicillin resistance, incubated overnight at 37° C. Single clones were selected for verification by sequencing to obtain a pCMV-CE-ABE plasmid (SEQ ID NO: 36-55). Plasmid extraction was carried out with AxyPrep plasmids miniprep kit (Axygen, AP-MN-P-250G). Sanger sequencing was carried out.

HEK293FT cells (from ATCC) were recovered and cultured in a 10 cm Petri dish (Corning, 430167), where the medium was DMEM (HyClone, SH30243.01) containing 10% (v/v) fetal bovine serum (HyClone, SV30087). The culture temperature was 37° C., and the concentration of $CO_2$ was 5%. When the cell density was about 80% after subculture, the cells were distributed into 12-well plates. The 12-well plates were subjected to the treatment of coating with a 1:10 diluted polylysine solution (Sigma, P4707-50 mL) before use.

1) Cell transfection was carried out when the cell density was about 80% after seeded for 12-14 h. The amount of plasmids transfected was 700 ng of CE-ABE (SEQ ID NO: 36-55) plasmid, and 300 ng of sgRNA of 1ABE-site 1 (SEQ ID NO: 12) per well. The plasmids were mixed in 100 μL of Opti-MEM (Gibco, 11058021) medium. The pCMV-ABEmax plasmid was taken as a positive control group, 700 ng of plasmids (Addgene, #112095) and 300 ng of sgRNA of ABEmax-site 1 (SEQ ID NO: 12) were added into each well.

2) In addition, 3 μL of transfection reagent Lipofectamine 2000 (Thermo, 11668019) was mixed into 100 μL of Opti-MEM medium, and let stand for 5 min.

3) Opti-MEM mixed with plasmids were added to Opti-MEM mixed with Lipofectamine 2000, pipetted slowly to mix well, let stand for 20 min.

4) The transfection solution after mixing and standing mentioned above were added to culturing cells respectively.

5) The solution was changed with DMEM containing 10% FBS after transfection for 6 h.

6) After transfection for 48 h, the medium was discarded, and the cells were washed once with PBS, then the cells were digested with TE (Thermo Fisher, R001100), and DMEM containing 10% FBS was used to terminate digestion. Cells were centrifuged and collected, and finally resuspended with the medium.

7) The resuspended cells were sorted by FACS (Fluorescence activated cell sorting), and cells with the top 5% of GFP fluorescent intensity were collected, at least 5,000 cells were collected for each sample.

⅙ of the cells collected above were lysed directly, and the fragments of target sites were amplified by PCR, with the forward primer: aaagatcttcacaggctaccccc (SEQ ID NO: 103) and the reverse primer: aatccacagcaacaccctctcc (SEQ ID NO: 104). The fragments of target sites of each genome were amplified by PCR with Vazyme high-fidelity enzyme kit (Vazyme, P501-d2). The PCR reaction system used is as follows:

TABLE 18

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Sterile water | 3-5 μL |

The PCR procedure used is as follows:

TABLE 19

| | | |
|---|---|---|
| 1 cycle | 98° C. | 3 min |
| 10 cycle | 95° C. | 20 s |
| | 68° C. | 30 s, −1° C./cycle |
| | 72° C. | 30 s |
| 25 cycle | 95° C. | 20 s |
| | 58° C. | 30 s |
| | 72° C. | 30 s |
| 1 cycle | 72° C. | 5 min |
| 1 cycle | 4° C. | ∞ |

Figure 4:
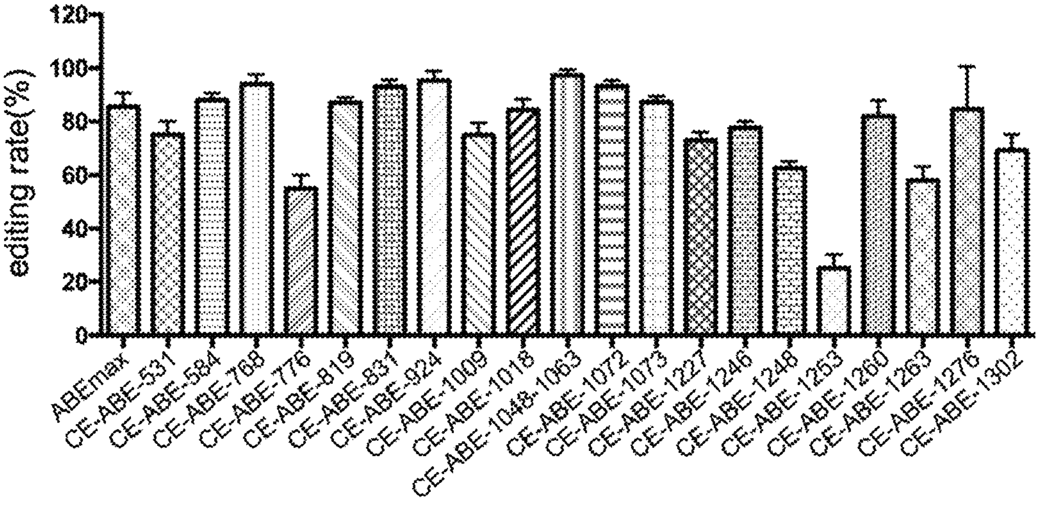
FIG. 4 is a schematic diagram of the present disclosure showing the results of base editing of screened CE-ABE on the human cell genome.

The PCR amplification products were purified and recovered by AxyPrep PCR Clean-up kit (Axygen, AP-PCR-500G), and were subjected to Sanger sequencing. The sequencing result of corresponding insertion sites are shown in FIG. 4.

8. Comparison of Off-Targeting Caused by ABEmax and CE-ABE in Human Cells 30,000 of 5% GFP-positive cells mentioned above were collected, centrifuged and the supernatant was discarded, then TRIzol (Thermo Fisher, 15596018) reagent was added, and total RNA was extracted according to the instructions. Thereafter, part of the RNA was taken to reverse transcription, and the detailed steps are as follows:

1) Total RNA extraction: 1 mL of TRIzol reagent was added, pipetted for several times to homogenize the cells. TRIzol was pipetted into nuclease-free microtubes. Then 200 μL of chloroform was added and mixed well, centrifuged for 15 min at 12,000 rpm in pre-cooled centrifuge at 4° C.; 400 μL of the supernatant was carefully pipetted into a new nuclease-free microtube, and 400 μL of isopropanol was added and mixed well at room temperature, let stand for 10 min; after centrifuged for 15 min at 12,000 rpm in pre-cooled centrifuge at 4° C., the supernatant was discarded; 1 mL of 75% ethanol was added, mixed and centrifuged for 15 min at 12,000 rpm in pre-cooled centrifuge at 4° C., and the supernatant was discarded, the precipitate was dried naturally, and 20-30 μL of nuclease-free water was added, and the concentration of RNA was determined by NanoDrop.

2) Reverse transcription of total RNA to cDNA: HiScript® II Q RT SuperMix for qPCR (+g DNA wiper) kit was used. Firstly, genomic DNA was discarded from total RNA, 500 ng of total RNA, 2 μL of 4×gDNA wiper Mix (Vazyme, R223-01), added with water to 8 μL, incubated for 5 min at 42° C. Then the reverse transcription reaction was started, 2 μL of 5×HiScript® II qRT SuperMix II[a] (Vazyme, R223-01) was added into 8 μL of the reaction solution mentioned above. The mixture was incubated for 20 min at 50° C., then reacted at 85° C. for 2 min to inactivate the activity of reverse transcriptase, then cDNA was obtained for later detection.

Figure 5:
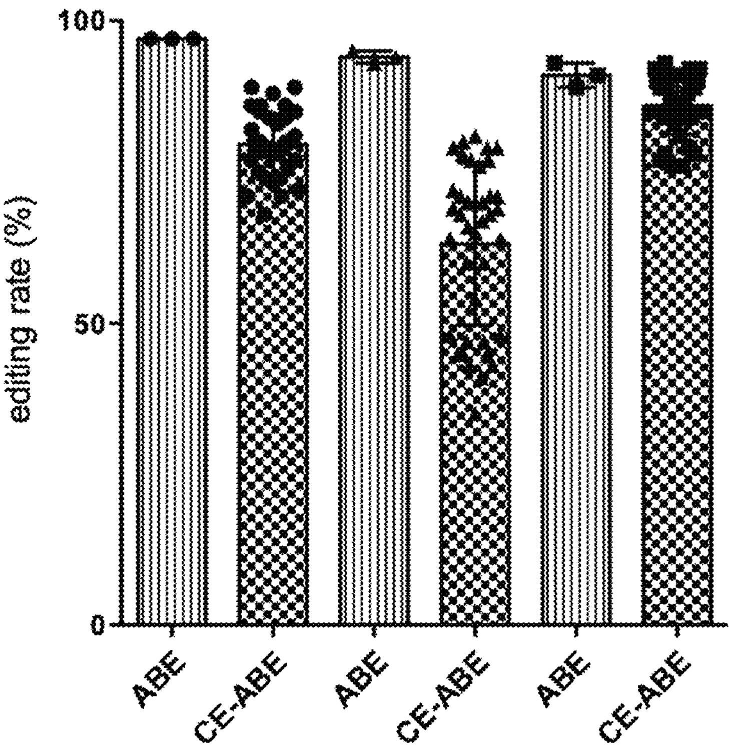
FIG. 5 is a schematic diagram of the present disclosure showing the off-target editing results of CE-ABE on the predicted RNA loci.
Figure 6:
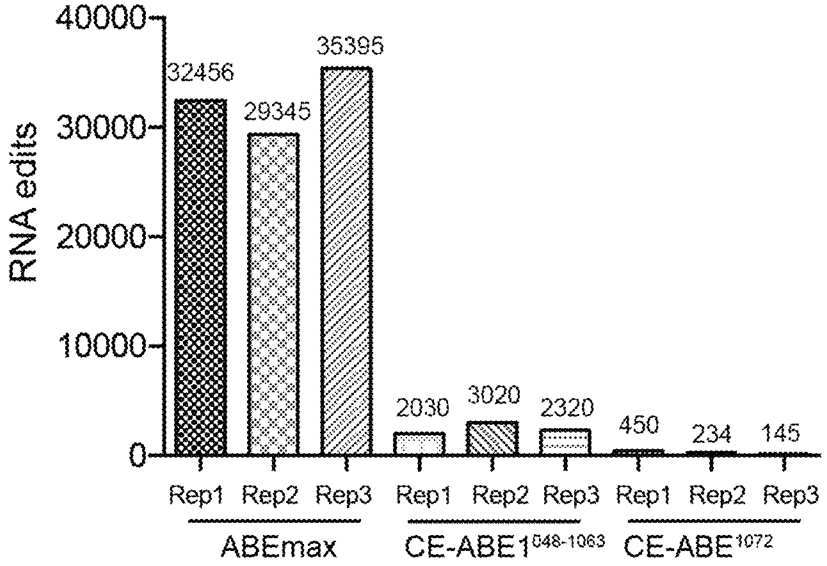
FIG. 6 is a schematic diagram of the present disclosure showing the off-target editing results caused by CE-ABE at the transcriptome level.

Three RNA off-target loci (chr19 (14518195), chr11 (62594034) and chr16 (25164711)) with high off-target rate were obtained from the previous RNA-seq data of cells transfected with ABEmax. Primers were designed for these three loci, and cDNA samples of CE-ABE were amplified for these three loci, followed by Sanger sequencing analysis, the results are shown in FIG. 5. It can be found by analysis that compared to ABEmax, all CE-ABEs have a significant decrease at the three RNA off-target loci. It is indicated that the chimeric deaminase inside nCas9 can effectively reduce the off-target editing of TadA-TadA* on part of RNA sites (FIG. 6).

Thereafter, whole transcriptome sequencing was applied to the RNA of cells transfected with CE-ABE$^{1048-1063}$, CE-ABE$^{1072}$ (the number after numbering refers to the insertion sites of the TadA-TadA* fragment inside nCas9) and ABEmax. All RNA samples were sequenced using Illumina HiSeq X Ten (2×150PE) of Novogene Bioinformation Institution (Beijing, China), with a read depth of about 20 million per sample. The readers were mapped to human reference genome (hg38) by STAR software (version 2.5.1), annotated with GENCODE v30. After deleting duplications, variants were recognized by GATK HaplotypeCaller (version 4.1.2), then filtered by QD (quality by depth), and all variants were verified by bam-readcount and quantified, with the parameter -q 20-b 30. The given editing should be at least ten folds, and it was required that at least 99% of the reads in these editing support the reference allele in wild-type samples. Finally, only A to G (for ABE) editing in transcript chain was considered to involve in downstream analysis. The detailed results are shown in FIG. 6, indicating that the CE-ABE chimerized at the loci 1048Thr-1063Ile and 1072 Val can significantly reduce the off-target editing of TadA-TadA* on RNA at the whole transcriptome level.

Figure 7:
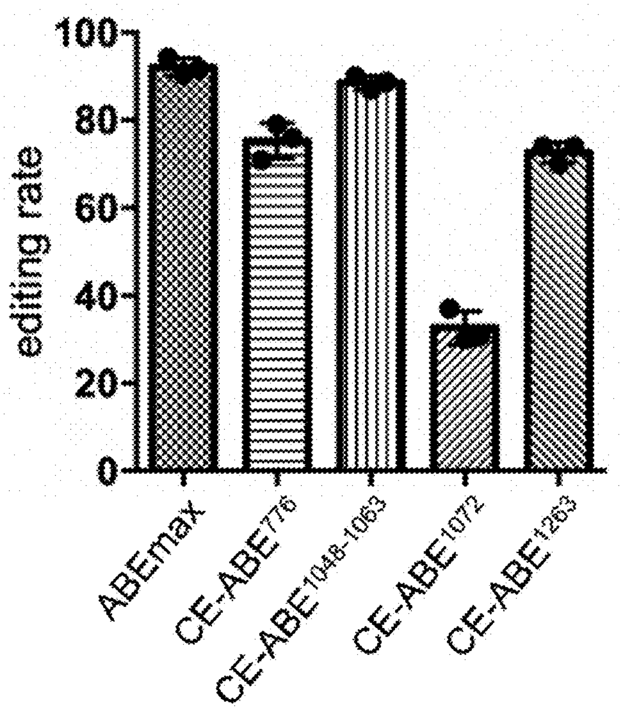
FIG. 7 is a schematic diagram of the present disclosure showing the results of on-target editing efficiency of CE-ABE in off-target assay samples.

Meanwhile, the on-target editing efficiency of three editors, ABEmax, CE-ABE$^{1048-1063}$ and CE-ABE$^{1072}$ was detected. The results show that although the on-target editing efficiency of CE-ABE-1072 was significantly lower than ABEmax, there was no significant difference between the on-target editing efficiency of CE-ABE$^{1048-1063}$ and ABEmax, and the detailed results are shown in FIG. 7.

9. The Base Editing Results of CE-ABE$^{1048-1063}$ at Various Endogenous Gene Loci The on-target base editing efficiency and editing windows of CE-ABE$^{1048-1063}$ in HEK293T cells and N2a cells were further determined, and the process was as follows:

HEK293FT and N2a cells (from ATCC) were recovered and cultured in 10 cm petri dishes (Corning, 430167), and the culture medium was DMEM (HyClone, SH30243.01) containing 10% (v/v) fetal bovine serum (HyClone, SV30087). The culture temperature was 37° C. and the concentration of $CO_2$ was 5%. When the cell density was 80% after subculture, the cells were distributed into 12-well plates. The 12-well plates were subjected to the treatment of coating with a 1:10 diluted polylysine solution (Sigma, P4707-50ML) before use.

2) After the cells were seeded for 12-14 h with the cell density was about 80%, the cells were subjected to transfection. The amount of plasmids for transfection was 700 ng of CE-ABE$^{1048-1063}$ (SEQ ID NO: 45) per well, and for HEK293FT cells, 300 ng of plasmids containing gRNA was used for each loci (SEQ ID NO: 21-32); for N2a cells, 300 ng of plasmids containing gRNA was used for each loci (SEQ ID NO: 21-32). The plasmids were mixed in 100 μL of Opti-MEM (Gibco, 11058021) medium. The pCMV-AncBE4max was set as control, 700 ng of pCMV-ABEmax plasmids and 300 ng of plasmids containing gRNA for each loci were added into each well.

3) In addition, 3 μL of Lipofectamine 2000 transfection reagent (Thermo, 11668019) was mixed into 100 μL of Opti-MEM medium, and let stand for 5 min.

4) The Opti-MEM mixed with plasmids was added into the Opti-MEM mixed with Lipofectamine 2000, and the mixture was pipetted slowly and mixed well, let stand for 20 min.

5) The transfection solution after mixing and standing was added into culture cells respectively.

6) After transfection for 6 h, the solution was changed with DMEM containing 10% FBS. After transfection for 48 h, the medium was discarded, and the cells were washed with PBS once, digested with TE (Thermo Fisher, R001100) then, followed by terminating the digestion with DMEM containing 10% FBS. The cells were centrifuged and collected, and finally resuspended with the medium.

7) The resuspended cells were sorted by FACS (Fluorescence activated Cell Sorting), and since the GFP signal was on a plasmid containing gRNA, all GFP positive cells were sorted directly, and at least 5000 cells were collected for each sample.

The cells collected above were subjected to lysis and fragments of target sites were amplified with PCR. The fragments of target sites of each genome were amplified with PCR by Vazyme high-fidelity enzyme kit (Vazyme, P501-d2). The PCR reaction system used is as follows:

TABLE 20

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysate solution | 3-5 μL |

The PCR procedure used is as follows:

TABLE 21

| | | |
|---|---|---|
| 1 cycle | 98° C. | 3 min |
| 10 cycle | 95° C. | 20 s |
| | 68° C. | 30 s, −1° C./cycle |
| | 72° C. | 30 s |
| 25 cycle | 95° C. | 20 s |
| | 58° C. | 30 s |
| | 72° C. | 30 s |
| 1 cycle | 72° C. | 5 min |
| 1 cycle | 4° C. | ∞ |

Figure 8:
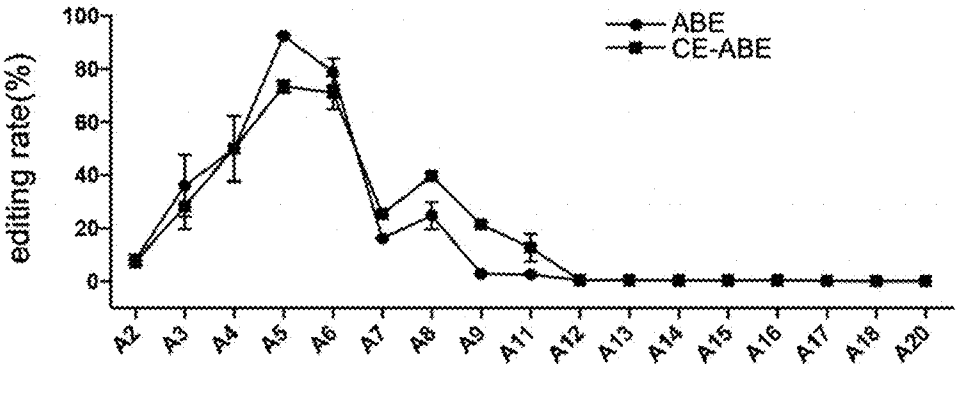
FIG. 8 is a schematic diagram of the present disclosure showing comparable editing efficiency of CE-ABE$^{1048-1063}$ and ABEmax in 293T cells.
Figure 9:
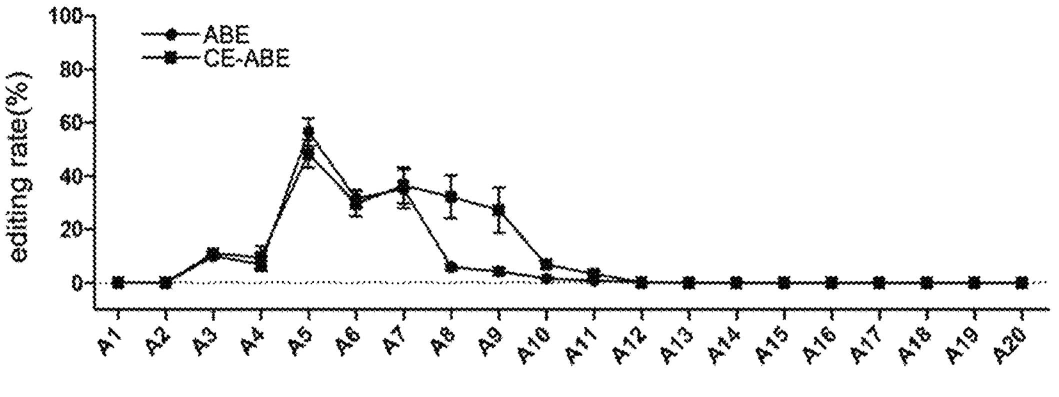
FIG. 9 is a schematic diagram of the present disclosure showing comparable editing efficiency of CE-ABE$^{1048-1063}$ and ABEmax in N2a cells.

The PCR amplification product was purified and recovered by AxyPrep PCR Clean-up kit (Axygen, AP-PCR-500G). PCR products with different barcodes were gathered and subjected to deep sequencing on the Illumina HiSeq X Ten (2×150PE) platform of Novogene Bioinformation Institution (Beijing, China). The adapter pairs of paired-end reads were removed, and paired-end reads of 11 bp or more of bases were combined into a single common read using AdaptorRemoval (version 2.2.2). Next, all processed reads were mapped to a target sequence by BWA-MEM algorithm (BWA v0.7.16). For each loci, the mutation rate was calculated by counting the bam reads with parameters -q 20-b 30. The indel (insertion or deletion) was calculated based on the reads of at least one nucleotide insertion or deletion in a protospacer. The frequency of indel was calculated as readers containing indels/total mapped readers. The results of sequencing are shown in FIGS. 8 and 9. The results indicate that the on-target base editing efficiency of CE-ABE$^{1048-1063}$ at multiple endogenous sites in HEK293T cells is comparable to that of ABEmax. Besides, the editing window of CE-ABE$^{1048-1063}$ shows no significant change, the detailed results are shown in FIGS. 8 and 9.

9. The Base Editing Results of CE-ABE$^{1048-1063}$ at Multiple Endogenous Gene Loci It has been found in above experiments that the on-target efficiency of CE-ABE with replacement of the fragment between 1048Thr-1063Ile with TadA-TadA* in nCas9 is the highest, while the low off-target efficiency is low. Furthermore, the 1048Thr-1063Ile peptide of nCas9 was replaced with APOBEC1 (SEQ ID NO: 68) and APOBEC3A (SEQ ID NO: 69) respectively, and the on-target base editing efficiency and editing windows of CE-ABE$^{1048-1063}$ were characterized in HEK293T cells. The procedure was as follows:

1) Firstly, the eukaryotic expression vectors of CE-ABE$^{1048-1063}$and CE-A3A$^{1048-1063}$ were constructed respectively:

The APOBEC1 fragment was amplified by PCR using the forward primer: catgaactttttcaagtccggaTCCgagaccccaggc (SEQ ID NO: 93) and the reverse primer: tttcgccgtttgtctcgctctctggtgttgctgac (SEQ ID NO: 94).

The APOBEC3A fragment was amplified by PCR using the forward primer: catgaactttttcaagtccggaTCCgagaccccaggc (SEQ ID NO: 95) and the reverse primer: tttcgccgtttgtctcgctctctggtgttgctgac (SEQ ID NO: 96).

The pCMV-AncBE4max was used as the template in PCR amplification with the forward primer: gagacaaacggcgaaaccggggagatc (SEQ ID NO: 97) and the reverse primer: cttgaaaaagttcatgatgttgc (SEQ ID NO: 98).

The fragments were amplified by PCR with Vazyme high-fidelity enzyme kit (Vazyme, P501-d2). The PCR reaction system used is as follows:

TABLE 22

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Template DNA | 1 μL |

The PCR procedure used is as follows:

TABLE 23

| | | |
|---|---|---|
| 1 cycle | 98° C. | 3 min |
| 10 cycle | 95° C. | 20 s |
| | 68° C. | 30 s, −1° C./cycle |
| | 72° C. | 4 min |
| 25 cycle | 95° C. | 20 s |
| | 58° C. | 30 s |
| | 72° C. | 4 min |
| 1 cycle | 72° C. | 5 min |
| 1 cycle | 4° C. | ∞ |

The PCR amplification product was purified and recovered by AxyPrep PCR Clean-up kit (Axygen, AP-PCR-500G), and subjected to recombination; the fragments were recombinated with Gibson Assembly Master Mix recombinant kit (NEB, E2611S), and the reaction system used is as follows:

TABLE 24

| | |
|---|---|
| Gibson Assembly Master Mix (2×) | 5 μL |
| PCR fragments of APOBEC1 and APOBEC3A | 150 ng |
| PCR fragment of pCMV-AncBE4max | 50 ng |
| Sterile water | Add water to 10 μL |

The reaction solutions were mixed and incubated for 1 h at 50° C., subjected to transformation subsequently, recovered for 30 min, and spread on a LB agar plate with ampicillin resistance, incubated overnight at 37° C. Single clones were selected for verification by sequencing to obtain a pCMV-CE-CBE$^{1048-1063}$ plasmid (SEQ ID NO: 56) and pCMV-CE-A3A$^{1048-1063}$ plasmid (SEQ ID NO: 70). Plasmid extraction was carried out with AxyPrep plasmids miniprep kit (Axygen, AP-MN-P-250G). Sanger sequencing was carried out.

HEK293FT cells (from ATCC) were recovered and cultured in 10 cm Petri dish (Corning, 430167), and the medium was DMEM (HyClone, SH30243.01) containing 10% (v/v) fetal bovine serum (HyClone, SV30087). The culture temperature was 37° C., and the concentration of $CO_2$ was 5%. When the cell density was about 80% after subculture, the cells were distributed into 12-well plates. The 12-well plates were subjected to the treatment of coating with a 1:10 diluted polylysine solution (Sigma, P4707-50 mL) before use.

2) Cell transfection was carried out when the cell density was about 80% after seeded for 12-14 h. The amount of plasmids used to transfect was 700 ng of CE-ABE (SEQ ID NO: 56) and CE-A3A (SEQ ID NO: 70) per well, and 300 ng plasmids containing gRNA for each loci (SEQ ID NO: 57-67). The plasmids were mixed in 100 μL of Opti-MEM (Gibco, 11058021) medium. The pCMV-AncBE4max plasmid was taken as a positive control group, 700 ng of pCMV-AncBE4max plasmids and 300 ng of plasmids containing sgRNA for each loci were added into each well.

3) In addition, 3 μL of transfection reagent Lipofectamine 2000 (Thermo, 11668019) was mixed into 100 μL of Opti-MEM medium, and let stand for 5 min.

4) Opti-MEM mixed with plasmids were added to Opti-MEM mixed with Lipofectamine 2000, and pipetted slowly to mix well, let stand for 20 min.

5) The transfection solution after mixing and standing mentioned above were added to culturing cells respectively.

6) The solution was changed with DMEM containing 10% FBS after transfection for 6 h. After transfection for 48 h, the medium was discarded, and the cells were washed once with PBS, then the cells were digested with TE (Thermo Fisher, R001100), and DMEM containing 10% FBS was used to terminate digestion. Cells were centrifuged and collected, and finally resuspended with the medium.

7) The resuspended cells were sorted by FACS (Fluorescence activated cell sorting), and since the GFP signal is on gRNA plasmids, we directly sorted all GFP positive cells, and at least 5,000 cells were collected for each sample.

The cells collected above were lysed directly, and the fragments of target sites were amplified by PCR. The fragments of target sites of each genome were amplified by PCR with Vazyme high-fidelity enzyme kit (Vazyme, P501-d2). The PCR reaction system used is as follows:

TABLE 25

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysate | 3-5 μL |

The PCR procedure used is as follows:

TABLE 26

| | | |
|---|---|---|
| 1 cycle | 98° C. | 3 min |
| 10 cycle | 95° C. | 20 s |
| | 68° C. | 30 s, −1° C./cycle |
| | 72° C. | 30 s |
| 25 cycle | 95° C. | 20 s |
| | 58° C. | 30 s |
| | 72° C. | 30 s |
| 1 cycle | 72° C. | 5 min |
| 1 cycle | 4° C. | ∞ |

Figure 10:
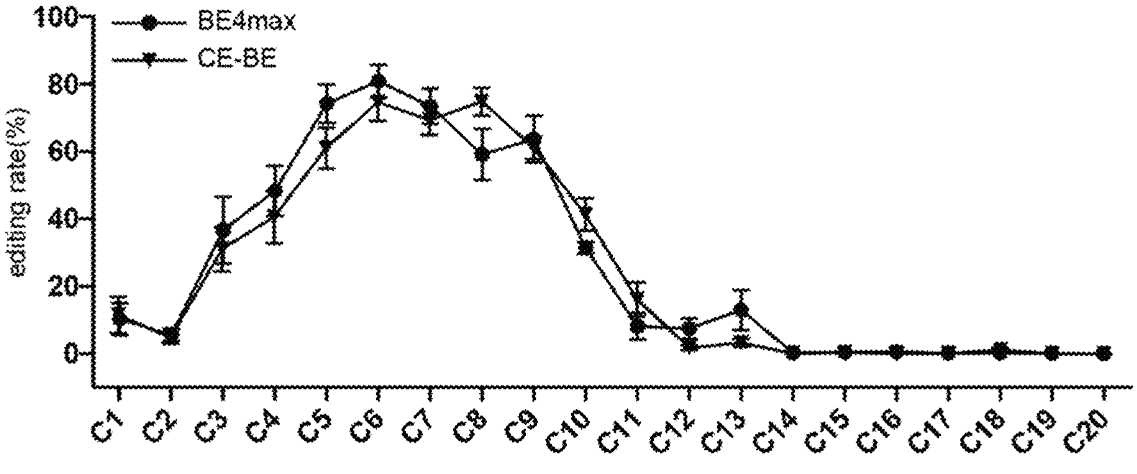
FIG. 10 is a schematic diagram of the present disclosure showing comparable editing efficiency of CE-BE$^{1048-1063}$ and AncBE4max in 293T cells.
Figure 11:
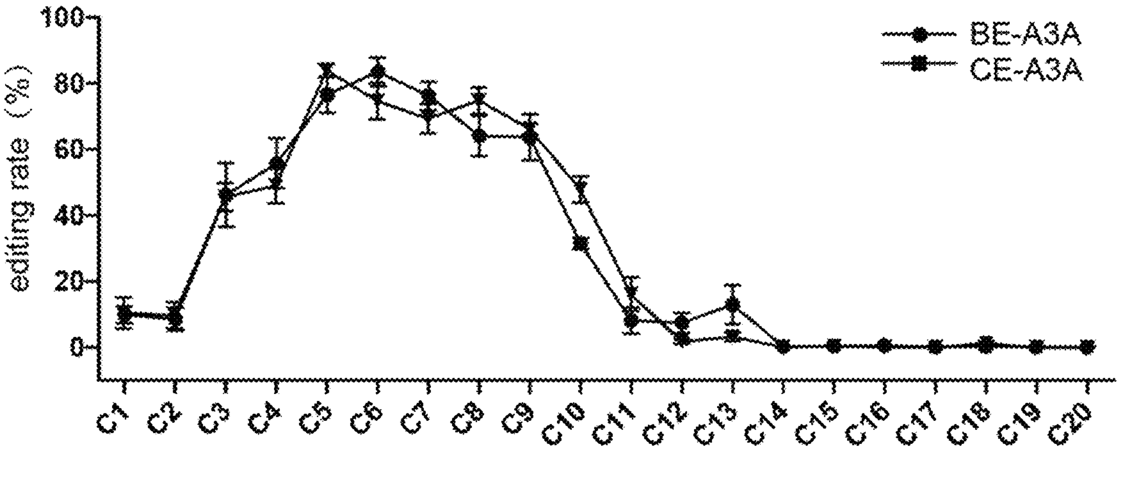
FIG. 11 is a schematic diagram of the present disclosure showing comparable editing efficiency of CE-A3A$^{1048-1063}$ and BE-A3A in 293T cells.

The PCR amplification product was purified and recovered by AxyPrep PCR Clean-up kit (Axygen, AP-PCR-500G). PCR products with different barcodes were gathered and subjected to deep sequencing on the Illumina HiSeq X Ten (2×150PE) platform of Novogene Bioinformation Institution (Beijing, China). The adapter pairs of a paired-end reads were removed, and paired-end reads of 11 bp or more of bases were combined into a single common read using AdaptorRemoval (version 2.2.2). Next, all processed reads were mapped to a target sequence by BWA-MEM algorithm (BWA v0.7.16). For each loci, the mutation rate was calculated by counting the bam reads with parameters -q 20-b 30. The indel was calculated based on the reads of at least one nucleotide insertion or deletion in a protospacer. The frequency of an indel was calculated as readers containing indels/total mapped readers. The results of sequencing are shown in FIGS. 10 and 11. The results indicate that the on-target base editing efficiency of CE-BE at multiple endogenous sites in HEK293T cells is comparable to that of original BE. Besides, the editing window of CE-ABE shows no significant change, the detailed results are shown in FIG. 8, and FIGS. 10 and 11.

11. The Off-Target Editing Results of CE-ABE and CE-A3A on RNA in Human Cells 300000 of 5% of GFP positive cells described above were sorted by FACS, centrifuged and the supernatant was discarded, the TRIzol (Thermo Fisher, 15596018) reagent was added. Extraction of total RNA was carried out according to instructions. Next, part of total RNA was taken for reverse transcription, and the detailed steps are as follows:

Total RNA extraction: 1 mL of TRIzol reagent was added, and pipetted for several times to homogenize the cells. TRIzol was pipetted into a nuclease-free centrifuge microtube. Then, 200 μL of chloroform was added, mixed well, and centrifuged for 15 min at 12000 rpm in a pre-cooled centrifuge at 4° C.; 400 μL of the supernatant was pipetted carefully into a new nuclease-free centrifuge microtube, 400 μL of isopropanol was added, mixed well at room temperature and let stand for 10 min; after centrifuged for 15 min at 12000 rpm in a 4° C. pre-cool centrifuge, the supernatant was discarded; 1 mL of 75% ethanol was added, mixed well and centrifuged for 15 min at 12000 rpm in a pre-cooled centrifuge at 4° C., then the supernatant was discarded, the precipitate was dried naturally; 20-30 μL of nuclease-free water was added, and the RNA concentration test was carried out by NanoDrop.

Figure 12:
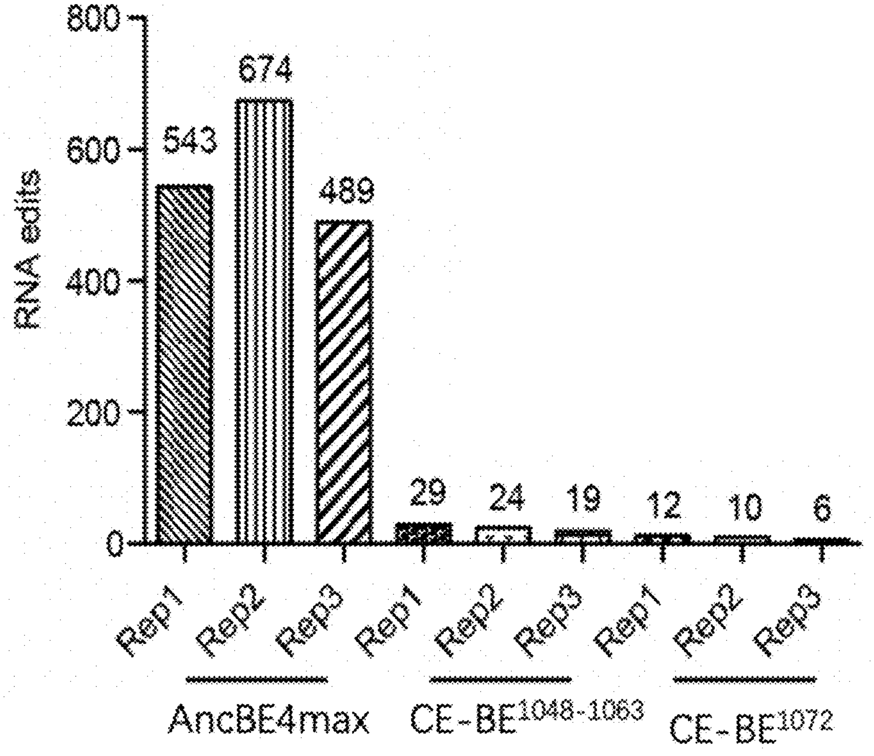
FIG. 12 is a schematic diagram of the present disclosure showing the off-target editing on RNA caused by CE-BE and AncBE4max in 293T cells.
Figure 13:
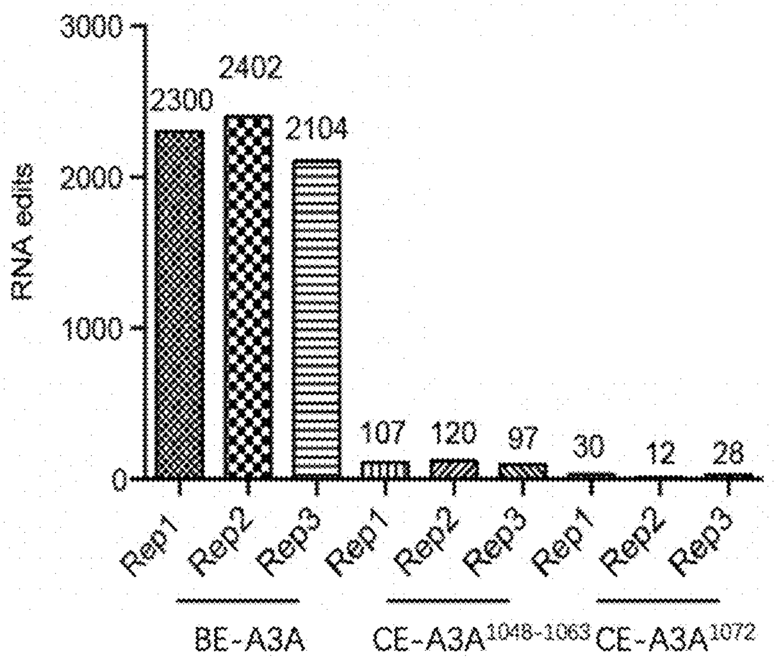
FIG. 13 is a schematic diagram of the present disclosure showing the off-target editing on RNA caused by CE-A3A and BE-A3A in 293T cells.

Subsequently, whole transcriptome sequencing was performed for BE4max, CE-CBE$^{1048-1063}$, CE-CBE$^{1072}$, BE-A3A, CE-A3A$^{1048-1063}$, CE-A3A$^{1072}$, and all RNA samples were subjected to sequencing using Illumina HiSeq X Ten (2×150PE) of Novogene Bioinformation Institution (Beijing, China), with a read depth of about 20 million per sample. The readers were mapped to human reference genome (hg38) by STAR software (version 2.5.1), annotated with GENCODE v30. After deleting duplicates, variants were recognized by GATK HaplotypeCaller (version 4.1.2), then filtered by QD (quality by depth), and all variants were verified by bam-readcount and quantified, with the parameter -q20-b30. The given editing should be at least ten folds, and it was required that at least 99% of the reads in these editing support reference allele in wild-type samples. Finally, only C to T editing in transcript chain was considered to involve in downstream analysis. FIGS. 12 and 13 indicate that CE-CBE$^{1048-1063}$, CE-CBE$^{1072}$, CE-A3A$^{1048-1063}$ and CE-A3A$^{1072}$ chimerized at the loci 1048Thr-1063Ile and 1072 Val can significantly reduce the off-target editing of APOBEC1 and APOBEC3A on RNA at whole transcriptome level.

12. The Off-Target DNA Editing Results of CE-CBE$^{1048-1063}$ and CE-A3A$^{1048-1063}$ in Mouse Embryos CE-CBE$^{1048-1063}$ and CE-A3A$^{1048-1063}$ were transcribed to mRNA in vitro, and at first, CE-CBE$^{1048-1063}$ and CE-A3A$^{1048-1063}$ were amplified respectively by PCR using the forward primer: ATGCCTGCTATTGTCTTCCCAA (SEQ ID NO: 99) and the reverse primer: AACGGGGACTTTCCAAAATGTC (SEQ ID NO: 100) to obtain linearized fragments of CE-CBE$^{1048-1063}$ and CE-A3A$^{1048-1063}$. For sgRNA transcription, oligonucleotide chain was synthesized first, and linked to a linearized PUC57-Sp sgRNA plasmid after annealing. The PUC57 plasmid constructed was verified by Sanger sequencing, sgRNA was amplified by PCR using the forward primer: TCTCGCGCGTTTCGGTGATGACGG (SEQ ID NO: 101) and the reverse primer: AAAAAAATCTCGCCAACAAGTTGAC (SEQ ID NO: 102):

The detailed steps are as follows:

TABLE 27

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| CE-CBE/CE-A3A/sgRNA | 1 ng |

The PCR procedure used is as follows:

TABLE 28

| | | |
|---|---|---|
| 1 cycle | 98° C. | 3 min |
| 10 cycle | 95° C. | 20 s |
| | 68° C. | 30 s, −1° C./cycle |
| | 72° C. | 4 min |
| 25 cycle | 95° C. | 20 s |
| | 58° C. | 30 s |
| | 72° C. | 4 min |
| 1 cycle | 72° C. | 5 min |
| 1 cycle | 4° C. | ∞ |

The following operation was conducted under nuclease-free condition: Firstly, RNAsecure™ RNase Inactivation Reagent (Invitrogen™, AM7005) was added into the PCR product at a ratio of 1:25, set to dry bath at 60° C. for 10 min; next, the PCR fragments were recovered with MinElute PCR Purification Kit (QIAGEN, 28004).

(1) In Vitro Transcription of nCas9

In vitro transcription of Cas9 was carried out according to the instructions of mMESSAGE mMACHINE™ T7 ULTRA Transcription Kit (Invitrogen™, AM1345), and the reaction solution was added as follows:

10 μL T7 2×NTP/ARCA
2 μL 10×T7Reaction Buffer
600 ng template PCR fragment of Cas9
2 μL T7 Enzyme Mix
Add Nuclease-free water to 20 μL The reaction solution was reacted on a PCR thermal cycler after well mixed, and cover-heating temperature was set as 50° C., the system temperature was set as 37° C.; 1 μL of TURBO DNase digested template DNA was added after reacted for 2 h, and reacted at 37° C. for 15 min. Thereafter, poly-A was added for subsequent reaction, and the system was as follows:

20 μL the transcription product described above
20 μL 5×E-PAP Buffer
10 μL 25 mM $MnCl_2$
10 μL ATP Solution
36 μL Nuclease-free water Before the addition of E-PAP enzyme, 2.5 μL of the mixed reaction solution was pipetted for subsequent gel electrophoresis, then 4 μL of E-PAP enzyme was added into 96 μL of the reaction solution, reacted for 30 min at 37° C. 2.5 μL of the reaction solution after tailing was pipetted, and subjected to electrophoresis in 0.8% agarose gel with the reaction solution before tailing at 180 V for 10 min. After the bands were confirmed right, Cas9 mRNA was recovered with Rnasy Mini Kit (QIAGEN, 74104).

(2) In Vitro Transcription of sgRNA

The purified product obtained above was subjected to subsequent steps. In vitro transcription of sgRNA was conducted according to instructions of kit MEGA Shortscript™ T7 Transcription Kit (Invitrogen™, AM1354), 600 ng of template DNA was used for reaction, and the reaction solution was mixed as follows:

2 μL T7 10×Reaction Buffer
2 μL T7 ATP Solution (75 mM)
2 μL T7 CTP Solution (75 mM)
2 μL T7 GTP Solution (75 mM)
2 μL T7 UTP Solution (75 mM)
2 μL T7 Enzyme Mix
600 ng template PCR fragment of sgRNA
Add Nuclease-free water to 20 μL The reaction solution was reacted on a PCR thermal cycler after well mixed, and the cover-heating temperature was set as 50° C., the system temperature was set as 37° C. 1 μL of TURBO DNase digested template DNA was added after reacted for 6 h for digestion at 37° C. for 15 min. 1 μL of the mixed reaction solution was pipetted and subjected to electrophoresis in 0.8% agarose gel with a voltage of 180 V for 10 min. After the bands were confirmed right, mRNA of sgRNA was recovered with MEGAclear Kit (Invitrogen™, AM1908).

(3) Fertilized Eggs Injection and Embryo Transplantation

C57 female mice of 6-8 weeks old were taken for intraperitoneal injection of human chorionic gonadotropin, HCG (Ningbo Sansheng Pharm, B141002), and after 48 h, pregnant mare serum gonadotropin PMSG (Ningbo Sansheng Pharm, S141004) was injected intraperitoneally. The mice were caged together with C57 male mice of 7-8 weeks old. After 12 h, the mice were killed under anesthesia, and eggs were taken. The cells were separated when the fertilized eggs were developed to 2-cell stage, one of which was transferred to a zona pellucida of the other, and directly transferred to oviducts of pseudopregnant ICR female mice with other 20-25 fertilized eggs of ICR mice without injection.

CBE4max/CE-CBE$^{1048-1063}$/CE-A3A$^{1048-1063}$ (100 ng/μL) were mixed with mRNA of sgRNA (50 ng/μL) respectively, and centrifuged for 5 min at 12000 rpm. The mRNA supernatant was pipetted into droplets of HEPES-CZB medium containing 5 μg/mL of cytochalasin B and injected into the remaining cell cytoplasm using a FemtoJect micropipette. Next, the injected fertilized eggs were cultured to 2-cell stage, and transferred to oviducts of pseudopregnant ICR female mice with other 20-25 fertilized eggs of ICR mice.

Figure 14:
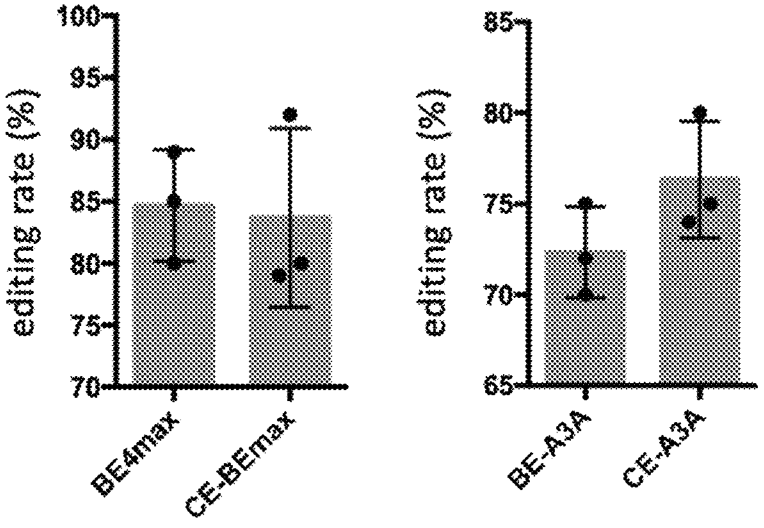
FIG. 14 is a schematic diagram of the present disclosure showing the results of on-target editing on DNA generated by BE4max, BE-A3A, CE-BE$^{1048-1063}$ and CE-A3A$^{1048-1063}$.
Figure 15:
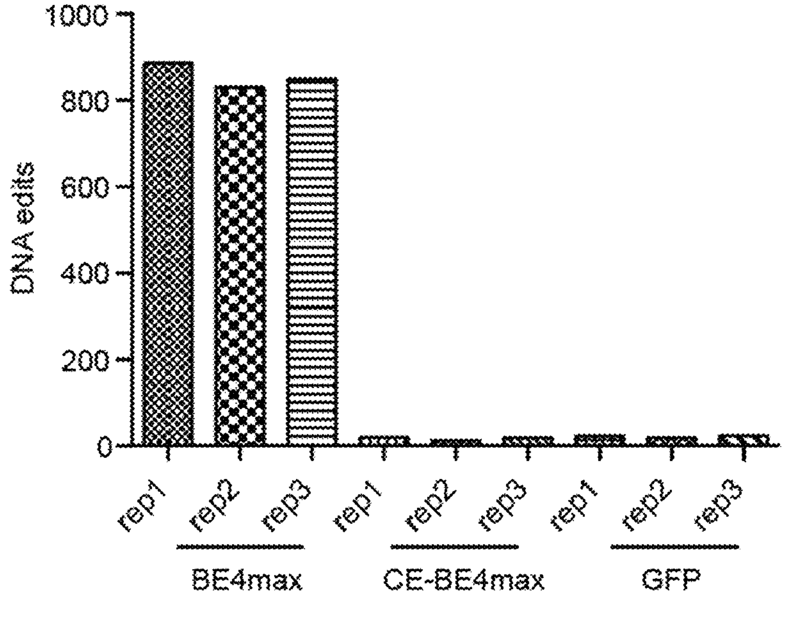
FIG. 15 is a schematic diagram of the present disclosure showing the results of off-target editing on DNA caused by BE4max and CE-BE$^{1048-1063}$ (CE-BE4max).
Figure 16:
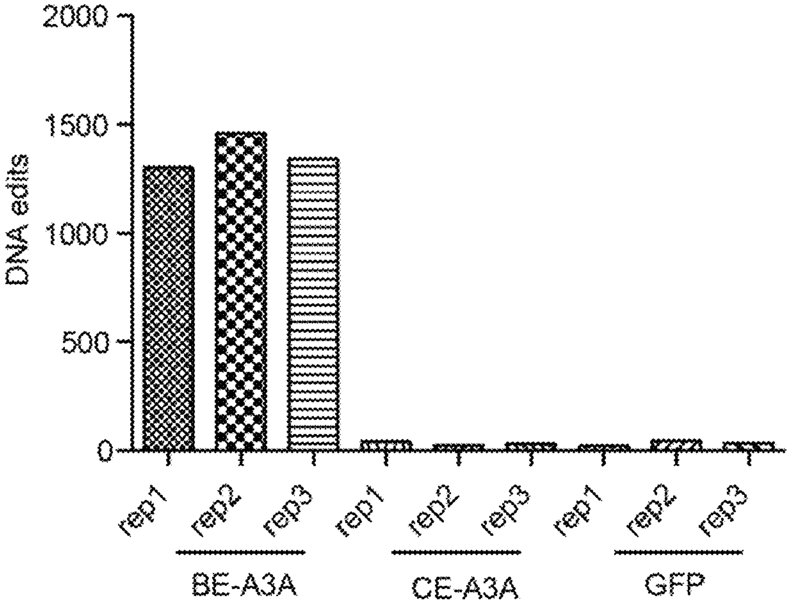
FIG. 16 is a schematic diagram of the present disclosure showing the results of off-target editing on DNA caused by BE-A3A and CE-A3A$^{1048-1063}$ (CE-A3A).

On day 13.5, the female mice were dissected, and the eye color of the mice was observed. C57 mice embryos were selected, lysed, and genomic DNA was extracted for subsequent detection. On-target efficiency of sgRNA was detected at first, and the editing efficiency was verified, the detailed results are shown in FIG. 14. Subsequently, WGS sequencing was conducted on genomic DNA respectively for analyzing the off-targeting of the editor on DNA, and the detailed results are shown in FIG. 15 and FIG. 16. It can be seen that CE-CBE$^{1048-1063}$ and CE-A3A$^{1048-1063}$ have better editing efficiency and lower off-target rate in mice embryos.

In conclusion, the present disclosure overcomes various shortcomings in the prior art, thereby has a high industrial value.

The present disclosure is not to be limited by the examples described which are intended as an example illustration of the principle and efficacy of the present disclosure. It will be apparent to those skilled in the art that various modifications and variations can be made to the examples described above in the present disclosure without departing from the spirit or scope of the disclosure. Therefore, all equivalent modifications or changes made by those with ordinary knowledge in the art without departing from the spirit and technical ideas disclosed in the present invention should still be covered by the claims of the present invention.

What is claimed is:

1. A fusion protein comprising a first nCas9 fragment, a chimeric insertion fragment, a second nCas9 fragment and two UGI fragments from N-terminus to C-terminus, wherein the chimeric insertion fragment is selected from an APOBEC1 fragment or an APOBEC3A fragment;

wherein the first nCas9 fragment has the amino acid sequence comprising the amino acid sequence of SEQ ID NO: 1, and the second nCas9 fragment has the amino acid sequence comprising an amino acid sequence of SEQ ID NO: 2.

2. The fusion protein of claim 1, wherein the APOBEC1 fragment has the amino acid sequence comprising:

the amino acid sequence of SEQ ID NO: 3; or, the amino acid sequence having at least 80% sequence identity to SEQ ID NO: 3 and retaining the function of cytosine deaminase activity.

3. The fusion protein of claim 1, wherein the APOBEC3A fragment has the amino acid sequence comprising:

the amino acid sequence of SEQ ID NO: 4; or, the amino acid sequence having at least 80% sequence identity to SEQ ID NO: 4 and retaining the function of cytosine deaminase activity.

4. The fusion protein of claim 1, wherein the amino acid of the UGI fragment comprises:

the amino acid sequence of SEQ ID NO: 5; or, the amino acid sequence having at least 80% sequence identity to SEQ ID NO: 5 and retaining the function of the activity of inhibiting the glycosylation of uracil DNA.

5. The fusion protein of claim 1, wherein the APOBEC1 fragment has the amino acid sequence comprising an amino acid sequence of SEQ ID NO: 3;

the APOBEC3A fragment has the amino acid sequence comprising an amino acid sequence of SEQ ID NO: 4;

the amino acid of the UGI fragment comprises the amino acid sequence of SEQ ID NO: 5.

6. The fusion protein of claim 1, wherein the fusion protein further comprises a nuclear localization signal fragment.

7. The fusion protein of claim 6, wherein the nuclear localization signal fragment comprises the amino acid sequence of SEQ ID NO: 6.

8. The fusion protein of claim 1, wherein the fusion protein further comprises a flexible linker peptide fragment.

9. The fusion protein of claim 8, wherein the flexible linker peptide fragment comprises the amino acid sequence of SEQ ID NO: 7 or SEQ ID NO: 8.

10. The fusion protein of claim 1, wherein the fusion protein has the amino acid as shown in SEQ ID NO: 9 or 10.

11. An isolated polynucleotide encoding the fusion protein of claim 1.

12. A construct comprising the isolated polynucleotide of claim 11.

13. An expression system comprising the construct of claim 12 or having the polynucleotide of claim 11 integrated into its genome.

14. The expression system of claim 13, wherein the host cell of the expression system is selected from eukaryotic cells or prokaryotic cells.

15. A base editing system comprising the fusion protein of claim 1, wherein the base editing system further comprises sgRNA.

16. A method for gene editing comprising introducing the fusion protein of claim 1 or a polynucleotide encoding the fusion protein in a cell; and incubating the cell to express the fusion protein;

wherein the expressed fusion protein edits a target region within a gene in the presence of an sgRNA.

17. A method for gene editing comprising introducing the fusion protein of claim 1 or a polynucleotide encoding the fusion protein in a cell;

incubating the cell to express the fusion protein; and introducing an sgRNA or a polynucleotide encoding the sgRNA to the cell;

wherein the sgRNA targets a specific site of a gene and wherein the expressed fusion protein edits a target region within the gene.

* * * * *

```
                        SEQUENCE LISTING


<160> NUMBER OF SEQ ID NOS: 134

<210> SEQ ID NO 1
<211> LENGTH: 1046
<212> TYPE: PRT
<213> ORGANISM: Artificial Sequence
<220> FEATURE:
<223> OTHER INFORMATION: The first nCas9 fragment

<400> SEQUENCE: 1

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335
```

-continued

```
Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750
```

-continued

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys
    1040                1045

<210> SEQ ID NO 2
<211> LENGTH: 305
<212> TYPE: PRT
<213> ORGANISM: Artificial Sequence
<220> FEATURE:
<223> OTHER INFORMATION: The second nCas9 fragment

<400> SEQUENCE: 2

Glu Thr Asn Gly Glu Thr Gly Glu Ile Val Trp Asp Lys Gly Arg Asp
1               5                   10                  15

Phe Ala Thr Val Arg Lys Val Leu Ser Met Pro Gln Val Asn Ile Val
            20                  25                  30

Lys Lys Thr Glu Val Gln Thr Gly Gly Phe Ser Lys Glu Ser Ile Leu
        35                  40                  45

Pro Lys Arg Asn Ser Asp Lys Leu Ile Ala Arg Lys Lys Asp Trp Asp
    50                  55                  60

-continued

```
Pro Lys Lys Tyr Gly Gly Phe Asp Ser Pro Thr Val Ala Tyr Ser Val
65                  70                  75                  80

Leu Val Val Ala Lys Val Glu Lys Gly Lys Ser Lys Lys Leu Lys Ser
                85                  90                  95

Val Lys Glu Leu Leu Gly Ile Thr Ile Met Glu Arg Ser Ser Phe Glu
            100                 105                 110

Lys Asn Pro Ile Asp Phe Leu Glu Ala Lys Gly Tyr Lys Glu Val Lys
        115                 120                 125

Lys Asp Leu Ile Ile Lys Leu Pro Lys Tyr Ser Leu Phe Glu Leu Glu
    130                 135                 140

Asn Gly Arg Lys Arg Met Leu Ala Ser Ala Gly Glu Leu Gln Lys Gly
145                 150                 155                 160

Asn Glu Leu Ala Leu Pro Ser Lys Tyr Val Asn Phe Leu Tyr Leu Ala
                165                 170                 175

Ser His Tyr Glu Lys Leu Lys Gly Ser Pro Glu Asp Asn Glu Gln Lys
            180                 185                 190

Gln Leu Phe Val Glu Gln His Lys His Tyr Leu Asp Glu Ile Ile Glu
        195                 200                 205

Gln Ile Ser Glu Phe Ser Lys Arg Val Ile Leu Ala Asp Ala Asn Leu
    210                 215                 220

Asp Lys Val Leu Ser Ala Tyr Asn Lys His Arg Asp Lys Pro Ile Arg
225                 230                 235                 240

Glu Gln Ala Glu Asn Ile Ile His Leu Phe Thr Leu Thr Asn Leu Gly
                245                 250                 255

Ala Pro Ala Ala Phe Lys Tyr Phe Asp Thr Thr Ile Asp Arg Lys Arg
            260                 265                 270

Tyr Thr Ser Thr Lys Glu Val Leu Asp Ala Thr Leu Ile His Gln Ser
        275                 280                 285

Ile Thr Gly Leu Tyr Glu Thr Arg Ile Asp Leu Ser Gln Leu Gly Gly
    290                 295                 300

Asp
305
```

<210> SEQ ID NO 3
<211> LENGTH: 262
<212> TYPE: PRT
<213> ORGANISM: Artificial Sequence
<220> FEATURE:
<223> OTHER INFORMATION: The APOBEC1 fragment

<400> SEQUENCE: 3

```
Ser Gly Ser Glu Thr Pro Gly Thr Ser Glu Ser Ala Thr Pro Glu Ser
1               5                   10                  15

Gly Ser Glu Thr Gly Pro Val Ala Val Asp Pro Thr Leu Arg Arg Arg
            20                  25                  30

Ile Glu Pro His Glu Phe Glu Val Phe Phe Asp Pro Arg Glu Leu Arg
        35                  40                  45

Lys Glu Thr Cys Leu Leu Tyr Glu Ile Lys Trp Gly Thr Ser His Lys
    50                  55                  60

Ile Trp Arg His Ser Ser Lys Asn Thr Thr Lys His Val Glu Val Asn
65                  70                  75                  80

Phe Ile Glu Lys Phe Thr Ser Glu Arg His Phe Cys Pro Ser Thr Ser
                85                  90                  95

Cys Ser Ile Thr Trp Phe Leu Ser Trp Ser Pro Cys Gly Glu Cys Ser
            100                 105                 110
```

-continued

```
Lys Ala Ile Thr Glu Phe Leu Ser Gln His Pro Asn Val Thr Leu Val
        115                 120                 125

Ile Tyr Val Ala Arg Leu Tyr His His Met Asp Gln Gln Asn Arg Gln
    130                 135                 140

Gly Leu Arg Asp Leu Val Asn Ser Gly Val Thr Ile Gln Ile Met Thr
145                 150                 155                 160

Ala Pro Glu Tyr Asp Tyr Cys Trp Arg Asn Phe Val Asn Tyr Pro Pro
                165                 170                 175

Gly Lys Glu Ala His Trp Pro Arg Tyr Pro Pro Leu Trp Met Lys Leu
            180                 185                 190

Tyr Ala Leu Glu Leu His Ala Gly Ile Leu Gly Leu Pro Pro Cys Leu
        195                 200                 205

Asn Ile Leu Arg Arg Lys Gln Pro Gln Leu Thr Phe Phe Thr Ile Ala
    210                 215                 220

Leu Gln Ser Cys His Tyr Gln Arg Leu Pro Pro His Ile Leu Trp Ala
225                 230                 235                 240

Thr Gly Leu Lys Ser Gly Ser Gly Ser Glu Thr Pro Gly Thr Ser Glu
                245                 250                 255

Ser Ala Thr Pro Glu Ser
            260


<210> SEQ ID NO 4
<211> LENGTH: 239
<212> TYPE: PRT
<213> ORGANISM: Artificial Sequence
<220> FEATURE:
<223> OTHER INFORMATION: The APOBEC3A fragment

<400> SEQUENCE: 4

Ser Gly Ser Glu Thr Pro Gly Thr Ser Glu Ser Ala Thr Pro Glu Ser
1               5                   10                  15

Gly Ser Met Glu Ala Ser Pro Ala Ser Gly Pro Arg His Leu Met Asp
            20                  25                  30

Pro His Ile Phe Thr Ser Asn Phe Asn Asn Gly Ile Gly Arg His Lys
        35                  40                  45

Thr Tyr Leu Cys Tyr Glu Val Glu Arg Leu Asp Asn Gly Thr Ser Val
    50                  55                  60

Lys Met Asp Gln His Arg Gly Phe Leu His Asn Gln Ala Lys Asn Leu
65                  70                  75                  80

Leu Cys Gly Phe Tyr Gly Arg His Ala Glu Leu Arg Phe Leu Asp Leu
                85                  90                  95

Val Pro Ser Leu Gln Leu Asp Pro Ala Gln Ile Tyr Arg Val Thr Trp
            100                 105                 110

Phe Ile Ser Trp Ser Pro Cys Phe Ser Trp Gly Cys Ala Gly Glu Val
        115                 120                 125

Arg Ala Phe Leu Gln Glu Asn Thr His Val Arg Leu Arg Ile Phe Ala
    130                 135                 140

Ala Arg Ile Tyr Tyr Tyr Asp Pro Leu Tyr Lys Glu Ala Leu Gln Met
145                 150                 155                 160

Leu Arg Asp Ala Gly Ala Gln Val Ser Ile Met Thr Tyr Asp Glu Phe
                165                 170                 175

Lys His Cys Trp Asp Thr Phe Val Asp His Gln Gly Cys Pro Phe Gln
            180                 185                 190

Pro Trp Asp Gly Leu Asp Glu His Ser Gln Ala Leu Ser Gly Arg Leu
        195                 200                 205
```

-continued

```
Arg Ala Ile Leu Gln Asn Gln Gly Asn Ser Gly Ser Glu Ser Gly Ser
    210                 215                 220

Gly Ser Glu Thr Pro Gly Thr Ser Glu Ser Ala Thr Pro Glu Ser
225                 230                 235


<210> SEQ ID NO 5
<211> LENGTH: 83
<212> TYPE: PRT
<213> ORGANISM: Artificial Sequence
<220> FEATURE:
<223> OTHER INFORMATION: The UGI fragment

<400> SEQUENCE: 5

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu


<210> SEQ ID NO 6
<211> LENGTH: 18
<212> TYPE: PRT
<213> ORGANISM: Artificial Sequence
<220> FEATURE:
<223> OTHER INFORMATION: The nuclear localization signal fragment

<400> SEQUENCE: 6

Lys Arg Thr Ala Asp Gly Ser Glu Phe Glu Ser Pro Lys Lys Lys Arg
1               5                   10                  15

Lys Val


<210> SEQ ID NO 7
<211> LENGTH: 16
<212> TYPE: PRT
<213> ORGANISM: Artificial Sequence
<220> FEATURE:
<223> OTHER INFORMATION: The flexible linker peptide fragment

<400> SEQUENCE: 7

Ser Gly Ser Glu Thr Pro Gly Thr Ser Glu Ser Ala Thr Pro Glu Ser
1               5                   10                  15


<210> SEQ ID NO 8
<211> LENGTH: 10
<212> TYPE: PRT
<213> ORGANISM: Artificial Sequence
<220> FEATURE:
<223> OTHER INFORMATION: The flexible linker peptide fragment

<400> SEQUENCE: 8

Ser Gly Gly Ser Gly Gly Ser Gly Gly Ser
1               5                   10


<210> SEQ ID NO 9
<211> LENGTH: 1840
<212> TYPE: PRT
<213> ORGANISM: Artificial Sequence
```

-continued

<220> FEATURE:
<223> OTHER INFORMATION: The fusion protein

<400> SEQUENCE: 9

```
Lys Arg Thr Ala Asp Gly Ser Glu Phe Glu Ser Pro Lys Lys Lys Arg
1               5                   10                  15

Lys Val Ser Ser Asp Lys Lys Tyr Ser Ile Gly Leu Ala Ile Gly Thr
            20                  25                  30

Asn Ser Val Gly Trp Ala Val Ile Thr Asp Glu Tyr Lys Val Pro Ser
        35                  40                  45

Lys Lys Phe Lys Val Leu Gly Asn Thr Asp Arg His Ser Ile Lys Lys
    50                  55                  60

Asn Leu Ile Gly Ala Leu Leu Phe Asp Ser Gly Glu Thr Ala Glu Ala
65                  70                  75                  80

Thr Arg Leu Lys Arg Thr Ala Arg Arg Arg Tyr Thr Arg Arg Lys Asn
                85                  90                  95

Arg Ile Cys Tyr Leu Gln Glu Ile Phe Ser Asn Glu Met Ala Lys Val
            100                 105                 110

Asp Asp Ser Phe Phe His Arg Leu Glu Glu Ser Phe Leu Val Glu Glu
        115                 120                 125

Asp Lys Lys His Glu Arg His Pro Ile Phe Gly Asn Ile Val Asp Glu
    130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala
                165                 170                 175

Leu Ala His Met Ile Lys Phe Arg Gly His Phe Leu Ile Glu Gly Asp
            180                 185                 190

Leu Asn Pro Asp Asn Ser Asp Val Asp Lys Leu Phe Ile Gln Leu Val
        195                 200                 205

Gln Thr Tyr Asn Gln Leu Phe Glu Glu Asn Pro Ile Asn Ala Ser Gly
    210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
            260                 265                 270

Ser Asn Phe Asp Leu Ala Glu Asp Ala Lys Leu Gln Leu Ser Lys Asp
        275                 280                 285

Thr Tyr Asp Asp Asp Leu Asp Asn Leu Leu Ala Gln Ile Gly Asp Gln
    290                 295                 300

Tyr Ala Asp Leu Phe Leu Ala Ala Lys Asn Leu Ser Asp Ala Ile Leu
305                 310                 315                 320

Leu Ser Asp Ile Leu Arg Val Asn Thr Glu Ile Thr Lys Ala Pro Leu
                325                 330                 335

Ser Ala Ser Met Ile Lys Arg Tyr Asp Glu His His Gln Asp Leu Thr
            340                 345                 350

Leu Leu Lys Ala Leu Val Arg Gln Gln Leu Pro Glu Lys Tyr Lys Glu
        355                 360                 365

Ile Phe Phe Asp Gln Ser Lys Asn Gly Tyr Ala Gly Tyr Ile Asp Gly
    370                 375                 380

Gly Ala Ser Gln Glu Glu Phe Tyr Lys Phe Ile Lys Pro Ile Leu Glu
385                 390                 395                 400
```

-continued

```
Lys Met Asp Gly Thr Glu Glu Leu Leu Val Lys Leu Asn Arg Glu Asp
                405                 410                 415

Leu Leu Arg Lys Gln Arg Thr Phe Asp Asn Gly Ser Ile Pro His Gln
            420                 425                 430

Ile His Leu Gly Glu Leu His Ala Ile Leu Arg Arg Gln Glu Asp Phe
        435                 440                 445

Tyr Pro Phe Leu Lys Asp Asn Arg Glu Lys Ile Glu Lys Ile Leu Thr
    450                 455                 460

Phe Arg Ile Pro Tyr Tyr Val Gly Pro Leu Ala Arg Gly Asn Ser Arg
465                 470                 475                 480

Phe Ala Trp Met Thr Arg Lys Ser Glu Glu Thr Ile Thr Pro Trp Asn
                485                 490                 495

Phe Glu Glu Val Val Asp Lys Gly Ala Ser Ala Gln Ser Phe Ile Glu
            500                 505                 510

Arg Met Thr Asn Phe Asp Lys Asn Leu Pro Asn Glu Lys Val Leu Pro
        515                 520                 525

Lys His Ser Leu Leu Tyr Glu Tyr Phe Thr Val Tyr Asn Glu Leu Thr
    530                 535                 540

Lys Val Lys Tyr Val Thr Glu Gly Met Arg Lys Pro Ala Phe Leu Ser
545                 550                 555                 560

Gly Glu Gln Lys Lys Ala Ile Val Asp Leu Leu Phe Lys Thr Asn Arg
                565                 570                 575

Lys Val Thr Val Lys Gln Leu Lys Glu Asp Tyr Phe Lys Lys Ile Glu
            580                 585                 590

Cys Phe Asp Ser Val Glu Ile Ser Gly Val Glu Asp Arg Phe Asn Ala
        595                 600                 605

Ser Leu Gly Thr Tyr His Asp Leu Leu Lys Ile Ile Lys Asp Lys Asp
    610                 615                 620

Phe Leu Asp Asn Glu Glu Asn Glu Asp Ile Leu Glu Asp Ile Val Leu
625                 630                 635                 640

Thr Leu Thr Leu Phe Glu Asp Arg Glu Met Ile Glu Glu Arg Leu Lys
                645                 650                 655

Thr Tyr Ala His Leu Phe Asp Asp Lys Val Met Lys Gln Leu Lys Arg
            660                 665                 670

Arg Arg Tyr Thr Gly Trp Gly Arg Leu Ser Arg Lys Leu Ile Asn Gly
        675                 680                 685

Ile Arg Asp Lys Gln Ser Gly Lys Thr Ile Leu Asp Phe Leu Lys Ser
    690                 695                 700

Asp Gly Phe Ala Asn Arg Asn Phe Met Gln Leu Ile His Asp Asp Ser
705                 710                 715                 720

Leu Thr Phe Lys Glu Asp Ile Gln Lys Ala Gln Val Ser Gly Gln Gly
                725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Val Asp Glu Leu Val Lys
        755                 760                 765

Val Met Gly Arg His Lys Pro Glu Asn Ile Val Ile Glu Met Ala Arg
    770                 775                 780

Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
                805                 810                 815
```

-continued

```
Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
        835                 840                 845

Ile Asn Arg Leu Ser Asp Tyr Asp Val Asp His Ile Val Pro Gln Ser
    850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
                885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
        915                 920                 925

Glu Leu Asp Lys Ala Gly Phe Ile Lys Arg Gln Leu Val Glu Thr Arg
    930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
                965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr  His His Ala His Asp  Ala Tyr Leu
        995                 1000                1005

Asn Ala  Val Val Gly Thr Ala  Leu Ile Lys Lys Tyr  Pro Lys Leu
    1010                 1015                1020

Glu Ser  Glu Phe Val Tyr Gly  Asp Tyr Lys Val Tyr  Asp Val Arg
    1025                 1030                1035

Lys Met  Ile Ala Lys Ser Glu  Gln Glu Ile Gly Lys  Ala Thr Ala
    1040                 1045                1050

Lys Tyr  Phe Phe Tyr Ser Asn  Ile Met Asn Phe Phe  Lys Ser Gly
    1055                 1060                1065

Ser Glu  Thr Pro Gly Thr Ser  Glu Ser Ala Thr Pro  Glu Ser Gly
    1070                 1075                1080

Ser Glu  Thr Gly Pro Val Ala  Val Asp Pro Thr Leu  Arg Arg Arg
    1085                 1090                1095

Ile Glu  Pro His Glu Phe Glu  Val Phe Phe Asp Pro  Arg Glu Leu
    1100                 1105                1110

Arg Lys  Glu Thr Cys Leu Leu  Tyr Glu Ile Lys Trp  Gly Thr Ser
    1115                 1120                1125

His Lys  Ile Trp Arg His Ser  Ser Lys Asn Thr Thr  Lys His Val
    1130                 1135                1140

Glu Val  Asn Phe Ile Glu Lys  Phe Thr Ser Glu Arg  His Phe Cys
    1145                 1150                1155

Pro Ser  Thr Ser Cys Ser Ile  Thr Trp Phe Leu Ser  Trp Ser Pro
    1160                 1165                1170

Cys Gly  Glu Cys Ser Lys Ala  Ile Thr Glu Phe Leu  Ser Gln His
    1175                 1180                1185

Pro Asn  Val Thr Leu Val Ile  Tyr Val Ala Arg Leu  Tyr His His
    1190                 1195                1200

Met Asp  Gln Gln Asn Arg Gln  Gly Leu Arg Asp Leu  Val Asn Ser
    1205                 1210                1215

Gly Val  Thr Ile Gln Ile Met  Thr Ala Pro Glu Tyr  Asp Tyr Cys
```

-continued

```
    1220                1225                1230

Trp Arg  Asn Phe Val Asn Tyr  Pro Pro Gly Lys Glu  Ala His Trp
    1235                1240                1245

Pro Arg  Tyr Pro Pro Leu Trp  Met Lys Leu Tyr Ala  Leu Glu Leu
    1250                1255                1260

His Ala  Gly Ile Leu Gly Leu  Pro Pro Cys Leu Asn  Ile Leu Arg
    1265                1270                1275

Arg Lys  Gln Pro Gln Leu Thr  Phe Phe Thr Ile Ala  Leu Gln Ser
    1280                1285                1290

Cys His  Tyr Gln Arg Leu Pro  Pro His Ile Leu Trp  Ala Thr Gly
    1295                1300                1305

Leu Lys  Ser Gly Ser Gly Ser  Glu Thr Pro Gly Thr  Ser Glu Ser
    1310                1315                1320

Ala Thr  Pro Glu Ser Glu Thr  Asn Gly Glu Thr Gly  Glu Ile Val
    1325                1330                1335

Trp Asp  Lys Gly Arg Asp Phe  Ala Thr Val Arg Lys  Val Leu Ser
    1340                1345                1350

Met Pro  Gln Val Asn Ile Val  Lys Lys Thr Glu Val  Gln Thr Gly
    1355                1360                1365

Gly Phe  Ser Lys Glu Ser Ile  Leu Pro Lys Arg Asn  Ser Asp Lys
    1370                1375                1380

Leu Ile  Ala Arg Lys Lys Asp  Trp Asp Pro Lys Lys  Tyr Gly Gly
    1385                1390                1395

Phe Asp  Ser Pro Thr Val Ala  Tyr Ser Val Leu Val  Val Ala Lys
    1400                1405                1410

Val Glu  Lys Gly Lys Ser Lys  Lys Leu Lys Ser Val  Lys Glu Leu
    1415                1420                1425

Leu Gly  Ile Thr Ile Met Glu  Arg Ser Ser Phe Glu  Lys Asn Pro
    1430                1435                1440

Ile Asp  Phe Leu Glu Ala Lys  Gly Tyr Lys Glu Val  Lys Lys Asp
    1445                1450                1455

Leu Ile  Ile Lys Leu Pro Lys  Tyr Ser Leu Phe Glu  Leu Glu Asn
    1460                1465                1470

Gly Arg  Lys Arg Met Leu Ala  Ser Ala Gly Glu Leu  Gln Lys Gly
    1475                1480                1485

Asn Glu  Leu Ala Leu Pro Ser  Lys Tyr Val Asn Phe  Leu Tyr Leu
    1490                1495                1500

Ala Ser  His Tyr Glu Lys Leu  Lys Gly Ser Pro Glu  Asp Asn Glu
    1505                1510                1515

Gln Lys  Gln Leu Phe Val Glu  Gln His Lys His Tyr  Leu Asp Glu
    1520                1525                1530

Ile Ile  Glu Gln Ile Ser Glu  Phe Ser Lys Arg Val  Ile Leu Ala
    1535                1540                1545

Asp Ala  Asn Leu Asp Lys Val  Leu Ser Ala Tyr Asn  Lys His Arg
    1550                1555                1560

Asp Lys  Pro Ile Arg Glu Gln  Ala Glu Asn Ile Ile  His Leu Phe
    1565                1570                1575

Thr Leu  Thr Asn Leu Gly Ala  Pro Ala Ala Phe Lys  Tyr Phe Asp
    1580                1585                1590

Thr Thr  Ile Asp Arg Lys Arg  Tyr Thr Ser Thr Lys  Glu Val Leu
    1595                1600                1605

Asp Ala  Thr Leu Ile His Gln  Ser Ile Thr Gly Leu  Tyr Glu Thr
    1610                1615                1620
```

Arg Ile Asp Leu Ser Gln Leu Gly Gly Asp Ser Gly Gly Ser Gly
1625 1630 1635

Gly Ser Gly Gly Ser Thr Asn Leu Ser Asp Ile Ile Glu Lys Glu
1640 1645 1650

Thr Gly Lys Gln Leu Val Ile Gln Glu Ser Ile Leu Met Leu Pro
1655 1660 1665

Glu Glu Val Glu Glu Val Ile Gly Asn Lys Pro Glu Ser Asp Ile
1670 1675 1680

Leu Val His Thr Ala Tyr Asp Glu Ser Thr Asp Glu Asn Val Met
1685 1690 1695

Leu Leu Thr Ser Asp Ala Pro Glu Tyr Lys Pro Trp Ala Leu Val
1700 1705 1710

Ile Gln Asp Ser Asn Gly Glu Asn Lys Ile Lys Met Leu Ser Gly
1715 1720 1725

Gly Ser Gly Gly Ser Gly Gly Ser Thr Asn Leu Ser Asp Ile Ile
1730 1735 1740

Glu Lys Glu Thr Gly Lys Gln Leu Val Ile Gln Glu Ser Ile Leu
1745 1750 1755

Met Leu Pro Glu Glu Val Glu Glu Val Ile Gly Asn Lys Pro Glu
1760 1765 1770

Ser Asp Ile Leu Val His Thr Ala Tyr Asp Glu Ser Thr Asp Glu
1775 1780 1785

Asn Val Met Leu Leu Thr Ser Asp Ala Pro Glu Tyr Lys Pro Trp
1790 1795 1800

Ala Leu Val Ile Gln Asp Ser Asn Gly Glu Asn Lys Ile Lys Met
1805 1810 1815

Leu Ser Gly Gly Ser Lys Arg Thr Ala Asp Gly Ser Glu Phe Glu
1820 1825 1830

Pro Lys Lys Lys Arg Lys Val
1835 1840

<210> SEQ ID NO 10
<211> LENGTH: 1817
<212> TYPE: PRT
<213> ORGANISM: Artificial Sequence
<220> FEATURE:
<223> OTHER INFORMATION: The fusion protein

<400> SEQUENCE: 10

Lys Arg Thr Ala Asp Gly Ser Glu Phe Glu Ser Pro Lys Lys Lys Arg
1 5 10 15

Lys Val Ser Ser Asp Lys Lys Tyr Ser Ile Gly Leu Ala Ile Gly Thr
20 25 30

Asn Ser Val Gly Trp Ala Val Ile Thr Asp Glu Tyr Lys Val Pro Ser
35 40 45

Lys Lys Phe Lys Val Leu Gly Asn Thr Asp Arg His Ser Ile Lys Lys
50 55 60

Asn Leu Ile Gly Ala Leu Leu Phe Asp Ser Gly Glu Thr Ala Glu Ala
65 70 75 80

Thr Arg Leu Lys Arg Thr Ala Arg Arg Arg Tyr Thr Arg Arg Lys Asn
85 90 95

Arg Ile Cys Tyr Leu Gln Glu Ile Phe Ser Asn Glu Met Ala Lys Val
100 105 110

Asp Asp Ser Phe Phe His Arg Leu Glu Glu Ser Phe Leu Val Glu Glu
115 120 125

-continued

```
Asp Lys Lys His Glu Arg His Pro Ile Phe Gly Asn Ile Val Asp Glu
    130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala
                165                 170                 175

Leu Ala His Met Ile Lys Phe Arg Gly His Phe Leu Ile Glu Gly Asp
            180                 185                 190

Leu Asn Pro Asp Asn Ser Asp Val Asp Lys Leu Phe Ile Gln Leu Val
        195                 200                 205

Gln Thr Tyr Asn Gln Leu Phe Glu Glu Asn Pro Ile Asn Ala Ser Gly
    210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
            260                 265                 270

Ser Asn Phe Asp Leu Ala Glu Asp Ala Lys Leu Gln Leu Ser Lys Asp
        275                 280                 285

Thr Tyr Asp Asp Asp Leu Asp Asn Leu Leu Ala Gln Ile Gly Asp Gln
    290                 295                 300

Tyr Ala Asp Leu Phe Leu Ala Ala Lys Asn Leu Ser Asp Ala Ile Leu
305                 310                 315                 320

Leu Ser Asp Ile Leu Arg Val Asn Thr Glu Ile Thr Lys Ala Pro Leu
                325                 330                 335

Ser Ala Ser Met Ile Lys Arg Tyr Asp Glu His His Gln Asp Leu Thr
            340                 345                 350

Leu Leu Lys Ala Leu Val Arg Gln Gln Leu Pro Glu Lys Tyr Lys Glu
        355                 360                 365

Ile Phe Phe Asp Gln Ser Lys Asn Gly Tyr Ala Gly Tyr Ile Asp Gly
    370                 375                 380

Gly Ala Ser Gln Glu Glu Phe Tyr Lys Phe Ile Lys Pro Ile Leu Glu
385                 390                 395                 400

Lys Met Asp Gly Thr Glu Glu Leu Leu Val Lys Leu Asn Arg Glu Asp
                405                 410                 415

Leu Leu Arg Lys Gln Arg Thr Phe Asp Asn Gly Ser Ile Pro His Gln
            420                 425                 430

Ile His Leu Gly Glu Leu His Ala Ile Leu Arg Arg Gln Glu Asp Phe
        435                 440                 445

Tyr Pro Phe Leu Lys Asp Asn Arg Glu Lys Ile Glu Lys Ile Leu Thr
    450                 455                 460

Phe Arg Ile Pro Tyr Tyr Val Gly Pro Leu Ala Arg Gly Asn Ser Arg
465                 470                 475                 480

Phe Ala Trp Met Thr Arg Lys Ser Glu Glu Thr Ile Thr Pro Trp Asn
                485                 490                 495

Phe Glu Glu Val Val Asp Lys Gly Ala Ser Ala Gln Ser Phe Ile Glu
            500                 505                 510

Arg Met Thr Asn Phe Asp Lys Asn Leu Pro Asn Glu Lys Val Leu Pro
        515                 520                 525

Lys His Ser Leu Leu Tyr Glu Tyr Phe Thr Val Tyr Asn Glu Leu Thr
    530                 535                 540
```

```
Lys Val Lys Tyr Val Thr Glu Gly Met Arg Lys Pro Ala Phe Leu Ser
545                 550                 555                 560

Gly Glu Gln Lys Lys Ala Ile Val Asp Leu Leu Phe Lys Thr Asn Arg
                565                 570                 575

Lys Val Thr Val Lys Gln Leu Lys Glu Asp Tyr Phe Lys Lys Ile Glu
            580                 585                 590

Cys Phe Asp Ser Val Glu Ile Ser Gly Val Glu Asp Arg Phe Asn Ala
        595                 600                 605

Ser Leu Gly Thr Tyr His Asp Leu Leu Lys Ile Ile Lys Asp Lys Asp
    610                 615                 620

Phe Leu Asp Asn Glu Glu Asn Glu Asp Ile Leu Glu Asp Ile Val Leu
625                 630                 635                 640

Thr Leu Thr Leu Phe Glu Asp Arg Glu Met Ile Glu Glu Arg Leu Lys
                645                 650                 655

Thr Tyr Ala His Leu Phe Asp Asp Lys Val Met Lys Gln Leu Lys Arg
            660                 665                 670

Arg Arg Tyr Thr Gly Trp Gly Arg Leu Ser Arg Lys Leu Ile Asn Gly
        675                 680                 685

Ile Arg Asp Lys Gln Ser Gly Lys Thr Ile Leu Asp Phe Leu Lys Ser
    690                 695                 700

Asp Gly Phe Ala Asn Arg Asn Phe Met Gln Leu Ile His Asp Asp Ser
705                 710                 715                 720

Leu Thr Phe Lys Glu Asp Ile Gln Lys Ala Gln Val Ser Gly Gln Gly
                725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Val Asp Glu Leu Val Lys
        755                 760                 765

Val Met Gly Arg His Lys Pro Glu Asn Ile Val Ile Glu Met Ala Arg
    770                 775                 780

Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
                805                 810                 815

Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
        835                 840                 845

Ile Asn Arg Leu Ser Asp Tyr Asp Val Asp His Ile Val Pro Gln Ser
    850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
                885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
        915                 920                 925

Glu Leu Asp Lys Ala Gly Phe Ile Lys Arg Gln Leu Val Glu Thr Arg
    930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
```

```
            965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr  His His Ala His Asp  Ala Tyr Leu
        995                 1000                1005

Asn Ala  Val Val Gly Thr Ala  Leu Ile Lys Lys Tyr  Pro Lys Leu
    1010                1015                1020

Glu Ser  Glu Phe Val Tyr Gly  Asp Tyr Lys Val Tyr  Asp Val Arg
    1025                1030                1035

Lys Met  Ile Ala Lys Ser Glu  Gln Glu Ile Gly Lys  Ala Thr Ala
    1040                1045                1050

Lys Tyr  Phe Phe Tyr Ser Asn  Ile Met Asn Phe Phe  Lys Ser Gly
    1055                1060                1065

Ser Glu  Thr Pro Gly Thr Ser  Glu Ser Ala Thr Pro  Glu Ser Gly
    1070                1075                1080

Ser Met  Glu Ala Ser Pro Ala  Ser Gly Pro Arg His  Leu Met Asp
    1085                1090                1095

Pro His  Ile Phe Thr Ser Asn  Phe Asn Asn Gly Ile  Gly Arg His
    1100                1105                1110

Lys Thr  Tyr Leu Cys Tyr Glu  Val Glu Arg Leu Asp  Asn Gly Thr
    1115                1120                1125

Ser Val  Lys Met Asp Gln His  Arg Gly Phe Leu His  Asn Gln Ala
    1130                1135                1140

Lys Asn  Leu Leu Cys Gly Phe  Tyr Gly Arg His Ala  Glu Leu Arg
    1145                1150                1155

Phe Leu  Asp Leu Val Pro Ser  Leu Gln Leu Asp Pro  Ala Gln Ile
    1160                1165                1170

Tyr Arg  Val Thr Trp Phe Ile  Ser Trp Ser Pro Cys  Phe Ser Trp
    1175                1180                1185

Gly Cys  Ala Gly Glu Val Arg  Ala Phe Leu Gln Glu  Asn Thr His
    1190                1195                1200

Val Arg  Leu Arg Ile Phe Ala  Ala Arg Ile Tyr Tyr  Tyr Asp Pro
    1205                1210                1215

Leu Tyr  Lys Glu Ala Leu Gln  Met Leu Arg Asp Ala  Gly Ala Gln
    1220                1225                1230

Val Ser  Ile Met Thr Tyr Asp  Glu Phe Lys His Cys  Trp Asp Thr
    1235                1240                1245

Phe Val  Asp His Gln Gly Cys  Pro Phe Gln Pro Trp  Asp Gly Leu
    1250                1255                1260

Asp Glu  His Ser Gln Ala Leu  Ser Gly Arg Leu Arg  Ala Ile Leu
    1265                1270                1275

Gln Asn  Gln Gly Asn Ser Gly  Ser Glu Ser Gly Ser  Gly Ser Glu
    1280                1285                1290

Thr Pro  Gly Thr Ser Glu Ser  Ala Thr Pro Glu Ser  Glu Thr Asn
    1295                1300                1305

Gly Glu  Thr Gly Glu Ile Val  Trp Asp Lys Gly Arg  Asp Phe Ala
    1310                1315                1320

Thr Val  Arg Lys Val Leu Ser  Met Pro Gln Val Asn  Ile Val Lys
    1325                1330                1335

Lys Thr  Glu Val Gln Thr Gly  Gly Phe Ser Lys Glu  Ser Ile Leu
    1340                1345                1350

Pro Lys  Arg Asn Ser Asp Lys  Leu Ile Ala Arg Lys  Lys Asp Trp
    1355                1360                1365
```

-continued

```
Asp Pro  Lys Lys Tyr Gly Gly  Phe Asp Ser Pro Thr  Val Ala Tyr
    1370                 1375                 1380

Ser Val  Leu Val Val Ala Lys  Val Glu Lys Gly Lys  Ser Lys Lys
    1385                 1390                 1395

Leu Lys  Ser Val Lys Glu Leu  Leu Gly Ile Thr Ile  Met Glu Arg
    1400                 1405                 1410

Ser Ser  Phe Glu Lys Asn Pro  Ile Asp Phe Leu Glu  Ala Lys Gly
    1415                 1420                 1425

Tyr Lys  Glu Val Lys Lys Asp  Leu Ile Ile Lys Leu  Pro Lys Tyr
    1430                 1435                 1440

Ser Leu  Phe Glu Leu Glu Asn  Gly Arg Lys Arg Met  Leu Ala Ser
    1445                 1450                 1455

Ala Gly  Glu Leu Gln Lys Gly  Asn Glu Leu Ala Leu  Pro Ser Lys
    1460                 1465                 1470

Tyr Val  Asn Phe Leu Tyr Leu  Ala Ser His Tyr Glu  Lys Leu Lys
    1475                 1480                 1485

Gly Ser  Pro Glu Asp Asn Glu  Gln Lys Gln Leu Phe  Val Glu Gln
    1490                 1495                 1500

His Lys  His Tyr Leu Asp Glu  Ile Ile Glu Gln Ile  Ser Glu Phe
    1505                 1510                 1515

Ser Lys  Arg Val Ile Leu Ala  Asp Ala Asn Leu Asp  Lys Val Leu
    1520                 1525                 1530

Ser Ala  Tyr Asn Lys His Arg  Asp Lys Pro Ile Arg  Glu Gln Ala
    1535                 1540                 1545

Glu Asn  Ile Ile His Leu Phe  Thr Leu Thr Asn Leu  Gly Ala Pro
    1550                 1555                 1560

Ala Ala  Phe Lys Tyr Phe Asp  Thr Thr Ile Asp Arg  Lys Arg Tyr
    1565                 1570                 1575

Thr Ser  Thr Lys Glu Val Leu  Asp Ala Thr Leu Ile  His Gln Ser
    1580                 1585                 1590

Ile Thr  Gly Leu Tyr Glu Thr  Arg Ile Asp Leu Ser  Gln Leu Gly
    1595                 1600                 1605

Gly Asp  Ser Gly Gly Ser Gly  Gly Ser Gly Gly Ser  Thr Asn Leu
    1610                 1615                 1620

Ser Asp  Ile Ile Glu Lys Glu  Thr Gly Lys Gln Leu  Val Ile Gln
    1625                 1630                 1635

Glu Ser  Ile Leu Met Leu Pro  Glu Glu Val Glu Glu  Val Ile Gly
    1640                 1645                 1650

Asn Lys  Pro Glu Ser Asp Ile  Leu Val His Thr Ala  Tyr Asp Glu
    1655                 1660                 1665

Ser Thr  Asp Glu Asn Val Met  Leu Leu Thr Ser Asp  Ala Pro Glu
    1670                 1675                 1680

Tyr Lys  Pro Trp Ala Leu Val  Ile Gln Asp Ser Asn  Gly Glu Asn
    1685                 1690                 1695

Lys Ile  Lys Met Leu Ser Gly  Gly Ser Gly Gly Ser  Gly Gly Ser
    1700                 1705                 1710

Thr Asn  Leu Ser Asp Ile Ile  Glu Lys Glu Thr Gly  Lys Gln Leu
    1715                 1720                 1725

Val Ile  Gln Glu Ser Ile Leu  Met Leu Pro Glu Glu  Val Glu Glu
    1730                 1735                 1740

Val Ile  Gly Asn Lys Pro Glu  Ser Asp Ile Leu Val  His Thr Ala
    1745                 1750                 1755
```

-continued

```
Tyr Asp  Glu Ser Thr Asp Glu  Asn Val Met Leu Leu  Thr Ser Asp
    1760                1765                1770

Ala Pro  Glu Tyr Lys Pro Trp  Ala Leu Val Ile Gln  Asp Ser Asn
    1775                1780                1785

Gly Glu  Asn Lys Ile Lys Met  Leu Ser Gly Gly Ser  Lys Arg Thr
    1790                1795                1800

Ala Asp  Gly Ser Glu Phe Glu  Pro Lys Lys Lys Arg  Lys Val
    1805                1810                1815
```

<210> SEQ ID NO 11
<211> LENGTH: 1374
<212> TYPE: DNA
<213> ORGANISM: Artificial Sequence
<220> FEATURE:
<223> OTHER INFORMATION: Synthetic sequence of TadA-TadA* transposon

<400> SEQUENCE: 11

```
cggcgcacga aaaacgcgaa agcgtttcac gataaatgcg aaaactctgg aggatctagc     60
ggcggatcct ctggaagcga gacaccaggc acaagcgagt ccgccacacc agagagctcc    120
ggcggctcct ccggaggatc ctctgaggtg gagttttccc acgagtactg gatgagacat    180
gccctgaccc tggccaagag ggcatgggat gaaagagaag tccccgtggg cgccgtgctg    240
gtgcacaaca atagagtgat cggagaggga tggaacaggc caatcggccg ccacgaccct    300
accgcacacg cagagatcat ggcactgagg cagggaggcc tggtcatgca gaattaccgc    360
ctgatcgatg ccaccctgta tgtgacactg gagccatgcg tgatgtgcgc aggagcaatg    420
atccacagca ggatcggaag agtggtgttc ggagcacggg acgccaagac cggcgcagca    480
ggctccctga tggatgtgct gcaccacccc ggcatgaacc accgggtgga gatcacagag    540
ggaatcctgg cagacgagtg cgccgccctg ctgagcgatt tctttagaat gcggagacag    600
gagatcaagg cccagaagaa ggcacagagc tccaccgact ctggaggatc tagcggcgga    660
tcctctggaa gcgagacacc aggcacaagc gagtccgcca caccagagag ctccggcggc    720
tcctccggag gatcctctga ggtggagttt tcccacgagt actggatgag acatgccctg    780
accctggcca agagggcacg cgatgagagg gaggtgcctg tgggagccgt gctggtgctg    840
aacaatagag tgatcggcga gggctggaac agagccatcg gcctgcacga cccaacagcc    900
catgccgaaa ttatggccct gagacagggc ggcctggtca tgcagaacta cagactgatt    960
gacgccaccc tgtacgtgac attcgagcct tgcgtgatgt gcgccggcgc catgatccac   1020
tctaggatcg gccgcgtggt gtttggcgtg aggaacgcaa aaaccggcgc cgcaggctcc   1080
ctgatggacg tgctgcacta ccccggcatg aatcaccgcg tcgaaattac cgagggaatc   1140
ctggcagatg aatgtgccgc cctgctgtgc tatttctttc ggatgcctag acaggtgttc   1200
aatgctcaga agaaggccca gagctccacc gactccggag gatctagcgg aggctcctct   1260
ggctctgaga cacctggcac aagcgagagc gcaacacctg aaagcagcgg gggcagcagc   1320
ggggggtcag ttttcgcatt tatcgtgaaa cgctttcgcg tttttcgtgc gccg         1374
```

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence of site 1

<400> SEQUENCE: 12

```
gaacacaaag catagactgc ggg                                            23
```

<210> SEQ ID NO 13
<211> LENGTH: 23
<212> TYPE: DNA
<213> ORGANISM: Artificial Sequence
<220> FEATURE:
<223> OTHER INFORMATION: Synthetic sequence of site 2

<400> SEQUENCE: 13
tacagcttgt agtactcata ggg 23

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence of site 3

<400> SEQUENCE: 14
catatctcct aacttcaggt tgg 23

<210> SEQ ID NO 15
<211> LENGTH: 23
<212> TYPE: DNA
<213> ORGANISM: Artificial Sequence
<220> FEATURE:
<223> OTHER INFORMATION: Synthetic sequence of site 4

<400> SEQUENCE: 15
ggagtagggg ctcagcaggg cgg 23

<210> SEQ ID NO 16
<211> LENGTH: 23
<212> TYPE: DNA
<213> ORGANISM: Artificial Sequence
<220> FEATURE:
<223> OTHER INFORMATION: Synthetic sequence of site 5

<400> SEQUENCE: 16
gtatgaagac aataactata agg 23

<210> SEQ ID NO 17
<211> LENGTH: 23
<212> TYPE: DNA
<213> ORGANISM: Artificial Sequence
<220> FEATURE:
<223> OTHER INFORMATION: Synthetic sequence of site 6

<400> SEQUENCE: 17
ggaacagtgt gtagaggtgg ggg 23

<210> SEQ ID NO 18
<211> LENGTH: 23
<212> TYPE: DNA
<213> ORGANISM: Artificial Sequence
<220> FEATURE:
<223> OTHER INFORMATION: Synthetic sequence of site 7

<400> SEQUENCE: 18
ctgtatgggt cccggggcgc tgg 23

<210> SEQ ID NO 19
<211> LENGTH: 23
<212> TYPE: DNA
<213> ORGANISM: Artificial Sequence
<220> FEATURE:

<223> OTHER INFORMATION: Synthetic sequence of site 8

<400> SEQUENCE: 19
tgtgcacacg ctgcagagca tgg 23

<210> SEQ ID NO 20
<211> LENGTH: 23
<212> TYPE: DNA
<213> ORGANISM: Artificial Sequence
<220> FEATURE:
<223> OTHER INFORMATION: Synthetic sequence of site 9

<400> SEQUENCE: 20
gcgggacagc ccggaagtcc agg 23

<210> SEQ ID NO 21
<211> LENGTH: 23
<212> TYPE: DNA
<213> ORGANISM: Artificial Sequence
<220> FEATURE:
<223> OTHER INFORMATION: Synthetic sequence of site 10

<400> SEQUENCE: 21
attgatgtaa tggatgcagt ggg 23

<210> SEQ ID NO 22
<211> LENGTH: 23
<212> TYPE: DNA
<213> ORGANISM: Artificial Sequence
<220> FEATURE:
<223> OTHER INFORMATION: Synthetic sequence of site 11

<400> SEQUENCE: 22
gtttcagaat cgaagggtga agg 23

<210> SEQ ID NO 23
<211> LENGTH: 23
<212> TYPE: DNA
<213> ORGANISM: Artificial Sequence
<220> FEATURE:
<223> OTHER INFORMATION: Synthetic sequence of site 12

<400> SEQUENCE: 23
agacatattc ctcactacaa agg 23

<210> SEQ ID NO 24
<211> LENGTH: 23
<212> TYPE: DNA
<213> ORGANISM: Artificial Sequence
<220> FEATURE:
<223> OTHER INFORMATION: Synthetic sequence of site 13

<400> SEQUENCE: 24
ctttagcttg acatgcagcg cgg 23

<210> SEQ ID NO 25
<211> LENGTH: 23
<212> TYPE: DNA
<213> ORGANISM: Artificial Sequence
<220> FEATURE:
<223> OTHER INFORMATION: Synthetic sequence of site 14

<400> SEQUENCE: 25
agccaggtgg gcggttctct tgg 23

<210> SEQ ID NO 26
<211> LENGTH: 23
<212> TYPE: DNA
<213> ORGANISM: Artificial Sequence
<220> FEATURE:
<223> OTHER INFORMATION: Synthetic sequence of site 15

<400> SEQUENCE: 26
ccccacagga agtggccatg cgc 23

<210> SEQ ID NO 27
<211> LENGTH: 23
<212> TYPE: DNA
<213> ORGANISM: Artificial Sequence
<220> FEATURE:
<223> OTHER INFORMATION: Synthetic sequence of site 16

<400> SEQUENCE: 27
aattcactgt aaagctggaa agg 23

<210> SEQ ID NO 28
<211> LENGTH: 23
<212> TYPE: DNA
<213> ORGANISM: Artificial Sequence
<220> FEATURE:
<223> OTHER INFORMATION: Synthetic sequence of site 17

<400> SEQUENCE: 28
ctgtaaaaag gggctgctcc cgg 23

<210> SEQ ID NO 29
<211> LENGTH: 23
<212> TYPE: DNA
<213> ORGANISM: Artificial Sequence
<220> FEATURE:
<223> OTHER INFORMATION: Synthetic sequence of site 18

<400> SEQUENCE: 29
gccaaaacgt gaagaaataa tgg 23

<210> SEQ ID NO 30
<211> LENGTH: 23
<212> TYPE: DNA
<213> ORGANISM: Artificial Sequence
<220> FEATURE:
<223> OTHER INFORMATION: Synthetic sequence of site 19

<400> SEQUENCE: 30
agttaaaaga gaggggctcc cgg 23

<210> SEQ ID NO 31
<211> LENGTH: 23
<212> TYPE: DNA
<213> ORGANISM: Artificial Sequence
<220> FEATURE:
<223> OTHER INFORMATION: Synthetic sequence of site 20

<400> SEQUENCE: 31
ataaaaatgg atcccaacac tgg 23

<210> SEQ ID NO 32
<211> LENGTH: 23
<212> TYPE: DNA
<213> ORGANISM: Artificial Sequence
<220> FEATURE:
<223> OTHER INFORMATION: Synthetic sequence of site 21

<400> SEQUENCE: 32
acccaaggaa tcgaaaaccc agg 23

<210> SEQ ID NO 33
<211> LENGTH: 7629
<212> TYPE: DNA
<213> ORGANISM: Artificial Sequence
<220> FEATURE:
<223> OTHER INFORMATION: pCMV-nCas9 plasmid

<400> SEQUENCE: 33
atatgccaag tacgcccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gcccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
tttttcaaga ccgagattac cctggccaac ggcgagatcc ggaagcggcc tctgatcgag 3660
acaaacggcg aaaccgggga gatcgtgtgg gataagggcc gggattttgc caccgtgcgg 3720
aaagtgctga gcatgcccca agtgaatatc gtgaaaaaga ccgaggtgca gacaggcggc 3780
ttcagcaaag agtctatcct gcccaagagg aacagcgata agctgatcgc cagaaagaag 3840
gactgggacc ctaagaagta cggcggcttc gacagcccca ccgtggccta ttctgtgctg 3900
gtggtggcca aagtggaaaa gggcaagtcc aagaaactga agagtgtgaa agagctgctg 3960
gggatcacca tcatggaaag aagcagcttc gagaagaatc ccatcgactt tctggaagcc 4020
aagggctaca aagaagtgaa aaaggacctg atcatcaagc tgcctaagta ctccctgttc 4080
gagctggaaa acggccggaa gagaatgctg gcctctgccg gcgaactgca gaagggaaac 4140
gaactggccc tgccctccaa atatgtgaac ttcctgtacc tggccagcca ctatgagaag 4200
ctgaagggct cccccgagga taatgagcag aaacagctgt ttgtggaaca gcacaagcac 4260
tacctggacg agatcatcga gcagatcagc gagttctcca agagagtgat cctggccgac 4320

```
gctaatctgg acaaagtgct gtccgcctac aacaagcacc gggataagcc catcagagag   4380
caggccgaga atatcatcca cctgtttacc ctgaccaatc tgggagcccc tgccgccttc   4440
aagtactttg acaccaccat cgaccggaag aggtacacca gcaccaaaga ggtgctggac   4500
gccaccctga tccaccagag catcaccggc ctgtacgaga cacggatcga cctgtctcag   4560
ctgggaggtg actctggcgg ctcaaaaaga accgccgacg gcagcgaatt cgagcccaag   4620
aagaagagga aagtctaacc ggtcatcatc accatcacca ttgagtttaa acccgctgat   4680
cagcctcgac tgtgccttct agttgccagc catctgttgt ttgcccctcc cccgtgcctt   4740
ccttgaccct ggaaggtgcc actcccactg tcctttccta ataaaatgag gaaattgcat   4800
cgcattgtct gagtaggtgt cattctattc tggggggtgg ggtggggcag gacagcaagg   4860
gggaggattg ggaagacaat agcaggcatg ctggggatgc ggtgggctct atggcttctg   4920
aggcggaaag aaccagctgg ggctcgatac cgtcgacctc tagctagagc ttggcgtaat   4980
catggtcata gctgtttcct gtgtgaaatt gttatccgct cacaattcca cacaacatac   5040
gagccggaag cataaagtgt aaagcctagg gtgcctaatg agtgagctaa ctcacattaa   5100
ttgcgttgcg ctcactgccc gctttccagt cgggaaacct gtcgtgccag ctgcattaat   5160
gaatcggcca acgcgcgggg agaggcggtt tgcgtattgg gcgctcttcc gcttcctcgc   5220
tcactgactc gctgcgctcg gtcgttcggc tgcggcgagc ggtatcagct cactcaaagg   5280
cggtaatacg gttatccaca gaatcagggg ataacgcagg aaagaacatg tgagcaaaag   5340
gccagcaaaa ggccaggaac cgtaaaaagg ccgcgttgct ggcgtttttc cataggctcc   5400
gcccccctga cgagcatcac aaaaatcgac gctcaagtca gaggtggcga aacccgacag   5460
gactataaag ataccaggcg tttccccctg gaagctccct cgtgcgctct cctgttccga   5520
ccctgccgct taccggatac ctgtccgcct ttctcccttc gggaagcgtg gcgctttctc   5580
atagctcacg ctgtaggtat ctcagttcgg tgtaggtcgt tcgctccaag ctgggctgtg   5640
tgcacgaacc ccccgttcag cccgaccgct gcgccttatc cggtaactat cgtcttgagt   5700
ccaacccggt aagacacgac ttatcgccac tggcagcagc cactggtaac aggattagca   5760
gagcgaggta tgtaggcggt gctacagagt tcttgaagtg gtggcctaac tacggctaca   5820
ctagaagaac agtatttggt atctgcgctc tgctgaagcc agttaccttc ggaaaaagag   5880
ttggtagctc ttgatccggc aaacaaacca ccgctggtag cggtggtttt tttgtttgca   5940
agcagcagat tacgcgcaga aaaaaaggat ctcaagaaga tcctttgatc ttttctacgg   6000
ggtctgacac tcagtggaac gaaaactcac gttaagggat tttggtcatg agattatcaa   6060
aaaggatctt cacctagatc cttttaaatt aaaaatgaag ttttaaatca atctaaagta   6120
tatatgagta aacttggtct gacagttacc aatgcttaat cagtgaggca cctatctcag   6180
cgatctgtct atttcgttca tccatagttg cctgactccc cgtcgtgtag ataactacga   6240
tacgggaggg cttaccatct ggccccagtg ctgcaatgat accgcgagac ccacgctcac   6300
cggctccaga tttatcagca ataaaccagc cagccggaag ggccgagcgc agaagtggtc   6360
ctgcaacttt atccgcctcc atccagtcta ttaattgttg ccgggaagct agagtaagta   6420
gttcgccagt taatagtttg cgcaacgttg ttgccattgc tacaggcatc gtggtgtcac   6480
gctcgtcgtt tggtatggct tcattcagct ccggttccca acgatcaagg cgagttacat   6540
gatcccccat gttgtgcaaa aaagcggtta gctccttcgg tcctccgatc gttgtcagaa   6600
gtaagttggc cgcagtgtta tcactcatgg ttatggcagc actgcataat tctcttactg   6660
tcatgccatc cgtaagatgc ttttctgtga ctggtgagta ctcaaccaag tcattctgag   6720
```

```
aatagtgtat gcggcgaccg agttgctctt gcccggcgtc aatacgggat aataccgcgc   6780

cacatagcag aactttaaaa gtgctcatca ttggaaaacg ttcttcgggg cgaaaactct   6840

caaggatctt accgctgttg agatccagtt cgatgtaacc cactcgtgca cccaactgat   6900

cttcagcatc ttttactttc accagcgttt ctgggtgagc aaaaacagga aggcaaaatg   6960

ccgcaaaaaa gggaataagg gcgacacgga aatgttgaat actcatactc ttcctttttc   7020

aatattattg aagcatttat cagggttatt gtctcatgag cggatacata tttgaatgta   7080

tttagaaaaa taaacaaata ggggttccgc gcacatttcc ccgaaaagtg ccacctgacg   7140

tcgacggatc gggagatcga tctcccgatc ccctagggtc gactctcagt acaatctgct   7200

ctgatgccgc atagttaagc cagtatctgc tccctgcttg tgtgttggag gtcgctgagt   7260

agtgcgcgag caaaatttaa gctacaacaa ggcaaggctt gaccgacaat tgcatgaaga   7320

atctgcttag ggttaggcgt tttgcgctgc ttcgcgatgt acgggccaga tatacgcgtt   7380

gacattgatt attgactagt tattaatagt aatcaattac ggggtcatta gttcatagcc   7440

catatatgga gttccgcgtt acataactta cggtaaatgg cccgcctggc tgaccgccca   7500

acgacccccg cccattgacg tcaataatga cgtatgttcc catagtaacg ccaataggga   7560

ctttccattg acgtcaatgg gtggagtatt tacggtaaac tgcccacttg gcagtacatc   7620

aagtgtatc                                                           7629
```

```
<210> SEQ ID NO 34
<211> LENGTH: 10864
<212> TYPE: DNA
<213> ORGANISM: Artificial Sequence
<220> FEATURE:
<223> OTHER INFORMATION: pET-nCas9-gRNA-AmpR (A118X)-KanR plasmid

<400> SEQUENCE: 34

gacaagaagt acagcatcgg cctggccatc ggcaccaact ctgtgggctg ggccgtgatc     60

accgacgagt acaaggtgcc cagcaagaaa ttcaaggtgc tgggcaacac cgaccggcac    120

agcatcaaga agaacctgat cggagccctg ctgttcgaca gcggcgaaac agccgaggcc    180

acccggctga agagaaccgc cagaagaaga tacaccagac ggaagaaccg gatctgctat    240

ctgcaagaga tcttcagcaa cgagatggcc aaggtggacg acagcttctt ccacagactg    300

gaagagtcct tcctggtgga agaggataag aagcacgagc ggcaccccat cttcggcaac    360

atcgtggacg aggtggccta ccacgagaag taccccacca tctaccacct gagaaagaaa    420

ctggtggaca gcaccgacaa ggccgacctg cggctgatct atctggccct ggcccacatg    480

atcaagttcc ggggccactt cctgatcgag ggcgacctga accccgacaa cagcgacgtg    540

gacaagctgt tcatccagct ggtgcagacc tacaaccagc tgttcgagga aaaccccatc    600

aacgccagcg gcgtggacgc caaggccatc ctgtctgcca gactgagcaa gagcagacgg    660

ctggaaaatc tgatcgccca gctgcccggc gagaagaaga atggcctgtt cggaaacctg    720

attgccctga gcctgggcct gacccccaac ttcaagagca acttcgacct ggccgaggat    780

gccaaactgc agctgagcaa ggacacctac gacgacgacc tggacaacct gctggcccag    840

atcggcgacc agtacgccga cctgtttctg gccgccaaga acctgtccga cgccatcctg    900

ctgagcgaca tcctgagagt gaacaccgag atcaccaagg ccccccctgag cgcctctatg    960

atcaagagat acgacgagca ccaccaggac ctgaccctgc tgaaagctct cgtgcggcag   1020

cagctgcctg agaagtacaa agagattttc ttcgaccaga gcaagaacgg ctacgccggc   1080
```

-continued

```
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact tttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga acagcgataa gctgatcgcc   3360
agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
```

gagctgctgg ggatcaccat catggaaaga agcagcttcg agaagaatcc catcgacttt 3540
ctggaagcca agggctacaa agaagtgaaa aaggacctga tcatcaagct gcctaagtac 3600
tccctgttcg agctggaaaa cggccggaag agaatgctgg cctctgccgg cgaactgcag 3660
aagggaaacg aactggccct gccctccaaa tatgtgaact tcctgtacct ggccagccac 3720
tatgagaagc tgaagggctc ccccgaggat aatgagcaga aacagctgtt tgtggaacag 3780
cacaagcact acctggacga gatcatcgag cagatcagcg agttctccaa gagagtgatc 3840
ctggccgacg ctaatctgga caaagtgctg tccgcctaca acaagcaccg ggataagccc 3900
atcagagagc aggccgagaa tatcatccac ctgtttaccc tgaccaatct gggagcccct 3960
gccgccttca agtactttga caccaccatc gaccggaaga ggtacaccag caccaaagag 4020
gtgctggacg ccaccctgat ccaccagagc atcaccggcc tgtacgagac acggatcgac 4080
ctgtctcagc tgggaggtga ctctggcggc tcaaaaagaa ccgccgacgg cagcgaattc 4140
gagcccaaga agaagaggaa agtctaaccg gtcatcatca ccatcaccat tgagtttaaa 4200
cccgctgatc agcctcgact gtgccttcta gttgccagcc atctgttgtt tgcccctccc 4260
ccgtgccttc cttgaccctg gaaggtgcca ctcccactgt cctttcctaa taaaatgagg 4320
aaattgcatc gcattgtctg agtaggtgtc attctattct ggggggtggg gtggggcagg 4380
acagcaaggg ggaggattgg gaagacaata gcaggcatgc tggggatgcg gtgggctcta 4440
tggcttctga ggcggaaaga accagctggg gctcgttgac agctagctca gtcctaggta 4500
taatactagt gctcttgccc ggcgtcaata cgttttagag ctagaaatag caagttaaaa 4560
taaggctagt ccgttatcaa cttgaaaaag tggcaccgag tcggtgcttt ttttgatccg 4620
gctgctaaca aagcccgaaa ggaagctgag ttggctgctg ccaccgctga gcaataacta 4680
gcataacccc ttggggcctc taaacgggtc ttgaggggtt ttttgctgaa aggaggaact 4740
atatccggat tggcgaatgg gacgcgccct gtagcggcgc attaagcgcg gcgggtgtgg 4800
tggttacgcg cagcgtgacc gctacacttg ccagcgccct agcgcccgct cctttcgctt 4860
tcttcccttc ctttctcgcc acgttcgccg gctttccccg tcaagctcta aatcgggggc 4920
tccctttagg gttccgattt agtgctttac ggcacctcga ccccaaaaaa cttgattagg 4980
gtgatggttc acgtagtggg ccatcgccct gatagacggt ttttcgccct ttgacgttgg 5040
agtccacgtt ctttaatagt ggactcttgt tccaaactgg aacaacactc aaccctatct 5100
cggtctattc ttttgattta taagggattt tgccgatttc ggcctattgg ttaaaaaatg 5160
agctgattta acaaaaattt aacgcgaatt ttaacaaaat attaacgttt acaatttcag 5220
gtggcacttt tcggggaaat gtgggaaatg tgcgcggaac ccctatttgt ttatttttct 5280
aaatacattc aaatatgtat ccgctcatga gacaataacc ctgataaatg cttcaataat 5340
attgaaaaag gaagagtatg agtattcaac atttccgtgt cgcccttatt cccttttttg 5400
cggcattttg ccttcctgtt tttgctcacc cagaaacgct ggtgaaagta aaagatgctg 5460
aagatcagtt gggtgcacga gtgggttaca tcgaactgga tctcaacagc ggtaagatcc 5520
ttgagagttt tcgccccgaa gaacgttttc caatgatgag cacttttaaa gttctgctat 5580
gtggcgcggt attatcccgt attgacgccg ggtaagagca actcggtcgc cgcatacact 5640
attctcagaa tgacttggtt gagtactcac cagtcacaga aaagcatctt acggatggca 5700
tgacagtaag agaattatgc agtgctgcca taaccatgag tgataacact gcggccaact 5760
tacttctgac aacgatcgga ggaccgaagg agctaaccgc ttttttgcac aacatggggg 5820

-continued

```
atcatgtaac tcgccttgat cgttgggaac cggagctgaa tgaagccata ccaaacgacg   5880
agcgtgacac cacgatgcct gtagcaatgg caacaacgtt gcgcaaacta ttaactggcg   5940
aactacttac tctagcttcc cggcaacaat taatagactg gatggaggcg gataaagttg   6000
caggaccact tctgcgctcg gcccttccgg ctggctggtt tattgctgat aaatctggag   6060
ccggtgagcg tgggtctcgc ggtatcattg cagcactggg gccagatggt aagccctccc   6120
gtatcgtagt tatctacacg acggggagtc aggcaactat ggatgaacga aatagacaga   6180
tcgctgagat aggtgcctca ctgattaagc attggtaagc gcggaacccc tatttgttta   6240
tttttctaaa tacattcaaa tatgtatccg ctcatgaatt aattcttaga aaaactcatc   6300
gagcatcaaa tgaaactgca atttattcat atcaggatta tcaataccat atttttgaaa   6360
aagccgtttc tgtaatgaag gagaaaactc accgaggcag ttccatagga tggcaagatc   6420
ctggtatcgg tctgcgattc cgactcgtcc aacatcaata caacctatta atttcccctc   6480
gtcaaaaata aggttatcaa gtgagaaatc accatgagtg acgactgaat ccggtgagaa   6540
tggcaaaagt ttatgcattt ctttccagac ttgttcaaca ggccagccat tacgctcgtc   6600
atcaaaatca ctcgcatcaa ccaaaccgtt attcattcgt gattgcgcct gagcgagacg   6660
aaatacgcga tcgctgttaa aaggacaatt acaaacagga atcgaatgca accggcgcag   6720
gaacactgcc agcgcatcaa caatattttc acctgaatca ggatattctt ctaatacctg   6780
gaatgctgtt ttcccgggga tcgcagtggt gagtaaccat gcatcatcag gagtacggat   6840
aaaatgcttg atggtcggaa gaggcataaa ttccgtcagc cagtttagtc tgaccatctc   6900
atctgtaaca tcattggcaa cgctaccttt gccatgtttc agaaacaact ctggcgcatc   6960
gggcttccca tacaatcgat agattgtcgc acctgattgc ccgacattat cgcgagccca   7020
tttataccca tataaatcag catccatgtt ggaatttaat cgcggcctag agcaagacgt   7080
ttcccgttga atatggctca taacacccct tgtattactg tttatgtaag cagacagttt   7140
tattgttcat gaccaaaatc ccttaacgtg agttttcgtt ccactgagcg tcagaccccg   7200
tagaaaagat caaaggatct tcttgagatc cttttttct gcgcgtaatc tgctgcttgc   7260
aaacaaaaaa accaccgcta ccagcggtgg tttgtttgcc ggatcaagag ctaccaactc   7320
tttttccgaa ggtaactggc ttcagcagag cgcagatacc aaatactgtc cttctagtgt   7380
agccgtagtt aggccaccac ttcaagaact ctgtagcacc gcctacatac ctcgctctgc   7440
taatcctgtt accagtggct gctgccagtg gcgataagtc gtgtcttacc gggttggact   7500
caagacgata gttaccggat aaggcgcagc ggtcgggctg aacggggggt tcgtgcacac   7560
agcccagctt ggagcgaacg acctacaccg aactgagata cctacagcgt gagctatgag   7620
aaagcgccac gcttcccgaa gggagaaagg cggacaggta tccggtaagc ggcagggtcg   7680
gaacaggaga gcgcacgagg gagcttccag ggggaaacgc ctggtatctt tatagtcctg   7740
tcgggtttcg ccacctctga cttgagcgtc gatttttgtg atgctcgtca ggggggcgga   7800
gcctatggaa aaacgccagc aacgcggcct ttttacggtt cctggccttt tgctggcctt   7860
ttgctcacat gttctttcct gcgttatccc ctgattctgt ggataaccgt attaccgcct   7920
ttgagtgagc tgataccgct cgccgcagcc gaacgaccga gcgcagcgag tcagtgagcg   7980
aggaagcgga agagcgcctg atgcggtatt ttctccttac gcatctgtgc ggtatttcac   8040
accgcatata tggtgcactc tcagtacaat ctgctctgat gccgcatagt taagccagta   8100
tacactccgc tatcgctacg tgactgggtc atggctgcgc cccgacaccc gccaacaccc   8160
gctgacgcgc cctgacgggc ttgtctgctc cggcatccg cttacagaca agctgtgacc   8220
```

```
gtctccggga gctgcatgtg tcagaggttt tcaccgtcat caccgaaacg cgcgaggcag   8280
ctgcggtaaa gctcatcagc gtggtcgtga agcgattcac agatgtctgc ctgttcatcc   8340
gcgtccagct cgttgagttt ctccagaagc gttaatgtct ggcttctgat aaagcgggcc   8400
atgttaaggg cggttttttc ctgtttggtc actgatgcct ccgtgtaagg gggatttctg   8460
ttcatggggg taatgatacc gatgaaacga gagaggatgc tcacgatacg ggttactgat   8520
gatgaacatg cccggttact ggaacgttgt gagggtaaac aactggcggt atggatgcgg   8580
cgggaccaga gaaaaatcac tcagggtcaa tgccagcgct tcgttaatac agatgtaggt   8640
gttccacagg gtagccagca gcatcctgcg atgcagatcc ggaacataat ggtgcagggc   8700
gctgacttcc gcgtttccag actttacgaa acacggaaac cgaagaccat tcatgttgtt   8760
gctcaggtcg cagacgtttt gcagcagcag tcgcttcacg ttcgctcgcg tatcggtgat   8820
tcattctgct aaccagtaag gcaaccccgc cagcctagcc gggtcctcaa cgacaggagc   8880
acgatcatgc gcacccgtgg ggccgccatg ccggcgataa tggcctgctt ctcgccgaaa   8940
cgtttggtgg cgggaccagt gacgaaggct tgagcgaggg cgtgcaagat tccgaatacc   9000
gcaagcgaca ggccgatcat cgtcgcgctc cagcgaaagc ggtcctcgcc gaaaatgacc   9060
cagagcgctg ccggcacctg tcctacgagt tgcatgataa agaagacagt cataagtgcg   9120
gcgacgatag tcatgccccg cgcccaccgg aaggagctga ctgggttgaa ggctctcaag   9180
ggcatcggtc gagatcccgg tgcctaatga gtgagctaac ttacattaat tgcgttgcgc   9240
tcactgcccg ctttccagtc gggaaacctg tcgtgccagc tgcattaatg aatcggccaa   9300
cgcgcgggga gaggcggttt gcgtattggg cgccagggtg gtttttcttt tcaccagtga   9360
gacgggcaac agctgattgc ccttcaccgc ctggccctga gagagttgca gcaagcggtc   9420
cacgctggtt tgccccagca ggcgaaaatc ctgtttgatg gtggttaacg gcgggatata   9480
acatgagctg tcttcggtat cgtcgtatcc cactaccgag atgtccgcac caacgcgcag   9540
cccggactcg gtaatggcgc gcattgcgcc cagcgccatc tgatcgttgg caaccagcat   9600
cgcagtggga acgatgccct cattcagcat ttgcatggtt tgttgaaaac cggacatggc   9660
actccagtcg ccttcccgtt ccgctatcgg ctgaatttga ttgcgagtga gatatttatg   9720
ccagccagcc agacgcagac gcgccgagac agaacttaat gggcccgcta acagcgcgat   9780
ttgctggtga cccaatgcga ccagatgctc cacgcccagt cgcgtaccgt cttcatggga   9840
gaaaataata ctgttgatgg gtgtctggtc agagacatca agaaataacg ccggaacatt   9900
agtgcaggca gcttccacag caatggcatc ctggtcatcc agcggatagt taatgatcag   9960
cccactgacg cgttgcgcga gaagattgtg caccgccgct ttacaggctt cgacgccgct  10020
tcgttctacc atcgacacca ccacgctggc acccagttga tcggcgcgag atttaatcgc  10080
cgcgacaatt tgcgacggcg cgtgcagggc cagactggag gtggcaacgc caatcagcaa  10140
cgactgtttg cccgccagtt gttgtgccac gcggttggga atgtaattca gctccgccat  10200
cgccgcttcc actttttccc gcgttttcgc agaaacgtgg ctggcctggt tcaccacgcg  10260
ggaaacggtc tgataagaga caccggcata ctctgcgaca tcgtataacg ttactggttt  10320
cacattcacc accctgaatt gactctcttc cgggcgctat catgccatac cgcgaaaggt  10380
tttgcgccat tcgatggtgt ccgggatctc gacgctctcc cttatgcgac tcctgcatta  10440
ggaagcagcc cagtagtagg ttgaggccgt tgagcaccgc cgccgcaagg aatggtgcat  10500
gcaaggagat ggcgcccaac agtcccccgg ccacggggcc tgccaccata cccacgccga  10560
```

-continued

```
aacaagcgct catgagcccg aagtggcgag cccgatcttc cccatcggtg atgtcggcga  10620

tataggcgcc agcaaccgca cctgtggcgc cggtgatgcc ggccacgatg cgtccggcgt  10680

agaggatcga gatcgatctc gatcccgcga aattaatacg actcactata ggggaattgt  10740

gagcggataa caattcccct ctagaaataa ttttgtttaa ctttaagaag gagatataca  10800

tgccaccatg aaacggacag ccgacggaag cgagttcgag tcaccaaaga agaagcggaa  10860

agtc                                                              10864
```

<210> SEQ ID NO 35
<211> LENGTH: 3423
<212> TYPE: DNA
<213> ORGANISM: Artificial Sequence
<220> FEATURE:
<223> OTHER INFORMATION: the fragment of CMV-ABE

<400> SEQUENCE: 35

```
cccaagaaga agaggaaagt ctaaccggtc atcatcacca tcaccattga gtttaaaccc     60

gctgatcagc ctcgactgtg ccttctagtt gccagccatc tgttgtttgc ccctcccccg    120

tgccttcctt gaccctggaa ggtgccactc ccactgtcct ttcctaataa aatgaggaaa    180

ttgcatcgca ttgtctgagt aggtgtcatt ctattctggg gggtggggtg gggcaggaca    240

gcaaggggga ggattgggaa gacaatagca ggcatgctgg ggatgcggtg ggctctatgg    300

cttctgaggc ggaaagaacc agctggggct cgataccgtc gacctctagc tagagcttgg    360

cgtaatcatg gtcatagctg tttcctgtgt gaaattgtta tccgctcaca attccacaca    420

acatacgagc cggaagcata aagtgtaaag cctagggtgc ctaatgagtg agctaactca    480

cattaattgc gttgcgctca ctgcccgctt tccagtcggg aaacctgtcg tgccagctgc    540

attaatgaat cggccaacgc gcggggagag gcggtttgcg tattgggcgc tcttccgctt    600

cctcgctcac tgactcgctg cgctcggtcg ttcggctgcg gcgagcggta tcagctcact    660

caaaggcggt aatacggtta tccacagaat caggggataa cgcaggaaag aacatgtgag    720

caaaaggcca gcaaaaggcc aggaaccgta aaaaggccgc gttgctggcg tttttccata    780

ggctccgccc ccctgacgag catcacaaaa atcgacgctc aagtcagagg tggcgaaacc    840

cgacaggact ataaagatac caggcgtttc cccctggaag ctccctcgtg cgctctcctg    900

ttccgaccct gccgcttacc ggatacctgt ccgcctttct cccttcggga agcgtggcgc    960

tttctcatag ctcacgctgt aggtatctca gttcggtgta ggtcgttcgc tccaagctgg   1020

gctgtgtgca cgaacccccc gttcagcccg accgctgcgc cttatccggt aactatcgtc   1080

ttgagtccaa cccggtaaga cacgacttat cgccactggc agcagccact ggtaacagga   1140

ttagcagagc gaggtatgta ggcggtgcta cagagttctt gaagtggtgg cctaactacg   1200

gctacactag aagaacagta tttggtatct gcgctctgct gaagccagtt accttcggaa   1260

aaagagttgg tagctcttga tccggcaaac aaaccaccgc tggtagcggt ggtttttttg   1320

tttgcaagca gcagattacg cgcagaaaaa aaggatctca agaagatcct ttgatctttt   1380

ctacggggtc tgacactcag tggaacgaaa actcacgtta agggattttg gtcatgagat   1440

tatcaaaaag gatcttcacc tagatccttt taaattaaaa atgaagtttt aaatcaatct   1500

aaagtatata tgagtaaact tggtctgaca gttaccaatg cttaatcagt gaggcaccta   1560

tctcagcgat ctgtctattt cgttcatcca tagttgcctg actccccgtc gtgtagataa   1620

ctacgatacg ggagggctta ccatctggcc ccagtgctgc aatgataccg cgagacccac   1680

gctcaccggc tccagattta tcagcaataa accagccagc cggaagggcc gagcgcagaa   1740
```

```
gtggtcctgc aactttatcc gcctccatcc agtctattaa ttgttgccgg gaagctagag   1800

taagtagttc gccagttaat agtttgcgca acgttgttgc cattgctaca ggcatcgtgg   1860

tgtcacgctc gtcgtttggt atggcttcat tcagctccgg ttcccaacga tcaaggcgag   1920

ttacatgatc ccccatgttg tgcaaaaaag cggttagctc cttcggtcct ccgatcgttg   1980

tcagaagtaa gttggccgca gtgttatcac tcatggttat ggcagcactg cataattctc   2040

ttactgtcat gccatccgta agatgctttt ctgtgactgg tgagtactca accaagtcat   2100

tctgagaata gtgtatgcgg cgaccgagtt gctcttgccc ggcgtcaata cgggataata   2160

ccgcgccaca tagcagaact ttaaaagtgc tcatcattgg aaaacgttct tcggggcgaa   2220

aactctcaag gatcttaccg ctgttgagat ccagttcgat gtaacccact cgtgcaccca   2280

actgatcttc agcatctttt actttcacca gcgtttctgg gtgagcaaaa acaggaaggc   2340

aaaatgccgc aaaaaaggga ataagggcga cacggaaatg ttgaatactc atactcttcc   2400

tttttcaata ttattgaagc atttatcagg gttattgtct catgagcgga tacatatttg   2460

aatgtattta gaaaaataaa caaatagggg ttccgcgcac atttccccga aaagtgccac   2520

ctgacgtcga cggatcggga gatcgatctc ccgatcccct agggtcgact ctcagtacaa   2580

tctgctctga tgccgcatag ttaagccagt atctgctccc tgcttgtgtg ttggaggtcg   2640

ctgagtagtg cgcgagcaaa atttaagcta caacaaggca aggcttgacc gacaattgca   2700

tgaagaatct gcttagggtt aggcgttttg cgctgcttcg cgatgtacgg gccagatata   2760

cgcgttgaca ttgattattg actagttatt aatagtaatc aattacgggg tcattagttc   2820

atagcccata tatggagttc cgcgttacat aacttacggt aaatggcccg cctggctgac   2880

cgcccaacga cccccgccca ttgacgtcaa taatgacgta tgttcccata gtaacgccaa   2940

tagggacttt ccattgacgt caatgggtgg agtatttacg gtaaactgcc cacttggcag   3000

tacatcaagt gtatcatatg ccaagtacgc cccctattga cgtcaatgac ggtaaatggc   3060

ccgcctggca ttatgcccag tacatgacct tatgggactt tcctacttgg cagtacatct   3120

acgtattagt catcgctatt accatggtga tgcggttttg gcagtacatc aatgggcgtg   3180

gatagcggtt tgactcacgg ggatttccaa gtctccaccc cattgacgtc aatgggagtt   3240

tgttttggca ccaaaatcaa cgggactttc caaaatgtcg taacaactcc gccccattga   3300

cgcaaatggg cggtaggcgt gtacggtggg aggtctatat aagcagagct ggtttagtga   3360

accgtcagat ccgctagaga tccgcggccg ctaatacgac tcactatagg gagagccgcc   3420

acc                                                                 3423
```

<210> SEQ ID NO 36
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 36

```
atatgccaag tacgccccct attgacgtca atgacggtaa atggcccgcc tggcattatg     60

cccagtacat gaccttatgg gactttccta cttggcagta catctacgta ttagtcatcg    120

ctattaccat ggtgatgcgg ttttggcagt acatcaatgg gcgtggatag cggtttgact    180

cacggggatt tccaagtctc caccccattg acgtcaatgg gagtttgttt tggcaccaaa    240

atcaacggga ctttccaaaa tgtcgtaaca actccgcccc attgacgcaa atgggcggta    300
```

-continued

```
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac ctctggagga tctagcggtg gttcctctgg aagcgagaca   2100
ccaggcacaa gcgagtccgc cacaccagag agctccggcg gctcctccgg aggatcctct   2160
gaggtggagt tttcccacga gtactggatg agacatgccc tgaccctggc caagagggca   2220
tgggatgaaa gagaagtccc cgtgggcgcc gtgctggtgc acaacaatag agtgatcgga   2280
gagggatgga acaggccaat cggccgccac gaccctaccg cacacgcaga gatcatggca   2340
ctgaggcagg gaggcctggt catgcagaat taccgcctga tcgatgccac cctgtatgtg   2400
acactggagc catgcgtgat gtgcgcagga gcaatgatcc acagcaggat cggaagagtg   2460
gtgttcggag cacgggacgc caagaccggc gcagcaggct ccctgatgga tgtgctgcac   2520
caccccggca tgaaccaccg ggtggagatc acagagggaa tcctggcaga cgagtgcgcc   2580
gccctgctga gcgatttctt tagaatgcgg agacaggaga tcaaggccca gaagaaggca   2640
cagagctcca ccgactctgg aggatctagc ggcggatcct ctggaagcga gacaccaggc   2700
```

-continued

```
acaagcgagt ccgccacacc agagagctcc ggcggctcct ccggaggatc ctctgaggtg   2760
gagttttccc acgagtactg gatgagacat gccctgaccc tggccaagag ggcacgcgat   2820
gagagggagg tgcctgtggg agccgtgctg gtgctgaaca atagagtgat cggcgagggc   2880
tggaacagag ccatcggcct gcacgaccca acagcccatg ccgaaattat ggccctgaga   2940
cagggcggcc tggtcatgca gaactacaga ctgattgacg ccaccctgta cgtgacattc   3000
gagccttgcg tgatgtgcgc cggcgccatg atccactcta ggatcggccg cgtggtgttt   3060
ggcgtgagga acgcaaaaac cggcgccgca ggctccctga tggacgtgct gcactacccc   3120
ggcatgaatc accgcgtcga aattaccgag ggaatcctgg cagatgaatg tgccgccctg   3180
ctgtgctatt tctttcggat gcctagacag gtgttcaatg ctcagaagaa ggcccagagc   3240
tccaccgact ccggaggatc tagcggaggc tcctctggct ctgagacacc tggcacaagc   3300
gagagcgcaa cacctgaaag cagcgggggc agcagcgggg ggtcagaggg aatgagaaag   3360
cccgccttcc tgagcggcga gcagaaaaag gccatcgtgg acctgctgtt caagaccaac   3420
cggaaagtga ccgtgaagca gctgaaagag gactacttca agaaaatcga gtgcttcgac   3480
tccgtggaaa tctccggcgt ggaagatcgg ttcaacgcct ccctgggcac ataccacgat   3540
ctgctgaaaa ttatcaagga caaggacttc ctggacaatg aggaaaacga ggacattctg   3600
gaagatatcg tgctgaccct gacactgttt gaggacagag agatgatcga ggaacggctg   3660
aaaacctatg cccacctgtt cgacgacaaa gtgatgaagc agctgaagcg gcggagatac   3720
accggctggg gcaggctgag ccggaagctg atcaacggca tccgggacaa gcagtccggc   3780
aagacaatcc tggatttcct gaagtccgac ggcttcgcca acagaaactt catgcagctg   3840
atccacgacg acagcctgac ctttaaagag gacatccaga aagcccaggt gtccggccag   3900
ggcgatagcc tgcacgagca cattgccaat ctggccggca gccccgccat taagaagggc   3960
atcctgcaga cagtgaaggt ggtggacgag ctcgtgaaag tgatgggccg gcacaagccc   4020
gagaacatcg tgatcgaaat ggccagagag aaccagacca cccagaaggg acagaagaac   4080
agccgcgaga gaatgaagcg gatcgaagag ggcatcaaag agctgggcag ccagatcctg   4140
aaagaacacc ccgtggaaaa cacccagctg cagaacgaga agctgtacct gtactacctg   4200
cagaatgggc gggatatgta cgtggaccag gaactggaca tcaaccggct gtccgactac   4260
gatgtggacc atatcgtgcc tcagagcttt ctgaaggacg actccatcga caacaaggtg   4320
ctgaccagaa gcgacaagaa ccggggcaag agcgacaacg tgccctccga agaggtcgtg   4380
aagaagatga agaactactg gcggcagctg ctgaacgcca agctgattac ccagagaaag   4440
ttcgacaatc tgaccaaggc cgagagaggc ggcctgagcg aactggataa ggccggcttc   4500
atcaagagac agctggtgga aacccggcag atcacaaagc acgtggcaca gatcctggac   4560
tcccggatga acactaagta cgacgagaat gacaagctga tccgggaagt gaaagtgatc   4620
accctgaagt ccaagctggt gtccgatttc cggaaggatt tccagtttta caaagtgcgc   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
ggccgggatt ttgccaccgt gcggaaagtg ctgagcatgc cccaagtgaa tatcgtgaaa   5040
```

```
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
```

```
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913
```

<210> SEQ ID NO 37
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 37

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
```

```
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
tctggaggat ctagcggtgg ttcctctgga agcgagacac caggcacaag cgagtccgcc   2280
acaccagaga gctccggcgg ctcctccgga ggatcctctg aggtggagtt ttcccacgag   2340
tactggatga gacatgccct gaccctggcc aagagggcat gggatgaaag agaagtcccc   2400
gtgggcgccg tgctggtgca caacaataga gtgatcggag agggatggaa caggccaatc   2460
ggccgccacg accctaccgc acacgcagag atcatggcac tgaggcaggg aggcctggtc   2520
atgcagaatt accgcctgat cgatgccacc ctgtatgtga cactggagcc atgcgtgatg   2580
tgcgcaggag caatgatcca cagcaggatc ggaagagtgg tgttcggagc acgggacgcc   2640
aagaccggcg cagcaggctc cctgatggat gtgctgcacc accccggcat gaaccaccgg   2700
gtggagatca cagagggaat cctggcagac gagtgcgccg ccctgctgag cgatttcttt   2760
agaatgcgga gacaggagat caaggcccag aagaaggcac agagctccac cgactctgga   2820
ggatctagcg gcggatcctc tggaagcgag acaccaggca caagcgagtc cgccacacca   2880
gagagctccg gcggctcctc cggaggatcc tctgaggtgg agttttccca cgagtactgg   2940
```

```
atgagacatg ccctgaccct ggccaagagg gcacgcgatg agagggaggt gcctgtggga   3000
gccgtgctgg tgctgaacaa tagagtgatc ggcgagggct ggaacagagc catcggcctg   3060
cacgacccaa cagcccatgc cgaaattatg gccctgagac agggcggcct ggtcatgcag   3120
aactacagac tgattgacgc caccctgtac gtgacattcg agccttgcgt gatgtgcgcc   3180
ggcgccatga tccactctag gatcggccgc gtggtgtttg gcgtgaggaa cgcaaaaacc   3240
ggcgccgcag gctccctgat ggacgtgctg cactaccccg gcatgaatca ccgcgtcgaa   3300
attaccgagg gaatcctggc agatgaatgt gccgccctgc tgtgctattt ctttcggatg   3360
cctagacagg tgttcaatgc tcagaagaag gcccagagct ccaccgactc cggaggatct   3420
agcggaggct cctctggctc tgagacacct ggcacaagcg agagcgcaac acctgaaagc   3480
agcgggggca gcagcggggg gtcagatcgg ttcaacgcct ccctgggcac ataccacgat   3540
ctgctgaaaa ttatcaagga caaggacttc ctggacaatg aggaaaacga ggacattctg   3600
gaagatatcg tgctgaccct gacactgttt gaggacagag agatgatcga ggaacggctg   3660
aaaacctatg cccacctgtt cgacgacaaa gtgatgaagc agctgaagcg gcggagatac   3720
accggctggg gcaggctgag ccggaagctg atcaacggca tccgggacaa gcagtccggc   3780
aagacaatcc tggatttcct gaagtccgac ggcttcgcca acagaaactt catgcagctg   3840
atccacgacg acagcctgac ctttaaagag gacatccaga aagcccaggt gtccggccag   3900
ggcgatagcc tgcacgagca cattgccaat ctggccggca gccccgccat taagaagggc   3960
atcctgcaga cagtgaaggt ggtggacgag ctcgtgaaag tgatgggccg gcacaagccc   4020
gagaacatcg tgatcgaaat ggccagagag aaccagacca cccagaaggg acagaagaac   4080
agccgcgaga gaatgaagcg gatcgaagag ggcatcaaag agctgggcag ccagatcctg   4140
aaagaacacc ccgtggaaaa cacccagctg cagaacgaga agctgtacct gtactacctg   4200
cagaatgggc gggatatgta cgtggaccag gaactggaca tcaaccggct gtccgactac   4260
gatgtggacc atatcgtgcc tcagagcttt ctgaaggacg actccatcga caacaaggtg   4320
ctgaccagaa gcgacaagaa ccggggcaag agcgacaacg tgccctccga agaggtcgtg   4380
aagaagatga agaactactg gcggcagctg ctgaacgcca agctgattac ccagagaaag   4440
ttcgacaatc tgaccaaggc cgagagaggc ggcctgagcg aactggataa ggccggcttc   4500
atcaagagac agctggtgga aacccggcag atcacaaagc acgtggcaca gatcctggac   4560
tcccggatga acactaagta cgacgagaat gacaagctga tccgggaagt gaaagtgatc   4620
accctgaagt ccaagctggt gtccgatttc cggaaggatt tccagtttta caaagtgcgc   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
ggccgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
```

-continued

```
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
```

```
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913
```

<210> SEQ ID NO 38
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 38

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
```

-continued

```
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga  1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agtctggagg atctagcggt ggttcctctg gaagcgagac accaggcaca   2820
agcgagtccg ccacaccaga gagctccggc ggctcctccg gaggatcctc tgaggtggag   2880
ttttcccacg agtactggat gagacatgcc ctgaccctgg ccaagagggc atgggatgaa   2940
agagaagtcc ccgtgggcgc cgtgctggtg cacaacaata gagtgatcgg agagggatgg   3000
aacaggccaa tcggccgcca cgaccctacc gcacacgcag agatcatggc actgaggcag   3060
ggaggcctgg tcatgcagaa ttaccgcctg atcgatgcca ccctgtatgt gacactggag   3120
ccatgcgtga tgtgcgcagg agcaatgatc cacagcagga tcggaagagt ggtgttcgga   3180
```

gcacgggacg ccaagaccgg cgcagcaggc tccctgatgg atgtgctgca ccaccccggc 3240
atgaaccacc gggtggagat cacagaggga atcctggcag acgagtgcgc cgccctgctg 3300
agcgatttct ttagaatgcg gagacaggag atcaaggccc agaagaaggc acagagctcc 3360
accgactctg gaggatctag cggcggatcc tctggaagcg agacaccagg cacaagcgag 3420
tccgccacac cagagagctc cggcggctcc tccggaggat cctctgaggt ggagttttcc 3480
cacgagtact ggatgagaca tgccctgacc ctggccaaga gggcacgcga tgagagggag 3540
gtgcctgtgg gagccgtgct ggtgctgaac aatagagtga tcggcgaggg ctggaacaga 3600
gccatcggcc tgcacgaccc aacagcccat gccgaaatta tggccctgag acagggcggc 3660
ctggtcatgc agaactacag actgattgac gccaccctgt acgtgacatt cgagccttgc 3720
gtgatgtgcg ccggcgccat gatccactct aggatcggcc gcgtggtgtt tggcgtgagg 3780
aacgcaaaaa ccggcgccgc aggctccctg atggacgtgc tgcactaccc cggcatgaat 3840
caccgcgtcg aaattaccga gggaatcctg gcagatgaat gtgccgccct gctgtgctat 3900
ttctttcgga tgcctagaca ggtgttcaat gctcagaaga aggcccagag ctccaccgac 3960
tccggaggat ctagcggagg ctcctctggc tctgagacac ctggcacaag cgagagcgca 4020
acacctgaaa gcagcggggg cagcagcggg gggtcaacca cccagaaggg acagaagaac 4080
agccgcgaga gaatgaagcg gatcgaagag ggcatcaaag agctgggcag ccagatcctg 4140
aaagaacacc ccgtggaaaa cacccagctg cagaacgaga agctgtacct gtactacctg 4200
cagaatgggc gggatatgta cgtggaccag gaactggaca tcaaccggct gtccgactac 4260
gatgtggacc atatcgtgcc tcagagcttt ctgaaggacg actccatcga caacaaggtg 4320
ctgaccagaa gcgacaagaa ccggggcaag agcgacaacg tgccctccga agaggtcgtg 4380
aagaagatga agaactactg gcggcagctg ctgaacgcca agctgattac ccagagaaag 4440
ttcgacaatc tgaccaaggc cgagagaggc ggcctgagcg aactggataa ggccggcttc 4500
atcaagagac agctggtgga aacccggcag atcacaaagc acgtggcaca gatcctggac 4560
tcccggatga acactaagta cgacgagaat gacaagctga tccgggaagt gaaagtgatc 4620
accctgaagt ccaagctggt gtccgatttc cggaaggatt tccagtttta caaagtgcgc 4680
gagatcaaca actaccacca cgcccacgac gcctacctga acgccgtcgt gggaaccgcc 4740
ctgatcaaaa agtaccctaa gctggaaagc gagttcgtgt acggcgacta caaggtgtac 4800
gacgtgcgga agatgatcgc caagagcgag caggaaatcg gcaaggctac cgccaagtac 4860
ttcttctaca gcaacatcat gaactttttc aagaccgaga ttaccctggc caacggcgag 4920
atccggaagc ggcctctgat cgagacaaac ggcgaaaccg gggagatcgt gtgggataag 4980
ggccgggatt ttgccaccgt gcggaaagtg ctgagcatgc cccaagtgaa tatcgtgaaa 5040
aagaccgagg tgcagacagg cggcttcagc aaagagtcta tcctgcccaa gaggaacagc 5100
gataagctga tcgccagaaa gaaggactgg gaccctaaga agtacggcgg cttcgacagc 5160
cccaccgtgg cctattctgt gctggtggtg gccaaagtgg aaaagggcaa gtccaagaaa 5220
ctgaagagtg tgaaagagct gctggggatc accatcatgg aaagaagcag cttcgagaag 5280
aatcccatcg actttctgga agccaagggc tacaaagaag tgaaaaagga cctgatcatc 5340
aagctgccta agtactccct gttcgagctg gaaaacggcc ggaagagaat gctggcctct 5400
gccggcgaac tgcagaaggg aaacgaactg gccctgccct ccaaatatgt gaacttcctg 5460
tacctggcca gccactatga gaagctgaag ggctccccg aggataatga gcagaaacag 5520

-continued ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg gaagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 39
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 39
atatgccaag tacgcccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020

-continued ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gcccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaactctg gaggatctag cggtggttcc 2820
tctggaagcg agacaccagg cacaagcgag tccgccacac cagagagctc cggcggctcc 2880
tccggaggat cctctgaggt ggagttttcc cacgagtact ggatgagaca tgccctgacc 2940
ctggccaaga gggcatggga tgaaagagaa gtccccgtgg gcgccgtgct ggtgcacaac 3000
aatagagtga tcggagaggg atggaacagg ccaatcggcc gccacgaccc taccgcacac 3060
gcagagatca tggcactgag gcagggaggc ctggtcatgc agaattaccg cctgatcgat 3120
gccaccctgt atgtgacact ggagccatgc gtgatgtgcg caggagcaat gatccacagc 3180
aggatcggaa gagtggtgtt cggagcacgg gacgccaaga ccggcgcagc aggctccctg 3240
atggatgtgc tgcaccaccc cggcatgaac caccgggtgg agatcacaga gggaatcctg 3300
gcagacgagt gcgccgccct gctgagcgat ttctttagaa tgcggagaca ggagatcaag 3360
gcccagaaga aggcacagag ctccaccgac tctggaggat ctagcggcgg atcctctgga 3420
agcgagacac caggcacaag cgagtccgcc acaccagaga gctccggcgg ctcctccgga 3480
ggatcctctg aggtggagtt ttcccacgag tactggatga gacatgccct gaccctggcc 3540
aagagggcac gcgatgagag ggaggtgcct gtgggagccg tgctggtgct gaacaataga 3600
gtgatcggcg agggctggaa cagagccatc ggcctgcacg acccaacagc ccatgccgaa 3660
attatggccc tgagacaggg cggcctggtc atgcagaact acagactgat tgacgccacc 3720
ctgtacgtga cattcgagcc ttgcgtgatg tgcgccggcg ccatgatcca ctctaggatc 3780
ggccgcgtgg tgtttggcgt gaggaacgca aaaaccggcg ccgcaggctc cctgatggac 3840
gtgctgcact accccggcat gaatcaccgc gtcgaaatta ccgagggaat cctggcagat 3900
gaatgtgccg ccctgctgtg ctatttcttt cggatgccta gacaggtgtt caatgctcag 3960
aagaaggccc agagctccac cgactccgga ggatctagcg gaggctcctc tggctctgag 4020
acacctggca caagcgagag cgcaacacct gaaagcagcg ggggcagcag cgggggggtca 4080
agccgcgaga gaatgaagcg gatcgaagag ggcatcaaag agctgggcag ccagatcctg 4140
aaagaacacc ccgtggaaaa cacccagctg cagaacgaga agctgtacct gtactacctg 4200
cagaatgggc gggatatgta cgtggaccag gaactggaca tcaaccggct gtccgactac 4260
gatgtggacc atatcgtgcc tcagagcttt ctgaaggacg actccatcga caacaaggtg 4320
ctgaccagaa gcgacaagaa ccggggcaag agcgacaacg tgccctccga agaggtcgtg 4380
aagaagatga agaactactg gcggcagctg ctgaacgcca agctgattac ccagagaaag 4440
ttcgacaatc tgaccaaggc cgagagaggc ggcctgagcg aactggataa ggccggcttc 4500
atcaagagac agctggtgga aacccggcag atcacaaagc acgtggcaca gatcctggac 4560
tcccggatga acactaagta cgacgagaat gacaagctga tccgggaagt gaaagtgatc 4620
accctgaagt ccaagctggt gtccgatttc cggaaggatt tccagtttta caaagtgcgc 4680
gagatcaaca actaccacca cgcccacgac gcctacctga acgccgtcgt gggaaccgcc 4740
ctgatcaaaa agtaccctaa gctggaaagc gagttcgtgt acggcgacta caaggtgtac 4800
gacgtgcgga agatgatcgc caagagcgag caggaaatcg gcaaggctac cgccaagtac 4860
ttcttctaca gcaacatcat gaactttttc aagaccgaga ttaccctggc caacggcgag 4920
atccggaagc ggcctctgat cgagacaaac ggcgaaaccg gggagatcgt gtgggataag 4980
ggccgggatt ttgccaccgt gcggaaagtg ctgagcatgc cccaagtgaa tatcgtgaaa 5040
aagaccgagg tgcagacagg cggcttcagc aaagagtcta tcctgcccaa gaggaacagc 5100
gataagctga tcgccagaaa gaaggactgg gaccctaaga agtacggcgg cttcgacagc 5160
cccaccgtgg cctattctgt gctggtggtg gccaaagtgg aaaagggcaa gtccaagaaa 5220
ctgaagagtg tgaaagagct gctggggatc accatcatgg aaagaagcag cttcgagaag 5280
aatcccatcg actttctgga agccaagggc tacaaagaag tgaaaaagga cctgatcatc 5340
aagctgccta agtactccct gttcgagctg gaaaacggcc ggaagagaat gctggcctct 5400
gccggcgaac tgcagaaggg aaacgaactg gccctgccct ccaaatatgt gaacttcctg 5460
tacctggcca gccactatga gaagctgaag ggctcccccg aggataatga gcagaaacag 5520
ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760

-continued

```
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
```

aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 40
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 40
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260

-continued cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggtctgg aggatctagc 2940
ggtggttcct ctggaagcga gacaccaggc acaagcgagt ccgccacacc agagagctcc 3000
ggcggctcct ccggaggatc ctctgaggtg gagttttccc acgagtactg gatgagacat 3060
gccctgaccc tggccaagag ggcatgggat gaaagagaag tccccgtggg cgccgtgctg 3120
gtgcacaaca atagagtgat cggagaggga tggaacaggc caatcggccg ccacgaccct 3180
accgcacacg cagagatcat ggcactgagg cagggaggcc tggtcatgca gaattaccgc 3240
ctgatcgatg ccaccctgta tgtgacactg gagccatgcg tgatgtgcgc aggagcaatg 3300
atccacagca ggatcggaag agtggtgttc ggagcacggg acgccaagac cggcgcagca 3360
ggctccctga tggatgtgct gcaccacccc ggcatgaacc accgggtgga gatcacagag 3420
ggaatcctgg cagacgagtg cgccgccctg ctgagcgatt tctttagaat gcggagacag 3480
gagatcaagg cccagaagaa ggcacagagc tccaccgact ctggaggatc tagcggcgga 3540
tcctctggaa gcgagacacc aggcacaagc gagtccgcca caccagagag ctccggcggc 3600
tcctccggag gatcctctga ggtggagttt tcccacgagt actggatgag acatgccctg 3660
accctggcca agagggcacg cgatgagagg gaggtgcctg tgggagccgt gctggtgctg 3720
aacaatagag tgatcggcga gggctggaac agagccatcg gcctgcacga cccaacagcc 3780
catgccgaaa ttatggccct gagacagggc ggcctggtca tgcagaacta cagactgatt 3840
gacgccaccc tgtacgtgac attcgagcct tgcgtgatgt gcgccggcgc catgatccac 3900
tctaggatcg gccgcgtggt gtttggcgtg aggaacgcaa aaaccggcgc cgcaggctcc 3960
ctgatggacg tgctgcacta ccccggcatg aatcaccgcg tcgaaattac cgagggaatc 4020
ctggcagatg aatgtgccgc cctgctgtgc tatttctttc ggatgcctag acaggtgttc 4080
aatgctcaga agaaggccca gagctccacc gactccggag gatctagcgg aggctcctct 4140
ggctctgaga cacctggcac aagcgagagc gcaacacctg aaagcagcgg gggcagcagc 4200
ggggggtcac gggatatgta cgtggaccag gaactggaca tcaaccggct gtccgactac 4260
gatgtggacc atatcgtgcc tcagagcttt ctgaaggacg actccatcga caacaaggtg 4320
ctgaccagaa gcgacaagaa ccggggcaag agcgacaacg tgccctccga agaggtcgtg 4380
aagaagatga agaactactg gcggcagctg ctgaacgcca agctgattac ccagagaaag 4440
ttcgacaatc tgaccaaggc cgagagaggc ggcctgagcg aactggataa ggccggcttc 4500
atcaagagac agctggtgga aacccggcag atcacaaagc acgtggcaca gatcctggac 4560
tcccggatga acactaagta cgacgagaat gacaagctga tccgggaagt gaaagtgatc 4620
accctgaagt ccaagctggt gtccgatttc cggaaggatt tccagtttta caaagtgcgc 4680
gagatcaaca actaccacca cgcccacgac gcctacctga acgccgtcgt gggaaccgcc 4740
ctgatcaaaa agtaccctaa gctggaaagc gagttcgtgt acggcgacta caaggtgtac 4800
gacgtgcgga agatgatcgc caagagcgag caggaaatcg gcaaggctac cgccaagtac 4860
ttcttctaca gcaacatcat gaactttttc aagaccgaga ttaccctggc caacggcgag 4920
atccggaagc ggcctctgat cgagacaaac ggcgaaaccg gggagatcgt gtgggataag 4980
ggccgggatt ttgccaccgt gcggaaagtg ctgagcatgc cccaagtgaa tatcgtgaaa 5040
aagaccgagg tgcagacagg cggcttcagc aaagagtcta tcctgcccaa gaggaacagc 5100
gataagctga tcgccagaaa gaaggactgg gaccctaaga agtacggcgg cttcgacagc 5160
cccaccgtgg cctattctgt gctggtggtg gccaaagtgg aaaagggcaa gtccaagaaa 5220
ctgaagagtg tgaaagagct gctggggatc accatcatgg aaagaagcag cttcgagaag 5280
aatcccatcg actttctgga agccaagggc tacaaagaag tgaaaaagga cctgatcatc 5340
aagctgccta agtactccct gttcgagctg gaaaacggcc ggaagagaat gctggcctct 5400
gccggcgaac tgcagaaggg aaacgaactg gccctgccct ccaaatatgt gaacttcctg 5460
tacctggcca gccactatga gaagctgaag ggctcccccg aggataatga gcagaaacag 5520
ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000

-continued ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg gaagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400

```
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                 8913
```

<210> SEQ ID NO 41
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 41

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga    1440
tacgacgagc accaccagga cctgaccctg ctgaaagctc tcgtgcggca gcagctgcct   1500
```

-continued

```
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ctctggagga tctagcggtg gttcctctgg aagcgagaca   3000
ccaggcacaa gcgagtccgc cacaccagag agctccggcg gctcctccgg aggatcctct   3060
gaggtggagt tttcccacga gtactggatg agacatgccc tgaccctggc caagagggca   3120
tgggatgaaa gagaagtccc cgtgggcgcc gtgctggtgc acaacaatag agtgatcgga   3180
gagggatgga acaggccaat cggccgccac gaccctaccg cacacgcaga gatcatggca   3240
ctgaggcagg gaggcctggt catgcagaat taccgcctga tcgatgccac cctgtatgtg   3300
acactggagc catgcgtgat gtgcgcagga gcaatgatcc acagcaggat cggaagagtg   3360
gtgttcggag cacgggacgc caagaccggc gcagcaggct ccctgatgga tgtgctgcac   3420
caccccggca tgaaccaccg ggtggagatc acagagggaa tcctggcaga cgagtgcgcc   3480
gccctgctga gcgatttctt tagaatgcgg agacaggaga tcaaggccca gaagaaggca   3540
cagagctcca ccgactctgg aggatctagc ggcggatcct ctggaagcga gacaccaggc   3600
acaagcgagt ccgccacacc agagagctcc ggcggctcct ccggaggatc ctctgaggtg   3660
gagttttccc acgagtactg gatgagacat gccctgaccc tggccaagag ggcacgcgat   3720
gagagggagg tgcctgtggg agccgtgctg gtgctgaaca atagagtgat cggcgagggc   3780
tggaacagag ccatcggcct gcacgaccca acagcccatg ccgaaattat ggccctgaga   3840
cagggcggcc tggtcatgca gaactacaga ctgattgacg ccaccctgta cgtgacattc   3900
```

gagccttgcg tgatgtgcgc cggcgccatg atccactcta ggatcggccg cgtggtgttt 3960
ggcgtgagga acgcaaaaac cggcgccgca ggctccctga tggacgtgct gcactacccc 4020
ggcatgaatc accgcgtcga aattaccgag ggaatcctgg cagatgaatg tgccgccctg 4080
ctgtgctatt tctttcggat gcctagacag gtgttcaatg ctcagaagaa ggcccagagc 4140
tccaccgact ccggaggatc tagcggaggc tcctctggct ctgagacacc tggcacaagc 4200
gagagcgcaa cacctgaaag cagcgggggc agcagcgggg ggtcacggct gtccgactac 4260
gatgtggacc atatcgtgcc tcagagcttt ctgaaggacg actccatcga caacaaggtg 4320
ctgaccagaa gcgacaagaa ccggggcaag agcgacaacg tgccctccga agaggtcgtg 4380
aagaagatga agaactactg gcggcagctg ctgaacgcca agctgattac ccagagaaag 4440
ttcgacaatc tgaccaaggc cgagagaggc ggcctgagcg aactggataa ggccggcttc 4500
atcaagagac agctggtgga aacccggcag atcacaaagc acgtggcaca gatcctggac 4560
tcccggatga acactaagta cgacgagaat gacaagctga tccgggaagt gaaagtgatc 4620
accctgaagt ccaagctggt gtccgatttc cggaaggatt tccagtttta caaagtgcgc 4680
gagatcaaca actaccacca cgcccacgac gcctacctga acgccgtcgt gggaaccgcc 4740
ctgatcaaaa agtaccctaa gctggaaagc gagttcgtgt acggcgacta caaggtgtac 4800
gacgtgcgga agatgatcgc caagagcgag caggaaatcg gcaaggctac cgccaagtac 4860
ttcttctaca gcaacatcat gaactttttc aagaccgaga ttaccctggc caacggcgag 4920
atccggaagc ggcctctgat cgagacaaac ggcgaaaccg gggagatcgt gtgggataag 4980
ggccgggatt ttgccaccgt gcggaaagtg ctgagcatgc cccaagtgaa tatcgtgaaa 5040
aagaccgagg tgcagacagg cggcttcagc aaagagtcta tcctgcccaa gaggaacagc 5100
gataagctga tcgccagaaa gaaggactgg gaccctaaga agtacggcgg cttcgacagc 5160
cccaccgtgg cctattctgt gctggtggtg gccaaagtgg aaaagggcaa gtccaagaaa 5220
ctgaagagtg tgaaagagct gctggggatc accatcatgg aaagaagcag cttcgagaag 5280
aatcccatcg actttctgga agccaagggc tacaaagaag tgaaaaagga cctgatcatc 5340
aagctgccta agtactccct gttcgagctg gaaaacggcc ggaagagaat gctggcctct 5400
gccggcgaac tgcagaaggg aaacgaactg gccctgccct ccaaatatgt gaacttcctg 5460
tacctggcca gccactatga gaagctgaag ggctcccccg aggataatga gcagaaacag 5520
ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240

-continued

```
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
```

atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 42
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 42
atatgccaag tacgcccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
tctggaggat ctagcggtgg ttcctctgga agcgagacac caggcacaag cgagtccgcc 3300
acaccagaga gctccggcgg ctcctccgga ggatcctctg aggtggagtt ttcccacgag 3360
tactggatga gacatgccct gaccctggcc aagagggcat gggatgaaag agaagtcccc 3420
gtgggcgccg tgctggtgca caacaataga gtgatcggag agggatggaa caggccaatc 3480
ggccgccacg accctaccgc acacgcagag atcatggcac tgaggcaggg aggcctggtc 3540
atgcagaatt accgcctgat cgatgccacc ctgtatgtga cactggagcc atgcgtgatg 3600
tgcgcaggag caatgatcca cagcaggatc ggaagagtgg tgttcggagc acgggacgcc 3660
aagaccggcg cagcaggctc cctgatggat gtgctgcacc accccggcat gaaccaccgg 3720
gtggagatca cagagggaat cctggcagac gagtgcgccg ccctgctgag cgatttcttt 3780
agaatgcgga gacaggagat caaggcccag aagaaggcac agagctccac cgactctgga 3840
ggatctagcg gcggatcctc tggaagcgag acaccaggca caagcgagtc cgccacacca 3900
gagagctccg gcggctcctc cggaggatcc tctgaggtgg agttttccca cgagtactgg 3960
atgagacatg ccctgaccct ggccaagagg gcacgcgatg agagggaggt gcctgtggga 4020
gccgtgctgg tgctgaacaa tagagtgatc ggcgagggct ggaacagagc catcggcctg 4080
cacgacccaa cagcccatgc cgaaattatg gccctgagac agggcggcct ggtcatgcag 4140

-continued

```
aactacagac tgattgacgc caccctgtac gtgacattcg agccttgcgt gatgtgcgcc   4200
ggcgccatga tccactctag gatcggccgc gtggtgtttg gcgtgaggaa cgcaaaaacc   4260
ggcgccgcag gctccctgat ggacgtgctg cactaccccg gcatgaatca ccgcgtcgaa   4320
attaccgagg gaatcctggc agatgaatgt gccgccctgc tgtgctattt ctttcggatg   4380
cctagacagg tgttcaatgc tcagaagaag gcccagagct ccaccgactc cggaggatct   4440
agcggaggct cctctggctc tgagacacct ggcacaagcg agagcgcaac acctgaaagc   4500
agcgggggca gcagcggggg gtcacggcag atcacaaagc acgtggcaca gatcctggac   4560
tcccggatga acactaagta cgacgagaat gacaagctga tccgggaagt gaaagtgatc   4620
accctgaagt ccaagctggt gtccgatttc cggaaggatt tccagtttta caaagtgcgc   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
ggccgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
```

-continued

```
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
```

aaactgccca cttggcagta catcaagtgt atc 8913

<210> SEQ ID NO 43
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 43
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gccccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980

-continued

```
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtctgg aggatctagc ggtggttcct ctggaagcga gacaccaggc   3540
acaagcgagt ccgccacacc agagagctcc ggcggctcct ccggaggatc ctctgaggtg   3600
gagttttccc acgagtactg gatgagacat gccctgaccc tggccaagag ggcatgggat   3660
gaaagagaag tccccgtggg cgccgtgctg gtgcacaaca atagagtgat cggagaggga   3720
tggaacaggc caatcggccg ccacgaccct accgcacacg cagagatcat ggcactgagg   3780
cagggaggcc tggtcatgca gaattaccgc ctgatcgatg ccaccctgta tgtgacactg   3840
gagccatgcg tgatgtgcgc aggagcaatg atccacagca ggatcggaag agtggtgttc   3900
ggagcacggg acgccaagac cggcgcagca ggctccctga tggatgtgct gcaccacccc   3960
ggcatgaacc accgggtgga gatcacagag ggaatcctgg cagacgagtg cgccgccctg   4020
ctgagcgatt tctttagaat gcggagacag gagatcaagg cccagaagaa ggcacagagc   4080
tccaccgact ctggaggatc tagcggcgga tcctctggaa gcgagacacc aggcacaagc   4140
gagtccgcca caccagagag ctccggcggc tcctccggag gatcctctga ggtggagttt   4200
tcccacgagt actggatgag acatgccctg accctggcca agagggcacg cgatgagagg   4260
gaggtgcctg tgggagccgt gctggtgctg aacaatagag tgatcggcga gggctggaac   4320
agagccatcg gcctgcacga cccaacagcc catgccgaaa ttatggccct gagacagggc   4380
```

-continued

```
ggcctggtca tgcagaacta cagactgatt gacgccaccc tgtacgtgac attcgagcct   4440
tgcgtgatgt gcgccggcgc catgatccac tctaggatcg gccgcgtggt gtttggcgtg   4500
aggaacgcaa aaaccggcgc cgcaggctcc ctgatggacg tgctgcacta ccccggcatg   4560
aatcaccgcg tcgaaattac cgagggaatc ctggcagatg aatgtgccgc cctgctgtgc   4620
tatttctttc ggatgcctag acaggtgttc aatgctcaga agaaggccca gagctccacc   4680
gactccggag gatctagcgg aggctcctct ggctctgaga cacctggcac aagcgagagc   4740
gcaacacctg aaagcagcgg gggcagcagc ggggggtcat acggcgacta caaggtgtac   4800
gacgtgcgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
ggccgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
```

-continued

```
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913
```

<210> SEQ ID NO 44
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 44

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
```

gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgtctggagg atctagcggt 3540
ggttcctctg gaagcgagac accaggcaca agcgagtccg ccacaccaga gagctccggc 3600
ggctcctccg gaggatcctc tgaggtggag ttttcccacg agtactggat gagacatgcc 3660
ctgaccctgg ccaagagggc atgggatgaa agagaagtcc ccgtgggcgc cgtgctggtg 3720
cacaacaata gagtgatcgg agagggatgg aacaggccaa tcggccgcca cgaccctacc 3780
gcacacgcag agatcatggc actgaggcag ggaggcctgg tcatgcagaa ttaccgcctg 3840
atcgatgcca ccctgtatgt gacactggag ccatgcgtga tgtgcgcagg agcaatgatc 3900
cacagcagga tcggaagagt ggtgttcgga gcacgggacg ccaagaccgg cgcagcaggc 3960
tccctgatgg atgtgctgca ccaccccggc atgaaccacc gggtggagat cacagaggga 4020
atcctggcag acgagtgcgc cgccctgctg agcgatttct ttagaatgcg gagacaggag 4080
atcaaggccc agaagaaggc acagagctcc accgactctg gaggatctag cggcggatcc 4140
tctggaagcg agacaccagg cacaagcgag tccgccacac cagagagctc cggcggctcc 4200
tccggaggat cctctgaggt ggagttttcc cacgagtact ggatgagaca tgccctgacc 4260
ctggccaaga gggcacgcga tgagagggag gtgcctgtgg gagccgtgct ggtgctgaac 4320
aatagagtga tcggcgaggg ctggaacaga gccatcggcc tgcacgaccc aacagcccat 4380
gccgaaatta tggccctgag acagggcggc ctggtcatgc agaactacag actgattgac 4440
gccaccctgt acgtgacatt cgagccttgc gtgatgtgcg ccggcgccat gatccactct 4500
aggatcggcc gcgtggtgtt tggcgtgagg aacgcaaaaa ccggcgccgc aggctccctg 4560
atggacgtgc tgcactaccc cggcatgaat caccgcgtcg aaattaccga gggaatcctg 4620

-continued

```
gcagatgaat gtgccgccct gctgtgctat ttctttcgga tgcctagaca ggtgttcaat   4680
gctcagaaga aggcccagag ctccaccgac tccggaggat ctagcggagg ctcctctggc   4740
tctgagacac ctggcacaag cgagagcgca acacctgaaa gcagcggggg cagcagcggg   4800
gggtcacgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
ggccgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
```

```
tatccggtaa ctatcgtctt gagtccaacc cggtaagaca cgacttatcg ccactggcag   7020

cagccactgg taacaggatt agcagagcga ggtatgtagg cggtgctaca gagttcttga   7080

agtggtggcc taactacggc tacactagaa gaacagtatt tggtatctgc gctctgctga   7140

agccagttac cttcggaaaa agagttggta gctcttgatc cggcaaacaa accaccgctg   7200

gtagcggtgg tttttttgtt tgcaagcagc agattacgcg cagaaaaaaa ggatctcaag   7260

aagatccttt gatcttttct acggggtctg acactcagtg gaacgaaaac tcacgttaag   7320

ggattttggt catgagatta tcaaaaagga tcttcaccta gatcctttta aattaaaaat   7380

gaagttttaa atcaatctaa agtatatatg agtaaacttg gtctgacagt taccaatgct   7440

taatcagtga ggcacctatc tcagcgatct gtctatttcg ttcatccata gttgcctgac   7500

tccccgtcgt gtagataact acgatacggg agggcttacc atctggcccc agtgctgcaa   7560

tgataccgcg agacccacgc tcaccggctc cagatttatc agcaataaac cagccagccg   7620

gaagggccga gcgcagaagt ggtcctgcaa ctttatccgc ctccatccag tctattaatt   7680

gttgccggga agctagagta agtagttcgc cagttaatag tttgcgcaac gttgttgcca   7740

ttgctacagg catcgtggtg tcacgctcgt cgtttggtat ggcttcattc agctccggtt   7800

cccaacgatc aaggcgagtt acatgatccc ccatgttgtg caaaaaagcg gttagctcct   7860

tcggtcctcc gatcgttgtc agaagtaagt tggccgcagt gttatcactc atggttatgg   7920

cagcactgca taattctctt actgtcatgc catccgtaag atgcttttct gtgactggtg   7980

agtactcaac caagtcattc tgagaatagt gtatgcggcg accgagttgc tcttgcccgg   8040

cgtcaatacg ggataatacc gcgccacata gcagaacttt aaaagtgctc atcattggaa   8100

aacgttcttc ggggcgaaaa ctctcaagga tcttaccgct gttgagatcc agttcgatgt   8160

aacccactcg tgcacccaac tgatcttcag catcttttac tttcaccagc gtttctgggt   8220

gagcaaaaac aggaaggcaa aatgccgcaa aaaagggaat aagggcgaca cggaaatgtt   8280

gaatactcat actcttcctt tttcaatatt attgaagcat ttatcagggt tattgtctca   8340

tgagcggata catatttgaa tgtatttaga aaaataaaca aataggggtt ccgcgcacat   8400

ttccccgaaa agtgccacct gacgtcgacg gatcgggaga tcgatctccc gatcccctag   8460

ggtcgactct cagtacaatc tgctctgatg ccgcatagtt aagccagtat ctgctccctg   8520

cttgtgtgtt ggaggtcgct gagtagtgcg cgagcaaaat ttaagctaca acaaggcaag   8580

gcttgaccga caattgcatg aagaatctgc ttagggttag gcgttttgcg ctgcttcgcg   8640

atgtacgggc cagatatacg cgttgacatt gattattgac tagttattaa tagtaatcaa   8700

ttacggggtc attagttcat agcccatata tggagttccg cgttacataa cttacggtaa   8760

atggcccgcc tggctgaccg cccaacgacc cccgcccatt gacgtcaata atgacgtatg   8820

ttcccatagt aacgccaata gggactttcc attgacgtca atgggtggag tatttacggt   8880

aaactgccca cttggcagta catcaagtgt atc                                8913
```

<210> SEQ ID NO 45
<211> LENGTH: 8868
<212> TYPE: DNA
<213> ORGANISM: Artificial Sequence
<220> FEATURE:
<223> OTHER INFORMATION: pCMV-CE-ABE plasmid

<400> SEQUENCE: 45

```
atatgccaag tacgccccct attgacgtca atgacggtaa atggcccgcc tggcattatg     60

cccagtacat gaccttatgg gactttccta cttggcagta catctacgta ttagtcatcg    120
```

-continued

```
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
```

-continued

```
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga cctctggagg atctagcggt ggttcctctg gaagcgagac accaggcaca   3660
agcgagtccg ccacaccaga gagctccggc ggctcctccg gaggatcctc tgaggtggag   3720
ttttcccacg agtactggat gagacatgcc ctgaccctgg ccaagagggc atgggatgaa   3780
agagaagtcc ccgtgggcgc cgtgctggtg cacaacaata gagtgatcgg agagggatgg   3840
aacaggccaa tcggccgcca cgaccctacc gcacacgcag agatcatggc actgaggcag   3900
ggaggcctgg tcatgcagaa ttaccgcctg atcgatgcca ccctgtatgt gacactggag   3960
ccatgcgtga tgtgcgcagg agcaatgatc cacagcagga tcggaagagt ggtgttcgga   4020
gcacgggacg ccaagaccgg cgcagcaggc tccctgatgg atgtgctgca ccaccccggc   4080
atgaaccacc gggtggagat cacagaggga atcctggcag acgagtgcgc cgccctgctg   4140
agcgatttct ttagaatgcg gagacaggag atcaaggccc agaagaaggc acagagctcc   4200
accgactctg gaggatctag cggcggatcc tctggaagcg agacaccagg cacaagcgag   4260
tccgccacac cagagagctc cggcggctcc tccggaggat cctctgaggt ggagttttcc   4320
cacgagtact ggatgagaca tgccctgacc ctggccaaga gggcacgcga tgagagggag   4380
gtgcctgtgg gagccgtgct ggtgctgaac aatagagtga tcggcgaggg ctggaacaga   4440
gccatcggcc tgcacgaccc aacagcccat gccgaaatta tggccctgag acagggcggc   4500
ctggtcatgc agaactacag actgattgac gccaccctgt acgtgacatt cgagccttgc   4560
gtgatgtgcg ccggcgccat gatccactct aggatcggcc gcgtggtgtt tggcgtgagg   4620
aacgcaaaaa ccggcgccgc aggctccctg atggacgtgc tgcactaccc cggcatgaat   4680
caccgcgtcg aaattaccga gggaatcctg gcagatgaat gtgccgccct gctgtgctat   4740
ttctttcgga tgcctagaca ggtgttcaat gctcagaaga aggcccagag ctccaccgac   4800
tccggaggat ctagcggagg ctcctctggc tctgagacac ctggcacaag cgagagcgca   4860
```

```
acacctgaaa gcagcggggg cagcagcggg gggtcagaga caaacggcga aaccggggag   4920
atcgtgtggg ataagggccg ggattttgcc accgtgcgga aagtgctgag catgccccaa   4980
gtgaatatcg tgaaaaagac cgaggtgcag acaggcggct tcagcaaaga gtctatcctg   5040
cccaagagga acagcgataa gctgatcgcc agaaagaagg actgggaccc taagaagtac   5100
ggcggcttcg acagccccac cgtggcctat tctgtgctgg tggtggccaa agtggaaaag   5160
ggcaagtcca agaaactgaa gagtgtgaaa gagctgctgg ggatcaccat catggaaaga   5220
agcagcttcg agaagaatcc catcgacttt ctggaagcca agggctacaa agaagtgaaa   5280
aaggacctga tcatcaagct gcctaagtac tccctgttcg agctggaaaa cggccggaag   5340
agaatgctgg cctctgccgg cgaactgcag aagggaaacg aactggccct gccctccaaa   5400
tatgtgaact tcctgtacct ggccagccac tatgagaagc tgaagggctc ccccgaggat   5460
aatgagcaga aacagctgtt tgtggaacag cacaagcact acctggacga gatcatcgag   5520
cagatcagcg agttctccaa gagagtgatc ctggccgacg ctaatctgga caaagtgctg   5580
tccgcctaca acaagcaccg ggataagccc atcagagagc aggccgagaa tatcatccac   5640
ctgtttaccc tgaccaatct gggagcccct gccgccttca agtactttga caccaccatc   5700
gaccggaaga ggtacaccag caccaaagag gtgctggacg ccaccctgat ccaccagagc   5760
atcaccggcc tgtacgagac acggatcgac ctgtctcagc tgggaggtga ctctggcggc   5820
tcaaaaagaa ccgccgacgg cagcgaattc gagcccaaga agaagaggaa agtctaaccg   5880
gtcatcatca ccatcaccat tgagtttaaa cccgctgatc agcctcgact gtgccttcta   5940
gttgccagcc atctgttgtt tgcccctccc ccgtgccttc cttgaccctg gaaggtgcca   6000
ctcccactgt cctttcctaa taaaatgagg aaattgcatc gcattgtctg agtaggtgtc   6060
attctattct ggggggtggg gtggggcagg acagcaaggg ggaggattgg gaagacaata   6120
gcaggcatgc tggggatgcg gtgggctcta tggcttctga ggcggaaaga accagctggg   6180
gctcgatacc gtcgacctct agctagagct tggcgtaatc atggtcatag ctgtttcctg   6240
tgtgaaattg ttatccgctc acaattccac acaacatacg agccggaagc ataaagtgta   6300
aagcctaggg tgcctaatga gtgagctaac tcacattaat tgcgttgcgc tcactgcccg   6360
ctttccagtc gggaaacctg tcgtgccagc tgcattaatg aatcggccaa cgcgcgggga   6420
gaggcggttt gcgtattggg cgctcttccg cttcctcgct cactgactcg ctgcgctcgg   6480
tcgttcggct gcggcgagcg gtatcagctc actcaaaggc ggtaatacgg ttatccacag   6540
aatcagggga taacgcagga aagaacatgt gagcaaaagg ccagcaaaag gccaggaacc   6600
gtaaaaaggc cgcgttgctg gcgtttttcc ataggctccg cccccctgac gagcatcaca   6660
aaaatcgacg ctcaagtcag aggtggcgaa acccgacagg actataaaga taccaggcgt   6720
ttccccctgg aagctccctc gtgcgctctc ctgttccgac cctgccgctt accggatacc   6780
tgtccgcctt tctcccttcg ggaagcgtgg cgctttctca tagctcacgc tgtaggtatc   6840
tcagttcggt gtaggtcgtt cgctccaagc tgggctgtgt gcacgaaccc cccgttcagc   6900
ccgaccgctg cgccttatcc ggtaactatc gtcttgagtc caacccggta agacacgact   6960
tatcgccact ggcagcagcc actggtaaca ggattagcag agcgaggtat gtaggcggtg   7020
ctacagagtt cttgaagtgg tggcctaact acggctacac tagaagaaca gtatttggta   7080
tctgcgctct gctgaagcca gttaccttcg gaaaaagagt tggtagctct tgatccggca   7140
aacaaaccac cgctggtagc ggtggttttt ttgtttgcaa gcagcagatt acgcgcagaa   7200
```

aaaaaggatc tcaagaagat cctttgatct tttctacggg gtctgacact cagtggaacg 7260
aaaactcacg ttaagggatt ttggtcatga gattatcaaa aaggatcttc acctagatcc 7320
ttttaaatta aaaatgaagt tttaaatcaa tctaaagtat atatgagtaa acttggtctg 7380
acagttacca atgcttaatc agtgaggcac ctatctcagc gatctgtcta tttcgttcat 7440
ccatagttgc ctgactcccc gtcgtgtaga taactacgat acgggagggc ttaccatctg 7500
gccccagtgc tgcaatgata ccgcgagacc cacgctcacc ggctccagat ttatcagcaa 7560
taaaccagcc agccggaagg gccgagcgca gaagtggtcc tgcaacttta tccgcctcca 7620
tccagtctat taattgttgc cgggaagcta gagtaagtag ttcgccagtt aatagtttgc 7680
gcaacgttgt tgccattgct acaggcatcg tggtgtcacg ctcgtcgttt ggtatggctt 7740
cattcagctc cggttcccaa cgatcaaggc gagttacatg atcccccatg ttgtgcaaaa 7800
aagcggttag ctccttcggt cctccgatcg ttgtcagaag taagttggcc gcagtgttat 7860
cactcatggt tatggcagca ctgcataatt ctcttactgt catgccatcc gtaagatgct 7920
tttctgtgac tggtgagtac tcaaccaagt cattctgaga atagtgtatg cggcgaccga 7980
gttgctcttg cccggcgtca atacgggata ataccgcgcc acatagcaga actttaaaag 8040
tgctcatcat tggaaaacgt tcttcggggc gaaaactctc aaggatctta ccgctgttga 8100
gatccagttc gatgtaaccc actcgtgcac ccaactgatc ttcagcatct tttactttca 8160
ccagcgtttc tgggtgagca aaaacaggaa ggcaaaatgc cgcaaaaaag ggaataaggg 8220
cgacacggaa atgttgaata ctcatactct tcctttttca atattattga agcatttatc 8280
agggttattg tctcatgagc ggatacatat ttgaatgtat ttagaaaaat aaacaaatag 8340
gggttccgcg cacatttccc cgaaaagtgc cacctgacgt cgacggatcg ggagatcgat 8400
ctcccgatcc cctagggtcg actctcagta caatctgctc tgatgccgca tagttaagcc 8460
agtatctgct ccctgcttgt gtgttggagg tcgctgagta gtgcgcgagc aaaatttaag 8520
ctacaacaag gcaaggcttg accgacaatt gcatgaagaa tctgcttagg gttaggcgtt 8580
ttgcgctgct tcgcgatgta cgggccagat atacgcgttg acattgatta ttgactagtt 8640
attaatagta atcaattacg gggtcattag ttcatagccc atatatggag ttccgcgtta 8700
cataacttac ggtaaatggc ccgcctggct gaccgcccaa cgacccccgc ccattgacgt 8760
caataatgac gtatgttccc atagtaacgc caatagggac tttccattga cgtcaatggg 8820
tggagtattt acggtaaact gcccacttgg cagtacatca agtgtatc 8868

<210> SEQ ID NO 46
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 46
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420

-continued

```
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
```

agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
tttttcaaga ccgagattac cctggccaac ggcgagatcc ggaagcggcc tctgatcgag 3660
acaaacggcg aaaccgggga gatctctgga ggatctagcg gtggttcctc tggaagcgag 3720
acaccaggca caagcgagtc cgccacacca gagagctccg gcggctcctc cggaggatcc 3780
tctgaggtgg agttttccca cgagtactgg atgagacatg ccctgaccct ggccaagagg 3840
gcatgggatg aaagagaagt ccccgtgggc gccgtgctgg tgcacaacaa tagagtgatc 3900
ggagagggat ggaacaggcc aatcggccgc cacgacccta ccgcacacgc agagatcatg 3960
gcactgaggc agggaggcct ggtcatgcag aattaccgcc tgatcgatgc caccctgtat 4020
gtgacactgg agccatgcgt gatgtgcgca ggagcaatga tccacagcag gatcggaaga 4080
gtggtgttcg gagcacggga cgccaagacc ggcgcagcag gctccctgat ggatgtgctg 4140
caccaccccg gcatgaacca ccgggtggag atcacagagg gaatcctggc agacgagtgc 4200
gccgccctgc tgagcgattt ctttagaatg cggagacagg agatcaaggc ccagaagaag 4260
gcacagagct ccaccgactc tggaggatct agcggcggat cctctggaag cgagacacca 4320
ggcacaagcg agtccgccac accagagagc tccggcggct cctccggagg atcctctgag 4380
gtggagtttt cccacgagta ctggatgaga catgccctga ccctggccaa gagggcacgc 4440
gatgagaggg aggtgcctgt gggagccgtg ctggtgctga acaatagagt gatcggcgag 4500
ggctggaaca gagccatcgg cctgcacgac ccaacagccc atgccgaaat tatggccctg 4560
agacagggcg gcctggtcat gcagaactac agactgattg acgccaccct gtacgtgaca 4620
ttcgagcctt gcgtgatgtg cgccggcgcc atgatccact ctaggatcgg ccgcgtggtg 4680
tttggcgtga ggaacgcaaa aaccggcgcc gcaggctccc tgatggacgt gctgcactac 4740
cccggcatga atcaccgcgt cgaaattacc gagggaatcc tggcagatga atgtgccgcc 4800
ctgctgtgct atttctttcg gatgcctaga caggtgttca atgctcagaa gaaggcccag 4860
agctccaccg actccggagg atctagcgga ggctcctctg gctctgagac acctggcaca 4920
agcgagagcg caacacctga aagcagcggg ggcagcagcg gggggtcagt gtgggataag 4980
ggccgggatt ttgccaccgt gcggaaagtg ctgagcatgc cccaagtgaa tatcgtgaaa 5040
aagaccgagg tgcagacagg cggcttcagc aaagagtcta tcctgcccaa gaggaacagc 5100
gataagctga tcgccagaaa gaaggactgg gaccctaaga agtacggcgg cttcgacagc 5160

-continued

```
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
```

```
tccccgtcgt gtagataact acgatacggg agggcttacc atctggcccc agtgctgcaa   7560

tgataccgcg agacccacgc tcaccggctc cagatttatc agcaataaac cagccagccg   7620

gaagggccga gcgcagaagt ggtcctgcaa ctttatccgc ctccatccag tctattaatt   7680

gttgccggga agctagagta agtagttcgc cagttaatag tttgcgcaac gttgttgcca   7740

ttgctacagg catcgtggtg tcacgctcgt cgtttggtat ggcttcattc agctccggtt   7800

cccaacgatc aaggcgagtt acatgatccc ccatgttgtg caaaaaagcg gttagctcct   7860

tcggtcctcc gatcgttgtc agaagtaagt tggccgcagt gttatcactc atggttatgg   7920

cagcactgca taattctctt actgtcatgc catccgtaag atgcttttct gtgactggtg   7980

agtactcaac caagtcattc tgagaatagt gtatgcggcg accgagttgc tcttgcccgg   8040

cgtcaatacg ggataatacc gcgccacata gcagaacttt aaaagtgctc atcattggaa   8100

aacgttcttc ggggcgaaaa ctctcaagga tcttaccgct gttgagatcc agttcgatgt   8160

aacccactcg tgcacccaac tgatcttcag catcttttac tttcaccagc gtttctgggt   8220

gagcaaaaac aggaaggcaa aatgccgcaa aaaagggaat aagggcgaca cggaaatgtt   8280

gaatactcat actcttcctt tttcaatatt attgaagcat ttatcagggt tattgtctca   8340

tgagcggata catatttgaa tgtatttaga aaaataaaca aataggggtt ccgcgcacat   8400

ttccccgaaa agtgccacct gacgtcgacg gatcgggaga tcgatctccc gatcccctag   8460

ggtcgactct cagtacaatc tgctctgatg ccgcatagtt aagccagtat ctgctccctg   8520

cttgtgtgtt ggaggtcgct gagtagtgcg cgagcaaaat ttaagctaca acaaggcaag   8580

gcttgaccga caattgcatg aagaatctgc ttagggttag gcgttttgcg ctgcttcgcg   8640

atgtacgggc cagatatacg cgttgacatt gattattgac tagttattaa tagtaatcaa   8700

ttacggggtc attagttcat agcccatata tggagttccg cgttacataa cttacggtaa   8760

atggcccgcc tggctgaccg cccaacgacc cccgcccatt gacgtcaata atgacgtatg   8820

ttcccatagt aacgccaata gggactttcc attgacgtca atgggtggag tatttacggt   8880

aaactgccca cttggcagta catcaagtgt atc                                8913


<210> SEQ ID NO 47
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 47

atatgccaag tacgcccct attgacgtca atgacggtaa atggcccgcc tggcattatg     60

cccagtacat gaccttatgg gactttccta cttggcagta catctacgta ttagtcatcg    120

ctattaccat ggtgatgcgg ttttggcagt acatcaatgg gcgtggatag cggtttgact    180

cacggggatt tccaagtctc caccccattg acgtcaatgg gagtttgttt tggcaccaaa    240

atcaacggga ctttccaaaa tgtcgtaaca actccgcccc attgacgcaa atgggcggta    300

ggcgtgtacg gtgggaggtc tatataagca gagctggttt agtgaaccgt cagatccgct    360

agagatccgc ggccgctaat acgactcact atagggagag ccgccaccat gaaacggaca    420

gccgacggaa gcgagttcga gtcaccaaag aagaagcgga aagtcagcag tgacaagaag    480

tacagcatcg gcctggccat cggcaccaac tctgtgggct gggccgtgat caccgacgag    540

tacaaggtgc ccagcaagaa attcaaggtg ctgggcaaca ccgaccggca cagcatcaag    600

aagaacctga tcggagccct gctgttcgac agcggcgaaa cagccgaggc cacccggctg    660
```

-continued

```
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga    1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
```

-continued

```
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtct ggaggatcta gcggtggttc ctctggaagc   3720
gagacaccag gcacaagcga gtccgccaca ccagagagct ccggcggctc ctccggagga   3780
tcctctgagg tggagttttc ccacgagtac tggatgagac atgccctgac cctggccaag   3840
agggcatggg atgaaagaga agtccccgtg ggcgccgtgc tggtgcacaa caatagagtg   3900
atcggagagg gatggaacag gccaatcggc cgccacgacc ctaccgcaca cgcagagatc   3960
atggcactga ggcagggagg cctggtcatg cagaattacc gcctgatcga tgccaccctg   4020
tatgtgacac tggagccatg cgtgatgtgc gcaggagcaa tgatccacag caggatcgga   4080
agagtggtgt tcggagcacg ggacgccaag accggcgcag caggctccct gatggatgtg   4140
ctgcaccacc ccggcatgaa ccaccgggtg gagatcacag agggaatcct ggcagacgag   4200
tgcgccgccc tgctgagcga tttctttaga atgcggagac aggagatcaa ggcccagaag   4260
aaggcacaga gctccaccga ctctggagga tctagcggcg gatcctctgg aagcgagaca   4320
ccaggcacaa gcgagtccgc cacaccagag agctccggcg gctcctccgg aggatcctct   4380
gaggtggagt tttcccacga gtactggatg agacatgccc tgaccctggc caagagggca   4440
cgcgatgaga gggaggtgcc tgtgggagcc gtgctggtgc tgaacaatag agtgatcggc   4500
gagggctgga acagagccat cggcctgcac gacccaacag cccatgccga aattatggcc   4560
ctgagacagg gcggcctggt catgcagaac tacagactga ttgacgccac cctgtacgtg   4620
acattcgagc cttgcgtgat gtgcgccggc gccatgatcc actctaggat cggccgcgtg   4680
gtgtttggcg tgaggaacgc aaaaaccggc gccgcaggct ccctgatgga cgtgctgcac   4740
taccccggca tgaatcaccg cgtcgaaatt accgagggaa tcctggcaga tgaatgtgcc   4800
gccctgctgt gctatttctt tcggatgcct agacaggtgt tcaatgctca gaagaaggcc   4860
cagagctcca ccgactccgg aggatctagc ggaggctcct ctggctctga gacacctggc   4920
acaagcgaga gcgcaacacc tgaaagcagc gggggcagca gcgggggggtc atgggataag   4980
ggccgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaaagaag tgaaaaagga cctgatcatc   5340
aagctgccta agtactccct gttcgagctg gaaaacggcc ggaagagaat gctggcctct   5400
```

gccggcgaac tgcagaaggg aaacgaactg gccctgccct ccaaatatgt gaacttcctg 5460
tacctggcca gccactatga gaagctgaag ggctcccccg aggataatga gcagaaacag 5520
ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg gaagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740

-continued ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 48
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 48
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gccccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240

-continued

```
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggcct ctggaggatc tagcggtggt tcctctggaa gcgagacacc aggcacaagc   4200
gagtccgcca caccagagag ctccggcggc tcctccggag gatcctctga ggtggagttt   4260
tcccacgagt actggatgag acatgccctg accctggcca agagggcatg ggatgaaaga   4320
gaagtccccg tgggcgccgt gctggtgcac aacaatagag tgatcggaga gggatggaac   4380
aggccaatcg gccgccacga ccctaccgca cacgcagaga tcatggcact gaggcaggga   4440
ggcctggtca tgcagaatta ccgcctgatc gatgccaccc tgtatgtgac actggagcca   4500
tgcgtgatgt gcgcaggagc aatgatccac agcaggatcg gaagagtggt gttcggagca   4560
cgggacgcca agaccggcgc agcaggctcc ctgatggatg tgctgcacca ccccggcatg   4620
aaccaccggg tggagatcac agagggaatc ctggcagacg agtgcgccgc cctgctgagc   4680
gatttcttta gaatgcggag acaggagatc aaggcccaga agaaggcaca gagctccacc   4740
gactctggag gatctagcgg cggatcctct ggaagcgaga caccaggcac aagcgagtcc   4800
gccacaccag agagctccgg cggctcctcc ggaggatcct ctgaggtgga gttttcccac   4860
gagtactgga tgagacatgc cctgaccctg gccaagaggg cacgcgatga gagggaggtg   4920
cctgtgggag ccgtgctggt gctgaacaat agagtgatcg gcgagggctg gaacagagcc   4980
atcggcctgc acgacccaac agcccatgcc gaaattatgg ccctgagaca gggcggcctg   5040
gtcatgcaga actacagact gattgacgcc accctgtacg tgacattcga gccttgcgtg   5100
atgtgcgccg gcgccatgat ccactctagg atcggccgcg tggtgtttgg cgtgaggaac   5160
gcaaaaaccg gcgccgcagg ctccctgatg gacgtgctgc actaccccgg catgaatcac   5220
cgcgtcgaaa ttaccgaggg aatcctggca gatgaatgtg ccgccctgct gtgctatttc   5280
tttcggatgc ctagacaggt gttcaatgct cagaagaagg cccagagctc caccgactcc   5340
ggaggatcta gcggaggctc ctctggctct gagacacctg gcacaagcga gagcgcaaca   5400
cctgaaagca gcgggggcag cagcgggggg tcactgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
```

-continued

```
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
```

agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 49
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 49
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140

```
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
```

-continued

```
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagtctg gaggatctag cggtggttcc tctggaagcg agacaccagg cacaagcgag   4260
tccgccacac cagagagctc cggcggctcc tccggaggat cctctgaggt ggagttttcc   4320
cacgagtact ggatgagaca tgccctgacc ctggccaaga gggcatggga tgaaagagaa   4380
gtccccgtgg gcgccgtgct ggtgcacaac aatagagtga tcggagaggg atggaacagg   4440
ccaatcggcc gccacgaccc taccgcacac gcagagatca tggcactgag gcagggaggc   4500
ctggtcatgc agaattaccg cctgatcgat gccaccctgt atgtgacact ggagccatgc   4560
gtgatgtgcg caggagcaat gatccacagc aggatcggaa gagtggtgtt cggagcacgg   4620
gacgccaaga ccggcgcagc aggctccctg atggatgtgc tgcaccaccc cggcatgaac   4680
caccgggtgg agatcacaga gggaatcctg gcagacgagt gcgccgccct gctgagcgat   4740
ttctttagaa tgcggagaca ggagatcaag gcccagaaga aggcacagag ctccaccgac   4800
tctggaggat ctagcggcgg atcctctgga agcgagacac caggcacaag cgagtccgcc   4860
acaccagaga gctccggcgg ctcctccgga ggatcctctg aggtggagtt ttcccacgag   4920
tactggatga gacatgccct gaccctggcc aagagggcac gcgatgagag ggaggtgcct   4980
gtgggagccg tgctggtgct gaacaataga gtgatcggcg agggctggaa cagagccatc   5040
ggcctgcacg acccaacagc ccatgccgaa attatggccc tgagacaggg cggcctggtc   5100
atgcagaact acagactgat tgacgccacc ctgtacgtga cattcgagcc ttgcgtgatg   5160
tgcgccggcg ccatgatcca ctctaggatc ggccgcgtgg tgtttggcgt gaggaacgca   5220
aaaaccggcg ccgcaggctc cctgatggac gtgctgcact accccggcat gaatcaccgc   5280
gtcgaaatta ccgagggaat cctggcagat gaatgtgccg ccctgctgtg ctatttcttt   5340
cggatgccta gacaggtgtt caatgctcag aagaaggccc agagctccac cgactccgga   5400
ggatctagcg gaggctcctc tggctctgag acacctggca caagcgagag cgcaacacct   5460
gaaagcagcg gggcagcag cgggggtca ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
```

-continued

```
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
```

gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 50
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 50
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380

-continued

```
atcctgagag tgaacaccga gatcaccaag gccccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
```

-continued

```
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagggct cctctggagg atctagcggt ggttcctctg gaagcgagac accaggcaca   4260
agcgagtccg ccacaccaga gagctccggc ggctcctccg gaggatcctc tgaggtggag   4320
ttttcccacg agtactggat gagacatgcc ctgaccctgg ccaagagggc atgggatgaa   4380
agagaagtcc ccgtgggcgc cgtgctggtg cacaacaata gagtgatcgg agagggatgg   4440
aacaggccaa tcggccgcca cgaccctacc gcacacgcag agatcatggc actgaggcag   4500
ggaggcctgg tcatgcagaa ttaccgcctg atcgatgcca ccctgtatgt gacactggag   4560
ccatgcgtga tgtgcgcagg agcaatgatc cacagcagga tcggaagagt ggtgttcgga   4620
gcacgggacg ccaagaccgg cgcagcaggc tccctgatgg atgtgctgca ccaccccggc   4680
atgaaccacc gggtggagat cacagaggga atcctggcag acgagtgcgc cgccctgctg   4740
agcgatttct ttagaatgcg gagacaggag atcaaggccc agaagaaggc acagagctcc   4800
accgactctg gaggatctag cggcggatcc tctggaagcg agacaccagg cacaagcgag   4860
tccgccacac cagagagctc cggcggctcc tccggaggat cctctgaggt ggagttttcc   4920
cacgagtact ggatgagaca tgccctgacc ctggccaaga gggcacgcga tgagagggag   4980
gtgcctgtgg gagccgtgct ggtgctgaac aatagagtga tcggcgaggg ctggaacaga   5040
gccatcggcc tgcacgaccc aacagcccat gccgaaatta tggccctgag acagggcggc   5100
ctggtcatgc agaactacag actgattgac gccaccctgt acgtgacatt cgagccttgc   5160
gtgatgtgcg ccggcgccat gatccactct aggatcggcc gcgtggtgtt tggcgtgagg   5220
aacgcaaaaa ccggcgccgc aggctccctg atggacgtgc tgcactaccc cggcatgaat   5280
caccgcgtcg aaattaccga gggaatcctg gcagatgaat gtgccgccct gctgtgctat   5340
ttctttcgga tgcctagaca ggtgttcaat gctcagaaga aggcccagag ctccaccgac   5400
tccggaggat ctagcggagg ctcctctggc tctgagacac ctggcacaag cgagagcgca   5460
acacctgaaa gcagcggggg cagcagcggg gggtcacccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
```

-continued

```
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
```

```
ggtcgactct cagtacaatc tgctctgatg ccgcatagtt aagccagtat ctgctccctg   8520

cttgtgtgtt ggaggtcgct gagtagtgcg cgagcaaaat ttaagctaca acaaggcaag   8580

gcttgaccga caattgcatg aagaatctgc ttagggttag gcgttttgcg ctgcttcgcg   8640

atgtacgggc cagatatacg cgttgacatt gattattgac tagttattaa tagtaatcaa   8700

ttacggggtc attagttcat agcccatata tggagttccg cgttacataa cttacggtaa   8760

atggcccgcc tggctgaccg cccaacgacc cccgcccatt gacgtcaata atgacgtatg   8820

ttcccatagt aacgccaata gggactttcc attgacgtca atgggtggag tatttacggt   8880

aaactgccca cttggcagta catcaagtgt atc                              8913
```

<210> SEQ ID NO 51
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 51

```
atatgccaag tacgccccct attgacgtca atgacggtaa atggcccgcc tggcattatg     60

cccagtacat gaccttatgg gactttccta cttggcagta catctacgta ttagtcatcg    120

ctattaccat ggtgatgcgg ttttggcagt acatcaatgg gcgtggatag cggtttgact    180

cacggggatt tccaagtctc caccccattg acgtcaatgg gagtttgttt tggcaccaaa    240

atcaacggga ctttccaaaa tgtcgtaaca actccgcccc attgacgcaa atgggcggta    300

ggcgtgtacg gtgggaggtc tatataagca gagctggttt agtgaaccgt cagatccgct    360

agagatccgc ggccgctaat acgactcact atagggagag ccgccaccat gaaacggaca    420

gccgacggaa gcgagttcga gtcaccaaag aagaagcgga aagtcagcag tgacaagaag    480

tacagcatcg gcctggccat cggcaccaac tctgtgggct gggccgtgat caccgacgag    540

tacaaggtgc ccagcaagaa attcaaggtg ctgggcaaca ccgaccggca cagcatcaag    600

aagaacctga tcggagccct gctgttcgac agcggcgaaa cagccgaggc cacccggctg    660

aagagaaccg ccagaagaag atacaccaga cggaagaacc ggatctgcta tctgcaagag    720

atcttcagca acgagatggc caaggtggac gacagcttct tccacagact ggaagagtcc    780

ttcctggtgg aagaggataa gaagcacgag cggcacccca tcttcggcaa catcgtggac    840

gaggtggcct accacgagaa gtaccccacc atctaccacc tgagaaagaa actggtggac    900

agcaccgaca aggccgacct gcggctgatc tatctggccc tggcccacat gatcaagttc    960

cggggccact tcctgatcga gggcgacctg aaccccgaca acagcgacgt ggacaagctg   1020

ttcatccagc tggtgcagac ctacaaccag ctgttcgagg aaaaccccat caacgccagc   1080

ggcgtggacg ccaaggccat cctgtctgcc agactgagca agagcagacg gctggaaaat   1140

ctgatcgccc agctgcccgg cgagaagaag aatggcctgt tcggaaacct gattgccctg   1200

agcctgggcc tgacccccaa cttcaagagc aacttcgacc tggccgagga tgccaaactg   1260

cagctgagca aggacaccta cgacgacgac ctggacaacc tgctggccca gatcggcgac   1320

cagtacgccg acctgtttct ggccgccaag aacctgtccg acgccatcct gctgagcgac   1380

atcctgagag tgaacaccga gatcaccaag gccccccctga gcgcctctat gatcaagaga   1440

tacgacgagc accaccagga cctgaccctg ctgaaagctc tcgtgcggca gcagctgcct   1500

gagaagtaca aagagatttt cttcgaccag agcaagaacg gctacgccgg ctacattgac   1560

ggcggagcca gccaggaaga gttctacaag ttcatcaagc ccatcctgga aaagatggac   1620
```

-continued ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
tttttcaaga ccgagattac cctggccaac ggcgagatcc ggaagcggcc tctgatcgag 3660
acaaacggcg aaaccgggga gatcgtgtgg gataagggcc gggattttgc caccgtgcgg 3720
aaagtgctga gcatgcccca agtgaatatc gtgaaaaaga ccgaggtgca gacaggcggc 3780
ttcagcaaag agtctatcct gcccaagagg aacagcgata agctgatcgc cagaaagaag 3840
gactgggacc ctaagaagta cggcggcttc gacagcccca ccgtggccta ttctgtgctg 3900
gtggtggcca aagtggaaaa gggcaagtcc aagaaactga agagtgtgaa agagctgctg 3960

-continued

```
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagggct cccccgagga taatgagtct ggaggatcta gcggtggttc ctctggaagc   4260
gagacaccag gcacaagcga gtccgccaca ccagagagct ccggcggctc ctccggagga   4320
tcctctgagg tggagttttc ccacgagtac tggatgagac atgccctgac cctggccaag   4380
agggcatggg atgaaagaga agtccccgtg ggcgccgtgc tggtgcacaa caatagagtg   4440
atcggagagg gatggaacag gccaatcggc cgccacgacc ctaccgcaca cgcagagatc   4500
atggcactga ggcagggagg cctggtcatg cagaattacc gcctgatcga tgccaccctg   4560
tatgtgacac tggagccatg cgtgatgtgc gcaggagcaa tgatccacag caggatcgga   4620
agagtggtgt tcggagcacg ggacgccaag accggcgcag caggctccct gatggatgtg   4680
ctgcaccacc ccggcatgaa ccaccgggtg gagatcacag agggaatcct ggcagacgag   4740
tgcgccgccc tgctgagcga tttctttaga atgcggagac aggagatcaa ggcccagaag   4800
aaggcacaga gctccaccga ctctggagga tctagcggcg gatcctctgg aagcgagaca   4860
ccaggcacaa gcgagtccgc cacaccagag agctccggcg gctcctccgg aggatcctct   4920
gaggtggagt tttcccacga gtactggatg agacatgccc tgaccctggc caagagggca   4980
cgcgatgaga gggaggtgcc tgtgggagcc gtgctggtgc tgaacaatag agtgatcggc   5040
gagggctgga acagagccat cggcctgcac gacccaacag cccatgccga aattatggcc   5100
ctgagacagg gcggcctggt catgcagaac tacagactga ttgacgccac cctgtacgtg   5160
acattcgagc cttgcgtgat gtgcgccggc gccatgatcc actctaggat cggccgcgtg   5220
gtgtttggcg tgaggaacgc aaaaaccggc gccgcaggct ccctgatgga cgtgctgcac   5280
taccccggca tgaatcaccg cgtcgaaatt accgagggaa tcctggcaga tgaatgtgcc   5340
gccctgctgt gctatttctt tcggatgcct agacaggtgt tcaatgctca gaagaaggcc   5400
cagagctcca ccgactccgg aggatctagc ggaggctcct ctggctctga gacacctggc   5460
acaagcgaga gcgcaacacc tgaaagcagc gggggcagca gcggggggtc acagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
```

aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 52
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 52
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gcccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac attctggaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
tttttcaaga ccgagattac cctggccaac ggcgagatcc ggaagcggcc tctgatcgag 3660
acaaacggcg aaaccgggga gatcgtgtgg gataagggcc gggattttgc caccgtgcgg 3720
aaagtgctga gcatgcccca agtgaatatc gtgaaaaaga ccgaggtgca gacaggcggc 3780
ttcagcaaag agtctatcct gcccaagagg aacagcgata agctgatcgc cagaaagaag 3840
gactgggacc ctaagaagta cggcggcttc gacagcccca ccgtggccta ttctgtgctg 3900
gtggtggcca aagtggaaaa gggcaagtcc aagaaactga agagtgtgaa agagctgctg 3960
gggatcacca tcatggaaag aagcagcttc gagaagaatc ccatcgactt tctggaagcc 4020
aagggctaca aagaagtgaa aaaggacctg atcatcaagc tgcctaagta ctccctgttc 4080
gagctggaaa acggccggaa gagaatgctg gcctctgccg gcgaactgca gaagggaaac 4140
gaactggccc tgccctccaa atatgtgaac ttcctgtacc tggccagcca ctatgagaag 4200

-continued

```
ctgaagggct cccccgagga taatgagcag aaacagctgt ttgtggaatc tggaggatct   4260
agcggtggtt cctctggaag cgagacacca ggcacaagcg agtccgccac accagagagc   4320
tccggcggct cctccggagg atcctctgag gtggagtttt cccacgagta ctggatgaga   4380
catgccctga ccctggccaa gagggcatgg gatgaaagag aagtccccgt gggcgccgtg   4440
ctggtgcaca acaatagagt gatcggagag ggatggaaca ggccaatcgg ccgccacgac   4500
cctaccgcac acgcagagat catggcactg aggcagggag gcctggtcat gcagaattac   4560
cgcctgatcg atgccaccct gtatgtgaca ctggagccat gcgtgatgtg cgcaggagca   4620
atgatccaca gcaggatcgg aagagtggtg ttcggagcac gggacgccaa gaccggcgca   4680
gcaggctccc tgatggatgt gctgcaccac cccggcatga accaccgggt ggagatcaca   4740
gagggaatcc tggcagacga gtgcgccgcc ctgctgagcg atttctttag aatgcggaga   4800
caggagatca aggcccagaa gaaggcacag agctccaccg actctggagg atctagcggc   4860
ggatcctctg gaagcgagac accaggcaca agcgagtccg ccacaccaga gagctccggc   4920
ggctcctccg gaggatcctc tgaggtggag ttttcccacg agtactggat gagacatgcc   4980
ctgaccctgg ccaagagggc acgcgatgag agggaggtgc ctgtgggagc cgtgctggtg   5040
ctgaacaata gagtgatcgg cgagggctgg aacagagcca tcggcctgca cgacccaaca   5100
gcccatgccg aaattatggc cctgagacag ggcggcctgg tcatgcagaa ctacagactg   5160
attgacgcca ccctgtacgt gacattcgag ccttgcgtga tgtgcgccgg cgccatgatc   5220
cactctagga tcggccgcgt ggtgtttggc gtgaggaacg caaaaaccgg cgccgcaggc   5280
tccctgatgg acgtgctgca ctaccccggc atgaatcacc gcgtcgaaat taccgaggga   5340
atcctggcag atgaatgtgc cgccctgctg tgctatttct ttcggatgcc tagacaggtg   5400
ttcaatgctc agaagaaggc ccagagctcc accgactccg gaggatctag cggaggctcc   5460
tctggctctg agacacctgg cacaagcgag agcgcaacac ctgaaagcag cgggggcagc   5520
agcgggggggt cacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
```

```
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913
```

<210> SEQ ID NO 53
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 53
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
ttcctggtgg aagaggataa gaagcacgag cggcacccca tcttcggcaa catcgtggac 840
gaggtggcct accacgagaa gtaccccacc atctaccacc tgagaaagaa actggtggac 900
agcaccgaca aggccgacct gcggctgatc tatctggccc tggcccacat gatcaagttc 960
cggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gcccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100

-continued

```
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacacccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagggct cccccgagga taatgagcag aaacagctgt ttgtggaaca gcacaagtct   4260
ggaggatcta gcggtggttc ctctggaagc gagacaccag gcacaagcga gtccgccaca   4320
ccagagagct ccggcggctc ctccggagga tcctctgagg tggagttttc ccacgagtac   4380
tggatgagac atgccctgac cctggccaag agggcatggg atgaaagaga agtccccgtg   4440
```

-continued

```
ggcgccgtgc tggtgcacaa caatagagtg atcggagagg gatggaacag gccaatcggc   4500
cgccacgacc ctaccgcaca cgcagagatc atggcactga ggcagggagg cctggtcatg   4560
cagaattacc gcctgatcga tgccaccctg tatgtgacac tggagccatg cgtgatgtgc   4620
gcaggagcaa tgatccacag caggatcgga agagtggtgt tcggagcacg ggacgccaag   4680
accggcgcag caggctccct gatggatgtg ctgcaccacc ccggcatgaa ccaccgggtg   4740
gagatcacag agggaatcct ggcagacgag tgcgccgccc tgctgagcga tttctttaga   4800
atgcggagac aggagatcaa ggcccagaag aaggcacaga gctccaccga ctctggagga   4860
tctagcggcg gatcctctgg aagcgagaca ccaggcacaa gcgagtccgc cacaccagag   4920
agctccggcg gctcctccgg aggatcctct gaggtggagt ttcccacgga gtactggatg   4980
agacatgccc tgaccctggc caagagggca cgcgatgaga gggaggtgcc tgtgggagcc   5040
gtgctggtgc tgaacaatag agtgatcggc gagggctgga acagagccat cggcctgcac   5100
gacccaacag cccatgccga aattatggcc ctgagacagg gcggcctggt catgcagaac   5160
tacagactga ttgacgccac cctgtacgtg acattcgagc cttgcgtgat gtgcgccggc   5220
gccatgatcc actctaggat cggccgcgtg gtgtttggcg tgaggaacgc aaaaaccggc   5280
gccgcaggct ccctgatgga cgtgctgcac taccccggca tgaatcaccg cgtcgaaatt   5340
accgagggaa tcctggcaga tgaatgtgcc gccctgctgt gctatttctt tcggatgcct   5400
agacaggtgt tcaatgctca gaagaaggcc cagagctcca ccgactccgg aggatctagc   5460
ggaggctcct ctggctctga gacacctggc acaagcgaga gcgcaacacc tgaaagcagc   5520
gggggcagca gcgggggtc acactacctg gacgagatca tcgagcagat cagcgagttc    5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
```

cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 54
<211> LENGTH: 8913
<212> TYPE: DNA
<213> ORGANISM: Artificial Sequence
<220> FEATURE:
<223> OTHER INFORMATION: pCMV-CE-ABE plasmid -continued

<400> SEQUENCE: 54

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
```

```
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagggct cccccgagga taatgagcag aaacagctgt ttgtggaaca gcacaagcac   4260
tacctggacg agatcatcga gcagatcagc gagttctctg gaggatctag cggtggttcc   4320
tctggaagcg agacaccagg cacaagcgag tccgccacac cagagagctc cggcggctcc   4380
tccggaggat cctctgaggt ggagttttcc cacgagtact ggatgagaca tgccctgacc   4440
ctggccaaga gggcatggga tgaaagagaa gtccccgtgg gcgccgtgct ggtgcacaac   4500
aatagagtga tcggagaggg atggaacagg ccaatcggcc gccacgaccc taccgcacac   4560
gcagagatca tggcactgag gcagggaggc ctggtcatgc agaattaccg cctgatcgat   4620
gccaccctgt atgtgacact ggagccatgc gtgatgtgcg caggagcaat gatccacagc   4680
```

aggatcggaa gagtggtgtt cggagcacgg gacgccaaga ccggcgcagc aggctccctg 4740
atggatgtgc tgcaccaccc cggcatgaac caccgggtgg agatcacaga gggaatcctg 4800
gcagacgagt gcgccgccct gctgagcgat ttctttagaa tgcggagaca ggagatcaag 4860
gcccagaaga aggcacagag ctccaccgac tctggaggat ctagcggcgg atcctctgga 4920
agcgagacac caggcacaag cgagtccgcc acaccagaga gctccggcgg ctcctccgga 4980
ggatcctctg aggtggagtt ttcccacgag tactggatga gacatgccct gaccctggcc 5040
aagagggcac gcgatgagag ggaggtgcct gtgggagccg tgctggtgct gaacaataga 5100
gtgatcggcg agggctggaa cagagccatc ggcctgcacg acccaacagc ccatgccgaa 5160
attatggccc tgagacaggg cggcctggtc atgcagaact acagactgat tgacgccacc 5220
ctgtacgtga cattcgagcc ttgcgtgatg tgcgccggcg ccatgatcca ctctaggatc 5280
ggccgcgtgg tgtttggcgt gaggaacgca aaaaccggcg ccgcaggctc cctgatggac 5340
gtgctgcact accccggcat gaatcaccgc gtcgaaatta ccgagggaat cctggcagat 5400
gaatgtgccg ccctgctgtg ctatttcttt cggatgccta gacaggtgtt caatgctcag 5460
aagaaggccc agagctccac cgactccgga ggatctagcg gaggctcctc tggctctgag 5520
acacctggca caagcgagag cgcaacacct gaaagcagcg ggggcagcag cgggggggtca 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg gaagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 55
<211> LENGTH: 8913
<212> TYPE: DNA
<213> ORGANISM: Artificial Sequence
<220> FEATURE:
<223> OTHER INFORMATION: pCMV-CE-ABE plasmid

<400> SEQUENCE: 55
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180

-continued

```
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca agagcagacg gctggaaaat   1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
```

aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaagggacag aagaacagcc gcgagagaat gaagcggatc 2820
gaagagggca tcaaagagct gggcagccag atcctgaaag aacaccccgt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
tttttcaaga ccgagattac cctggccaac ggcgagatcc ggaagcggcc tctgatcgag 3660
acaaacggcg aaaccgggga gatcgtgtgg gataagggcc gggattttgc caccgtgcgg 3720
aaagtgctga gcatgcccca agtgaatatc gtgaaaaaga ccgaggtgca gacaggcggc 3780
ttcagcaaag agtctatcct gcccaagagg aacagcgata agctgatcgc cagaaagaag 3840
gactgggacc ctaagaagta cggcggcttc gacagcccca ccgtggccta ttctgtgctg 3900
gtggtggcca aagtggaaaa gggcaagtcc aagaaactga agagtgtgaa agagctgctg 3960
gggatcacca tcatggaaag aagcagcttc gagaagaatc ccatcgactt tctggaagcc 4020
aagggctaca aagaagtgaa aaaggacctg atcatcaagc tgcctaagta ctccctgttc 4080
gagctggaaa acggccggaa gagaatgctg gcctctgccg gcgaactgca gaagggaaac 4140
gaactggccc tgccctccaa atatgtgaac ttcctgtacc tggccagcca ctatgagaag 4200
ctgaagggct cccccgagga taatgagcag aaacagctgt ttgtggaaca gcacaagcac 4260
tacctggacg agatcatcga gcagatcagc gagttctcca agagagtgat cctggccgac 4320
gctaatctgg acaaagtgct gtccgcctac aacaagcacc gggataagcc catctctgga 4380
ggatctagcg gtggttcctc tggaagcgag acaccaggca caagcgagtc cgccacacca 4440
gagagctccg gcggctcctc cggaggatcc tctgaggtgg agttttccca cgagtactgg 4500
atgagacatg ccctgaccct ggccaagagg gcatgggatg aaagagaagt ccccgtgggc 4560
gccgtgctgg tgcacaacaa tagagtgatc ggagagggat ggaacaggcc aatcggccgc 4620
cacgacccta ccgcacacgc agagatcatg gcactgaggc agggaggcct ggtcatgcag 4680
aattaccgcc tgatcgatgc caccctgtat gtgacactgg agccatgcgt gatgtgcgca 4740
ggagcaatga tccacagcag gatcggaaga gtggtgttcg gagcacggga cgccaagacc 4800
ggcgcagcag gctccctgat ggatgtgctg caccaccccg gcatgaacca ccgggtggag 4860
atcacagagg gaatcctggc agacgagtgc gccgccctgc tgagcgattt ctttagaatg 4920

-continued

```
cggagacagg agatcaaggc ccagaagaag gcacagagct ccaccgactc tggaggatct   4980
agcggcggat cctctggaag cgagacacca ggcacaagcg agtccgccac accagagagc   5040
tccggcggct cctccggagg atcctctgag gtggagtttt cccacgagta ctggatgaga   5100
catgccctga ccctggccaa gagggcacgc gatgagaggg aggtgcctgt gggagccgtg   5160
ctggtgctga acaatagagt gatcggcgag ggctggaaca gagccatcgg cctgcacgac   5220
ccaacagccc atgccgaaat tatggccctg agacagggcg gcctggtcat gcagaactac   5280
agactgattg acgccaccct gtacgtgaca ttcgagcctt gcgtgatgtg cgccggcgcc   5340
atgatccact ctaggatcgg ccgcgtggtg tttggcgtga ggaacgcaaa aaccggcgcc   5400
gcaggctccc tgatggacgt gctgcactac cccggcatga atcaccgcgt cgaaattacc   5460
gagggaatcc tggcagatga atgtgccgcc ctgctgtgct atttctttcg gatgcctaga   5520
caggtgttca atgctcagaa gaaggcccag agctccaccg actccggagg atctagcgga   5580
ggctcctctg gctctgagac acctggcaca agcgagagcg caacacctga aagcagcggg   5640
ggcagcagcg gggggtcaag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
```

ggattttggt catgagatta tcaaaaagga tcttcaccta gatcctttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatcccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc 8913

<210> SEQ ID NO 56
<211> LENGTH: 8924
<212> TYPE: DNA
<213> ORGANISM: Artificial Sequence
<220> FEATURE:
<223> OTHER INFORMATION: pCMV-CE-CBE1048-1063 plasmid

<400> SEQUENCE: 56
atatgccaag tacgccccct attgacgtca atgacggtaa atggcccgcc tggcattatg 60
cccagtacat gaccttatgg gactttccta ctggcagtac atctacgtat tagtcatcgc 120
tattaccatg gtgatgcggt tttggcagta catcaatggg cgtggatagc ggtttgactc 180
acggggattt ccaagtctcc accccattga cgtcaatggg agtttgtttt ggcaccaaaa 240
tcaacgggac tttccaaaat gtcgtaacaa ctccgcccca ttgacgcaaa tgggcggtag 300
gcgtgtacgg tgggaggtct atataagcag agctggttta gtgaaccgtc agatccgcta 360
gagatccgcg gccgctaata cgactcacta tagggagagc cgccaccatg aaacggacag 420

-continued

```
ccgacggaag cgagttcgag tcaccaaaga agaagcggaa agtcagcagt gacaagaagt    480
acagcatcgg cctggccatc ggcaccaact ctgtgggctg ggccgtgatc accgacgagt    540
acaaggtgcc cagcaagaaa ttcaaggtgc tgggcaacac cgaccggcac agcatcaaga    600
agaacctgat cggagccctg ctgttcgaca gcggcgaaac agccgaggcc acccggctga    660
agagaaccgc cagaagaaga tacaccagac ggaagaaccg gatctgctat ctgcaagaga    720
tcttcagcaa cgagatggcc aaggtggacg acagcttctt ccacagactg gaagagtcct    780
tcctggtgga agaggataag aagcacgagc ggcaccccat cttcggcaac atcgtggacg    840
aggtggccta ccacgagaag taccccacca tctaccacct gagaaagaaa ctggtggaca    900
gcaccgacaa ggccgacctg cggctgatct atctggccct ggcccacatg atcaagttcc    960
ggggccactt cctgatcgag ggcgacctga accccgacaa cagcgacgtg gacaagctgt   1020
tcatccagct ggtgcagacc tacaaccagc tgttcgagga aaaccccatc aacgccagcg   1080
gcgtggacgc caaggccatc ctgtctgcca gactgagcaa gagcagacgg ctggaaaatc   1140
tgatcgccca gctgcccggc gagaagaaga atggcctgtt cggaaacctg attgccctga   1200
gcctgggcct gacccccaac ttcaagagca acttcgacct ggccgaggat gccaaactgc   1260
agctgagcaa ggacacctac gacgacgacc tggacaacct gctggcccag atcggcgacc   1320
agtacgccga cctgtttctg gccgccaaga acctgtccga cgccatcctg ctgagcgaca   1380
tcctgagagt gaacaccgag atcaccaagg cccccctgag cgcctctatg atcaagagat   1440
acgacgagca ccaccaggac ctgaccctgc tgaaagctct cgtgcggcag cagctgcctg   1500
agaagtacaa agagattttc ttcgaccaga gcaagaacgg ctacgccggc tacattgacg   1560
gcggagccag ccaggaagag ttctacaagt tcatcaagcc catcctggaa aagatggacg   1620
gcaccgagga actgctcgtg aagctgaaca gagaggacct gctgcggaag cagcggacct   1680
tcgacaacgg cagcatcccc caccagatcc acctgggaga gctgcacgcc attctgcggc   1740
ggcaggaaga tttttaccca ttcctgaagg acaaccggga aaagatcgag aagatcctga   1800
ccttccgcat cccctactac gtgggccctc tggccagggg aaacagcaga ttcgcctgga   1860
tgaccagaaa gagcgaggaa accatcaccc cctggaactt cgaggaagtg gtggacaagg   1920
gcgcttccgc ccagagcttc atcgagcgga tgaccaactt cgataagaac ctgcccaacg   1980
agaaggtgct gcccaagcac agcctgctgt acgagtactt caccgtgtat aacgagctga   2040
ccaaagtgaa atacgtgacc gagggaatga gaaagcccgc cttcctgagc ggcgagcaga   2100
aaaaggccat cgtggacctg ctgttcaaga ccaaccggaa agtgaccgtg aagcagctga   2160
aagaggacta cttcaagaaa atcgagtgct tcgactccgt ggaaatctcc ggcgtggaag   2220
atcggttcaa cgcctccctg ggcacatacc acgatctgct gaaaattatc aaggacaagg   2280
acttcctgga caatgaggaa aacgaggaca ttctggaaga tatcgtgctg accctgacac   2340
tgtttgagga cagagagatg atcgaggaac ggctgaaaac ctatgcccac ctgttcgacg   2400
acaaagtgat gaagcagctg aagcggcgga gatacaccgg ctggggcagg ctgagccgga   2460
agctgatcaa cggcatccgg gacaagcagt ccggcaagac aatcctggat ttcctgaagt   2520
ccgacggctt cgccaacaga aacttcatgc agctgatcca cgacgacagc ctgaccttta   2580
aagaggacat ccagaaagcc caggtgtccg gccagggcga tagcctgcac gagcacattg   2640
ccaatctggc cggcagcccc gccattaaga agggcatcct gcagacagtg aaggtggtgg   2700
acgagctcgt gaaagtgatg ggccggcaca agcccgagaa catcgtgatc gaaatggcca   2760
gagagaacca gaccacccag aagggacaga agaacagccg cgagagaatg aagcggatcg   2820
```

aagagggcat caaagagctg ggcagccaga tcctgaaaga acaccccgtg gaaaacaccc 2880
agctgcagaa cgagaagctg tacctgtact acctgcagaa tgggcgggat atgtacgtgg 2940
accaggaact ggacatcaac cggctgtccg actacgatgt ggaccatatc gtgcctcaga 3000
gctttctgaa ggacgactcc atcgacaaca aggtgctgac cagaagcgac aagaaccggg 3060
gcaagagcga caacgtgccc tccgaagagg tcgtgaagaa gatgaagaac tactggcggc 3120
agctgctgaa cgccaagctg attacccaga gaaagttcga caatctgacc aaggccgaga 3180
gaggcggcct gagcgaactg gataaggccg gcttcatcaa gagacagctg gtggaaaccc 3240
ggcagatcac aaagcacgtg gcacagatcc tggactcccg gatgaacact aagtacgacg 3300
agaatgacaa gctgatccgg gaagtgaaag tgatcaccct gaagtccaag ctggtgtccg 3360
atttccggaa ggatttccag ttttacaaag tgcgcgagat caacaactac caccacgccc 3420
acgacgccta cctaaacgcc gtcgtgggaa ccgccctgat caaaaagtac cctaagctgg 3480
aaagcgagtt cgtgtacggc gactacaagg tgtacgacgt gcggaagatg atcgccaaga 3540
gcgagcagga aatcggcaag gctaccgcca agtacttctt ctacagcaac atcatgaact 3600
ttttcaagtc cggatccgag accccaggca cctccgagtc tgccacacct gagagcggaa 3660
gcgaaaccgg accagtggca gtggacccaa ccctgaggag acggattgag ccccatgaat 3720
ttgaagtgtt ctttgaccca agggagctga ggaaggagac atgcctgctg tacgagatca 3780
agtggggcac aagccacaag atctggcgcc acagctccaa gaacaccaca aagcacgtgg 3840
aagtgaattt catcgagaag tttacctccg agcggcactt ctgcccctct accagctgtt 3900
ccatcacatg gtttctgtct tggagccctt gcggcgagtg ttccaaggcc atcaccgagt 3960
tcctgtctca gcaccctaac gtgaccctgg tcatctacgt ggcccggctg tatcaccaca 4020
tggaccagca gaacaggcag ggcctgcgcg atctggtgaa ttctggcgtg accatccaga 4080
tcatgacagc ccccagagtac gactattgct ggcggaactt cgtgaattat ccacctggca 4140
aggaggcaca ctggccaaga tacccacccc tgtggatgaa gctgtatgca ctggagctgc 4200
acgcaggaat cctgggcctg cctccatgtc tgaatatcct gcggagaaag cagccccagc 4260
tgacattttt caccattgct ctgcagtctt gtcactatca gcggctgcct cctcatattc 4320
tgtgggctac aggcctgaag tctggatctg gcagcgagac accaggaaca agcgagtcag 4380
caacaccaga gagcgagaca aacggcgaaa ccggggagat cgtgtgggat aagggccggg 4440
attttgccac cgtgcggaaa gtgctgagca tgccccaagt gaatatcgtg aaaaagaccg 4500
aggtgcagac aggcggcttc agcaaagagt ctatcctgcc caagaggaac agcgataagc 4560
tgatcgccag aaagaaggac tgggacccta agaagtacgg cggcttcgac agccccaccg 4620
tggcctattc tgtgctggtg gtggccaaag tggaaaaggg caagtccaag aaactgaaga 4680
gtgtgaaaga gctgctgggg atcaccatca tggaaagaag cagcttcgag aagaatccca 4740
tcgactttct ggaagccaag ggctacaaag aagtgaaaaa ggacctgatc atcaagctgc 4800
ctaagtactc cctgttcgag ctggaaaacg gccggaagag aatgctggcc tctgccggcg 4860
aactgcagaa gggaaacgaa ctggccctgc cctccaaata tgtgaacttc ctgtacctgg 4920
ccagccacta tgagaagctg aagggctccc ccgaggataa tgagcagaaa cagctgtttg 4980
tggaacagca caagcactac ctggacgaga tcatcgagca gatcagcgag ttctccaaga 5040
gagtgatcct ggccgacgct aatctggaca aagtgctgtc cgcctacaac aagcaccggg 5100
ataagcccat cagagagcag gccgagaata tcatccacct gtttaccctg accaatctgg 5160

-continued

```
gagcccctgc cgccttcaag tactttgaca ccaccatcga ccggaagagg tacaccagca   5220
ccaaagaggt gctggacgcc accctgatcc accagagcat caccggcctg tacgagacac   5280
ggatcgacct gtctcagctg ggaggtgaca gcggcgggag cggcgggagc ggggggagca   5340
ctaatctgag cgacatcatt gagaaggaga ctgggaaaca gctggtcatt caggagtcca   5400
tcctgatgct gcctgaggag gtggaggaag tgatcggcaa caagccagag tctgacatcc   5460
tggtgcacac cgcctacgac gagtccacag atgagaatgt gatgctgctg acctctgacg   5520
cccccgagta taagccttgg gccctggtca tccaggattc taacggcgag aataagatca   5580
agatgctgag cggaggatcc ggaggatctg gaggcagcac caacctgtct gacatcatcg   5640
agaaggagac aggcaagcag ctggtcatcc aggagagcat cctgatgctg cccgaagaag   5700
tcgaagaagt gatcggaaac aagcctgaga gcgatatcct ggtccatacc gcctacgacg   5760
agagtaccga cgaaaatgtg atgctgctga catccgacgc cccagagtat aagccctggg   5820
ctctggtcat ccaggattcc aacggagaga acaaaatcaa aatgctgtct ggcggctcaa   5880
aaagaaccgc cgacggcagc gaattcgagc ccaagaagaa gaggaaagtc taaccggtca   5940
tcatcaccat caccattgag tttaaacccg ctgatcagcc tcgactgtgc cttctagttg   6000
ccagccatct gttgtttgcc cctcccccgt gccttccttg accctggaag gtgccactcc   6060
cactgtcctt tcctaataaa atgaggaaat tgcatcgcat tgtctgagta ggtgtcattc   6120
tattctgggg ggtggggtgg ggcaggacag caagggggag gattgggaag acaatagcag   6180
gcatgctggg gatgcggtgg gctctatggc ttctgaggcg gaaagaacca gctggggctc   6240
gataccgtcg acctctagct agagcttggc gtaatcatgg tcatagctgt ttcctgtgtg   6300
aaattgttat ccgctcacaa ttccacacaa catacgagcc ggaagcataa agtgtaaagc   6360
ctaggatgcc taatgagtga gctaactcac attaattgcg ttgcgctcac tgcccgcttt   6420
ccagtcggga aacctgtcgt gccagctgca ttaatgaatc ggccaacgcg cgggaagagg   6480
cggtttgcgt attgggcgct cttccgcttc ctcgctcact gactcgctgc gctcggtcgt   6540
tcggctgcgg cgagcggtat cagctcactc aaaggcggta atacggttat ccacagaatc   6600
aggggataac gcaggaaaga acatgtgagc aaaaggccag caaaaggcca ggaaccgtaa   6660
aaaggccgcg ttgctggcgt ttttccatag gctccgcccc cctgacgagc atcacaaaaa   6720
tcgacgctca agtcagaggt ggcgaaaccc gacaggacta taaagatacc aggcgtttcc   6780
ccctggaagc tccctcgtgc gctctcctgt tccgaccctg ccgcttaccg gatacctgtc   6840
cgcctttctc ccttcgggaa gcgtggcgct ttctcatagc tcacgctgta ggtatctcag   6900
ttcggtgtag gtcgttcgct ccaagctggg ctgtgtgcac gaaccccccg ttcagcccga   6960
ccgctgcgcc ttatccggta actatcgtct tgagtccaac ccggtaagac acgacttatc   7020
gccactggca gcagccactg gtaacaggat tagcagagcg aggtatgtag gcggtgctac   7080
agagttcttg aagtggtggc ctaactacgg ctacactaga agaacagtat ttggtatctg   7140
cgctctgctg aagccagtta ccttcggaaa aagagttggt agctcttgat ccggcaaaca   7200
aaccaccgct ggtagcggtg gtttttttgt ttgcaagcag cagattacgc gcagaaaaaa   7260
aggatctcaa gaagatcctt tgatcttttc tacggggtct gacactcagt ggaacgaaaa   7320
ctcacgttaa gggattttgg tcatgagatt atcaaaaagg atcttcacct agatcctttt   7380
aaattaaaaa tgaagtttta aatcaatcta aagtatatat gagtaaactt ggtctgacag   7440
ttaccaatgc ttaatcagtg aggcacctat ctcagcgatc tgtctatttc gttcatccat   7500
agttgcctga ctccccgtcg tgtagataac tacgatacgg gagggcttac catctggccc   7560
```

cagtgctgca atgataccgc gagacccacg ctcaccggct ccagatttat cagcaataaa 7620
ccagccagcc ggaagggccg agcgcagaag tggtcctgca actttatccg cctccatcca 7680
gtctattaat tgttgccggg aagctagagt aagtagttcg ccagttaata gtttgcgcaa 7740
cgttgttgcc attgctacag gcatcgtggt gtcacgctcg tcgtttggta tggcttcatt 7800
cagctccggt tcccaacgat caaggcgagt tacatgatcc cccatgttgt gcaaaaaagc 7860
ggttagctcc ttcggtcctc cgatcgttgt cagaagtaag ttggccgcag tgttatcact 7920
catggttatg gcagcactgc ataattctct tactgtcatg ccatccgtaa gatgcttttc 7980
tgtgactggt gagtactcaa ccaagtcatt ctgagaatag tgtatgcggc gaccgagttg 8040
ctcttgcccg gcgtcaatac gggataatac cgcgccacat agcagaactt taaaagtgct 8100
catcattgga aaacgttctt cggggcgaaa actctcaagg atcttaccgc tgttgagatc 8160
cagttcgatg taacccactc gtgcacccaa ctgatcttca gcatctttta ctttcaccag 8220
cgtttctggg tgagcaaaaa caggaaggca aaatgccgca aaaaagggaa taagggcgac 8280
acggaaatgt tgaatactca tactcttcct ttttcaatat tattgaagca tttatcaggg 8340
ttattgtctc atgagcggat acatatttga atgtatttag aaaaataaac aaataggggt 8400
tccgcgcaca tttccccgaa aagtgccacc tgacgtcgac ggatcgggag atcgatctcc 8460
cgatccccta gggtcgactc tcagtacaat ctgctctgat gccgcatagt taagccagta 8520
tctgctccct gcttgtgtgt tggaggtcgc tgagtagtgc gcgagcaaaa tttaagctac 8580
aacaaggcaa ggcttgaccg acaattgcat gaagaatctg cttagggtta ggcgttttgc 8640
gctgcttcgc gatgtacggg ccagatatac gcgttgacat tgattattga ctagttatta 8700
atagtaatca attacggggt cattagttca tagcccatat atggagttcc gcgttacata 8760
acttacggta aatggcccgc ctggctgacc gcccaacgac ccccgcccat tgacgtcaat 8820
aatgacgtat gttcccatag taacgccaat agggactttc cattgacgtc aatgggtgga 8880
gtatttacgg taaactgccc acttggcagt acatcaagtg tatc 8924

<210> SEQ ID NO 57
<211> LENGTH: 23
<212> TYPE: DNA
<213> ORGANISM: Artificial Sequence
<220> FEATURE:
<223> OTHER INFORMATION: Synthetic sequence of site 22

<400> SEQUENCE: 57
ccttcccaga aaacctacca ggg 23

<210> SEQ ID NO 58
<211> LENGTH: 23
<212> TYPE: DNA
<213> ORGANISM: Artificial Sequence
<220> FEATURE:
<223> OTHER INFORMATION: Synthetic sequence of site 23

<400> SEQUENCE: 58
caacccccag agcacggtgg tgg 23

<210> SEQ ID NO 59
<211> LENGTH: 23
<212> TYPE: DNA
<213> ORGANISM: Artificial Sequence
<220> FEATURE:
<223> OTHER INFORMATION: Synthetic sequence of site 24

<400> SEQUENCE: 59
caaatctgtc acattgggta agg 23

<210> SEQ ID NO 60
<211> LENGTH: 23
<212> TYPE: DNA
<213> ORGANISM: Artificial Sequence
<220> FEATURE:
<223> OTHER INFORMATION: Synthetic sequence of site 25

<400> SEQUENCE: 60
acagctgcag agagccctgc agg 23

<210> SEQ ID NO 61
<211> LENGTH: 23
<212> TYPE: DNA
<213> ORGANISM: Artificial Sequence
<220> FEATURE:
<223> OTHER INFORMATION: Synthetic sequence of site 26

<400> SEQUENCE: 61
ttccgcctcc gacctgtggc tgg 23

<210> SEQ ID NO 62
<211> LENGTH: 23
<212> TYPE: DNA
<213> ORGANISM: Artificial Sequence
<220> FEATURE:
<223> OTHER INFORMATION: Synthetic sequence of site 27

<400> SEQUENCE: 62
ttccttcagg ctctgaatct tgg 23

<210> SEQ ID NO 63
<211> LENGTH: 23
<212> TYPE: DNA
<213> ORGANISM: Artificial Sequence
<220> FEATURE:
<223> OTHER INFORMATION: Synthetic sequence of site 28

<400> SEQUENCE: 63
aggccgggag ctggaggagc tgg 23

<210> SEQ ID NO 64
<211> LENGTH: 23
<212> TYPE: DNA
<213> ORGANISM: Artificial Sequence
<220> FEATURE:
<223> OTHER INFORMATION: Synthetic sequence of site 29

<400> SEQUENCE: 64
agagcccccc ctcaaagaga ggg 23

<210> SEQ ID NO 65
<211> LENGTH: 23
<212> TYPE: DNA
<213> ORGANISM: Artificial Sequence
<220> FEATURE:
<223> OTHER INFORMATION: Synthetic sequence of site 30

<400> SEQUENCE: 65
ggagccacag gagccgctgc agg 23

<210> SEQ ID NO 66
<211> LENGTH: 23

<212> TYPE: DNA
<213> ORGANISM: Artificial Sequence
<220> FEATURE:
<223> OTHER INFORMATION: Synthetic sequence of site 31

<400> SEQUENCE: 66
tactcccagg tcctcttcaa ggg 23

<210> SEQ ID NO 67
<211> LENGTH: 23
<212> TYPE: DNA
<213> ORGANISM: Artificial Sequence
<220> FEATURE:
<223> OTHER INFORMATION: Synthetic sequence of site 32

<400> SEQUENCE: 67
ggcccagact gagcacgtga tgg 23

<210> SEQ ID NO 68
<211> LENGTH: 678
<212> TYPE: DNA
<213> ORGANISM: Artificial Sequence
<220> FEATURE:
<223> OTHER INFORMATION: nCas9 replaced with APOBEC1 on 1048-1063

<400> SEQUENCE: 68
gaaaccggac cagtggcagt ggacccaacc ctgaggagac ggattgagcc ccatgaattt 60
gaagtgttct ttgacccaag ggagctgagg aaggagacat gcctgctgta cgagatcaag 120
tggggcacaa gccacaagat ctggcgccac agctccaaga acaccacaaa gcacgtggaa 180
gtgaatttca tcgagaagtt tacctccgag cggcacttct gcccctctac cagctgttcc 240
atcacatggt ttctgtcttg gagcccttgc ggcgagtgtt ccaaggccat caccgagttc 300
ctgtctcagc accctaacgt gaccctggtc atctacgtgg cccggctgta tcaccacatg 360
gaccagcaga acaggcaggg cctgcgcgat ctggtgaatt ctggcgtgac catccagatc 420
atgacagccc cagagtacga ctattgctgg cggaacttcg tgaattatcc acctggcaag 480
gaggcacact ggccaagata cccacccctg tggatgaagc tgtatgcact ggagctgcac 540
gcaggaatcc tgggcctgcc tccatgtctg aatatcctgc ggagaaagca gccccagctg 600
acatttttca ccattgctct gcagtcttgt cactatcagc ggctgcctcc tcatattctg 660
tgggctacag gcctgaag 678

<210> SEQ ID NO 69
<211> LENGTH: 609
<212> TYPE: DNA
<213> ORGANISM: Artificial Sequence
<220> FEATURE:
<223> OTHER INFORMATION: nCas9 replaced with APOBEC3A on 1048-1063

<400> SEQUENCE: 69
atggaagcca gcccagcatc cgggcccaga cacttgatgg atccacacat attcacttcc 60
aactttaaca atggcattgg aaggcataag acctacctgt gctacgaagt ggagcgcctg 120
gacaatggca cctcggtcaa gatggaccag cacaggggct ttctacacaa ccaggctaag 180
aatcttctct gtggctttta cggccgccat gcggagctgc gcttcttgga cctggttcct 240
tctttgcagt tggacccggc ccagatctac agggtcactt ggttcatctc ctggagcccc 300
tgcttctcct ggggctgtgc cggggaagtg cgtgcgttcc ttcaggagaa cacacacgtg 360
agactgcgta tcttcgctgc ccgcatcttt gattacgacc ccctatataa ggaggcactg 420
caaatgctgc gggatgctgg ggcccaagtc tccatcatga cctacgatga atttaagcac 480
tgctgggaca cctttgtgga ccaccaggga tgtcccttcc agccctggga tggactagat 540
gagcacagcc aagccctgag tgggaggctg cgggccattc tccagaatca gggaaacagc 600
ggcagcgag 609

<210> SEQ ID NO 70
<211> LENGTH: 8855
<212> TYPE: DNA
<213> ORGANISM: Artificial Sequence
<220> FEATURE:
<223> OTHER INFORMATION: pCMV-CE-A3A1048-1063 plasmid

<400> SEQUENCE: 70
atatgccaag tacgccccct attgacgtca atgacggtaa atggcccgcc tggcattatg 60
cccagtacat gaccttatgg gactttccta ctggcagtac atctacgtat tagtcatcgc 120
tattaccatg gtgatgcggt tttggcagta catcaatggg cgtggatagc ggtttgactc 180
acggggattt ccaagtctcc accccattga cgtcaatggg agtttgtttt ggcaccaaaa 240
tcaacgggac tttccaaaat gtcgtaacaa ctccgcccca ttgacgcaaa tgggcggtag 300
gcgtgtacgg tgggaggtct atataagcag agctggttta gtgaaccgtc agatccgcta 360
gagatccgcg gccgctaata cgactcacta tagggagagc cgccaccatg aaacggacag 420
ccgacggaag cgagttcgag tcaccaaaga agaagcggaa agtcagcagt gacaagaagt 480
acagcatcgg cctggccatc ggcaccaact ctgtgggctg ggccgtgatc accgacgagt 540
acaaggtgcc cagcaagaaa ttcaaggtgc tgggcaacac cgaccggcac agcatcaaga 600
agaacctgat cggagccctg ctgttcgaca gcggcgaaac agccgaggcc acccggctga 660
agagaaccgc cagaagaaga tacaccagac ggaagaaccg gatctgctat ctgcaagaga 720
tcttcagcaa cgagatggcc aaggtggacg acagcttctt ccacagactg gaagagtcct 780
tcctggtgga agaggataag aagcacgagc ggcaccccat cttcggcaac atcgtggacg 840
aggtggccta ccacgagaag taccccacca tctaccacct gagaaagaaa ctggtggaca 900
gcaccgacaa ggccgacctg cggctgatct atctggccct ggcccacatg atcaagttcc 960
ggggccactt cctgatcgag ggcgacctga accccgacaa cagcgacgtg gacaagctgt 1020
tcatccagct ggtgcagacc tacaaccagc tgttcgagga aaaccccatc aacgccagcg 1080
gcgtggacgc caaggccatc ctgtctgcca gactgagcaa gagcagacgg ctggaaaatc 1140
tgatcgccca gctgcccggc gagaagaaga atggcctgtt cggaaacctg attgccctga 1200
gcctgggcct gacccccaac ttcaagagca acttcgacct ggccgaggat gccaaactgc 1260
agctgagcaa ggacacctac gacgacgacc tggacaacct gctggcccag atcggcgacc 1320
agtacgccga cctgtttctg gccgccaaga acctgtccga cgccatcctg ctgagcgaca 1380
tcctgagagt gaacaccgag atcaccaagg ccccccctgag cgcctctatg atcaagagat 1440
acgacgagca ccaccaggac ctgaccctgc tgaaagctct cgtgcggcag cagctgcctg 1500
agaagtacaa agagattttc ttcgaccaga gcaagaacgg ctacgccggc tacattgacg 1560
gcggagccag ccaggaagag ttctacaagt tcatcaagcc catcctggaa aagatggacg 1620
gcaccgagga actgctcgtg aagctgaaca gagaggacct gctgcggaag cagcggacct 1680
tcgacaacgg cagcatcccc caccagatcc acctgggaga gctgcacgcc attctgcggc 1740
ggcaggaaga tttttaccca ttcctgaagg acaaccggga aaagatcgag aagatcctga 1800
ccttccgcat cccctactac gtgggccctc tggccagggg aaacagcaga ttcgcctgga 1860
tgaccagaaa gagcgaggaa accatcaccc cctggaactt cgaggaagtg gtggacaagg 1920
gcgcttccgc ccagagcttc atcgagcgga tgaccaactt cgataagaac ctgcccaacg 1980
agaaggtgct gcccaagcac agcctgctgt acgagtactt caccgtgtat aacgagctga 2040
ccaaagtgaa atacgtgacc gagggaatga gaaagcccgc cttcctgagc ggcgagcaga 2100
aaaaggccat cgtggacctg ctgttcaaga ccaaccggaa agtgaccgtg aagcagctga 2160
aagaggacta cttcaagaaa atcgagtgct tcgactccgt ggaaatctcc ggcgtggaag 2220
atcggttcaa cgcctccctg ggcacatacc acgatctgct gaaaattatc aaggacaagg 2280
acttcctgga caatgaggaa aacgaggaca ttctggaaga tatcgtgctg accctgacac 2340
tgtttgagga cagagagatg atcgaggaac ggctgaaaac ctatgcccac ctgttcgacg 2400
acaaagtgat gaagcagctg aagcggcgga gatacaccgg ctggggcagg ctgagccgga 2460
agctgatcaa cggcatccgg gacaagcagt ccggcaagac aatcctggat ttcctgaagt 2520
ccgacggctt cgccaacaga aacttcatgc agctgatcca cgacgacagc ctgaccttta 2580
aagaggacat ccagaaagcc caggtgtccg gccagggcga tagcctgcac gagcacattg 2640
ccaatctggc cggcagcccc gccattaaga agggcatcct gcagacagtg aaggtggtgg 2700
acgagctcgt gaaagtgatg ggccggcaca agcccgagaa catcgtgatc gaaatggcca 2760
gagagaacca gaccacccag aagggacaga agaacagccg cgagagaatg aagcggatcg 2820
aagagggcat caaagagctg ggcagccaga tcctgaaaga acaccccgtg gaaaacaccc 2880
agctgcagaa cgagaagctg tacctgtact acctgcagaa tgggcgggat atgtacgtgg 2940
accaggaact ggacatcaac cggctgtccg actacgatgt ggaccatatc gtgcctcaga 3000
gctttctgaa ggacgactcc atcgacaaca aggtgctgac cagaagcgac aagaaccggg 3060
gcaagagcga caacgtgccc tccgaagagg tcgtgaagaa gatgaagaac tactggcggc 3120
agctgctgaa cgccaagctg attacccaga gaaagttcga caatctgacc aaggccgaga 3180
gaggcggcct gagcgaactg gataaggccg gcttcatcaa gagacagctg gtggaaaccc 3240
ggcagatcac aaagcacgtg gcacagatcc tggactcccg gatgaacact aagtacgacg 3300
agaatgacaa gctgatccgg gaagtgaaag tgatcaccct gaagtccaag ctggtgtccg 3360
atttccggaa ggatttccag ttttacaaag tgcgcgagat caacaactac caccacgccc 3420
acgacgccta cctaaacgcc gtcgtgggaa ccgccctgat caaaaagtac cctaagctgg 3480
aaagcgagtt cgtgtacggc gactacaagg tgtacgacgt gcggaagatg atcgccaaga 3540
gcgagcagga aatcggcaag gctaccgcca agtacttctt ctacagcaac atcatgaact 3600
tttcaagtc cggatccgag accccaggca cctccgagtc tgccacacct gagagcggaa 3660
gcatggaagc cagcccagca tccgggccca gacacttgat ggatccacac atattcactt 3720
ccaactttaa caatggcatt ggaaggcata agacctacct gtgctacgaa gtggagcgcc 3780
tggacaatgg cacctcggtc aagatggacc agcacagggg ctttctacac aaccaggcta 3840
agaatcttct ctgtggcttt tacggccgcc atgcggagct gcgcttcttg gacctggttc 3900
cttctttgca gttggacccg gcccagatct acagggtcac ttggttcatc tcctggagcc 3960
cctgcttctc ctggggctgt gccggggaag tgcgtgcgtt ccttcaggag aacacacacg 4020
tgagactgcg tatcttcgct gcccgcatct ttgattacga cccccctatat aaggaggcac 4080
tgcaaatgct gcgggatgct ggggcccaag tctccatcat gacctacgat gaatttaagc 4140
actgctggga cacctttgtg gaccaccagg gatgtccctt ccagccctgg gatggactag 4200

-continued

```
atgagcacag ccaagccctg agtgggaggc tgcgggccat tctccagaat cagggaaaca   4260
gcggcagcga gtctggatct ggcagcgaga caccaggaac aagcgagtca gcaacaccag   4320
agagcgagac aaacggcgaa accggggaga tcgtgtggga taagggccgg gattttgcca   4380
ccgtgcggaa agtgctgagc atgccccaag tgaatatcgt gaaaaagacc gaggtgcaga   4440
caggcggctt cagcaaagag tctatcctgc ccaagaggaa cagcgataag ctgatcgcca   4500
gaaagaagga ctgggaccct aagaagtacg gcggcttcga cagccccacc gtggcctatt   4560
ctgtgctggt ggtggccaaa gtggaaaagg gcaagtccaa gaaactgaag agtgtgaaag   4620
agctgctggg gatcaccatc atggaaagaa gcagcttcga gaagaatccc atcgactttc   4680
tggaagccaa gggctacaaa gaagtgaaaa aggacctgat catcaagctg cctaagtact   4740
ccctgttcga gctggaaaac ggccggaaga gaatgctggc ctctgccggc gaactgcaga   4800
agggaaacga actggccctg ccctccaaat atgtgaactt cctgtacctg gccagccact   4860
atgagaagct gaagggctcc cccgaggata atgagcagaa acagctgttt gtggaacagc   4920
acaagcacta cctggacgag atcatcgagc agatcagcga gttctccaag agagtgatcc   4980
tggccgacgc taatctggac aaagtgctgt ccgcctacaa caagcaccgg gataagccca   5040
tcagagagca ggccgagaat atcatccacc tgtttaccct gaccaatctg ggagcccctg   5100
ccgccttcaa gtactttgac accaccatcg accggaagag gtacaccagc accaaagagg   5160
tgctggacgc caccctgatc caccagagca tcaccggcct gtacgagaca cggatcgacc   5220
tgtctcagct gggaggtgac agcggcggga gcggcgggag cgggggggagc actaatctga   5280
gcgacatcat tgagaaggag actgggaaac agctggtcat tcaggagtcc atcctgatgc   5340
tgcctgagga ggtggaggaa gtgatcggca acaagccaga gtctgacatc ctggtgcaca   5400
ccgcctacga cgagtccaca gatgagaatg tgatgctgct gacctctgac gcccccgagt   5460
ataagccttg ggccctggtc atccaggatt ctaacggcga gaataagatc aagatgctga   5520
gcggaggatc cggaggatct ggaggcagca ccaacctgtc tgacatcatc gagaaggaga   5580
caggcaagca gctggtcatc caggagagca tcctgatgct gcccgaagaa gtcgaagaag   5640
tgatcggaaa caagcctgag agcgatatcc tggtccatac cgcctacgac gagagtaccg   5700
acgaaaatgt gatgctgctg acatccgacg ccccagagta taagccctgg gctctggtca   5760
tccaggattc caacggagag aacaaaatca aaatgctgtc tggcggctca aaaagaaccg   5820
ccgacggcag cgaattcgag cccaagaaga agaggaaagt ctaaccggtc atcatcacca   5880
tcaccattga gtttaaaccc gctgatcagc ctcgactgtg ccttctagtt gccagccatc   5940
tgttgtttgc ccctcccccg tgccttcctt gaccctggaa ggtgccactc ccactgtcct   6000
ttcctaataa aatgaggaaa ttgcatcgca ttgtctgagt aggtgtcatt ctattctggg   6060
gggtggggtg gggcaggaca gcaaggggga ggattgggaa gacaatagca ggcatgctgg   6120
ggatgcggtg ggctctatgg cttctgaggc ggaaagaacc agctggggct cgataccgtc   6180
gacctctagc tagagcttgg cgtaatcatg gtcatagctg tttcctgtgt gaaattgtta   6240
tccgctcaca attccacaca acatacgagc cggaagcata aagtgtaaag cctaggatgc   6300
ctaatgagtg agctaactca cattaattgc gttgcgctca ctgcccgctt tccagtcggg   6360
aaacctgtcg tgccagctgc attaatgaat cggccaacgc gcgggaagag gcggtttgcg   6420
tattgggcgc tcttccgctt cctcgctcac tgactcgctg cgctcggtcg ttcggctgcg   6480
gcgagcggta tcagctcact caaaggcggt aatacggtta tccacagaat caggggataa   6540
cgcaggaaag aacatgtgag caaaaggcca gcaaaaggcc aggaaccgta aaaaggccgc   6600
```

gttgctggcg tttttccata ggctccgccc ccctgacgag catcacaaaa atcgacgctc 6660
aagtcagagg tggcgaaacc cgacaggact ataaagatac caggcgtttc cccctggaag 6720
ctccctcgtg cgctctcctg ttccgaccct gccgcttacc ggatacctgt ccgcctttct 6780
cccttcggga agcgtggcgc tttctcatag ctcacgctgt aggtatctca gttcggtgta 6840
ggtcgttcgc tccaagctgg gctgtgtgca cgaacccccc gttcagcccg accgctgcgc 6900
cttatccggt aactatcgtc ttgagtccaa cccggtaaga cacgacttat cgccactggc 6960
agcagccact ggtaacagga ttagcagagc gaggtatgta ggcggtgcta cagagttctt 7020
gaagtggtgg cctaactacg gctacactag aagaacagta tttggtatct gcgctctgct 7080
gaagccagtt accttcggaa aaagagttgg tagctcttga tccggcaaac aaaccaccgc 7140
tggtagcggt ggtttttttg tttgcaagca gcagattacg cgcagaaaaa aaggatctca 7200
agaagatcct ttgatctttt ctacggggtc tgacactcag tggaacgaaa actcacgtta 7260
agggattttg gtcatgagat tatcaaaaag gatcttcacc tagatccttt taaattaaaa 7320
atgaagtttt aaatcaatct aaagtatata tgagtaaact tggtctgaca gttaccaatg 7380
cttaatcagt gaggcaccta tctcagcgat ctgtctattt cgttcatcca tagttgcctg 7440
actccccgtc gtgtagataa ctacgatacg ggagggctta ccatctggcc ccagtgctgc 7500
aatgataccg cgagacccac gctcaccggc tccagattta tcagcaataa accagccagc 7560
cggaagggcc gagcgcagaa gtggtcctgc aactttatcc gcctccatcc agtctattaa 7620
ttgttgccgg gaagctagag taagtagttc gccagttaat agtttgcgca acgttgttgc 7680
cattgctaca ggcatcgtgg tgtcacgctc gtcgtttggt atggcttcat tcagctccgg 7740
ttcccaacga tcaaggcgag ttacatgatc ccccatgttg tgcaaaaaag cggttagctc 7800
cttcggtcct ccgatcgttg tcagaagtaa gttggccgca gtgttatcac tcatggttat 7860
ggcagcactg cataattctc ttactgtcat gccatccgta agatgctttt ctgtgactgg 7920
tgagtactca accaagtcat tctgagaata gtgtatgcgg cgaccgagtt gctcttgccc 7980
ggcgtcaata cgggataata ccgcgccaca tagcagaact ttaaaagtgc tcatcattgg 8040
aaaacgttct tcggggcgaa aactctcaag gatcttaccg ctgttgagat ccagttcgat 8100
gtaacccact cgtgcaccca actgatcttc agcatctttt actttcacca gcgtttctgg 8160
gtgagcaaaa acaggaaggc aaaatgccgc aaaaaaggga ataagggcga cacggaaatg 8220
ttgaatactc atactcttcc tttttcaata ttattgaagc atttatcagg gttattgtct 8280
catgagcgga tacatatttg aatgtattta gaaaaataaa caaatagggg ttccgcgcac 8340
atttccccga aaagtgccac ctgacgtcga cggatcggga gatcgatctc ccgatcccct 8400
agggtcgact ctcagtacaa tctgctctga tgccgcatag ttaagccagt atctgctccc 8460
tgcttgtgtg ttggaggtcg ctgagtagtg cgcgagcaaa atttaagcta caacaaggca 8520
aggcttgacc gacaattgca tgaagaatct gcttagggtt aggcgttttg cgctgcttcg 8580
cgatgtacgg gccagatata cgcgttgaca ttgattattg actagttatt aatagtaatc 8640
aattacgggg tcattagttc atagcccata tatggagttc cgcgttacat aacttacggt 8700
aaatggcccg cctggctgac cgcccaacga cccccgccca ttgacgtcaa taatgacgta 8760
tgttcccata gtaacgccaa tagggacttt ccattgacgt caatgggtgg agtatttacg 8820
gtaaactgcc cacttggcag tacatcaagt gtatc 8855

<210> SEQ ID NO 71

<211> LENGTH: 22
<212> TYPE: DNA
<213> ORGANISM: Artificial Sequence
<220> FEATURE:
<223> OTHER INFORMATION: Synthetic forward primer of TadA-TadA* transposon

<400> SEQUENCE: 71
ggtctctgat ccggcgcacg aa 22

<210> SEQ ID NO 72
<211> LENGTH: 22
<212> TYPE: DNA
<213> ORGANISM: Artificial Sequence
<220> FEATURE:
<223> OTHER INFORMATION: Synthetic reverse primer of TadA-TadA* transposon

<400> SEQUENCE: 72
ggtctctgat ccggcgcacg aa 22

<210> SEQ ID NO 73
<211> LENGTH: 22
<212> TYPE: DNA
<213> ORGANISM: Artificial Sequence
<220> FEATURE:
<223> OTHER INFORMATION: Synthetic forward primer of pCMV-ABEmax

<400> SEQUENCE: 73
gacaagaagt acagcatcgg cc 22

<210> SEQ ID NO 74
<211> LENGTH: 37
<212> TYPE: DNA
<213> ORGANISM: Artificial Sequence
<220> FEATURE:
<223> OTHER INFORMATION: Synthetic reverse primer of pCMV-ABEmax

<400> SEQUENCE: 74
gctgtacttc ttgtcactgc tgactttccg cttcttc 37

<210> SEQ ID NO 75
<211> LENGTH: 36
<212> TYPE: DNA
<213> ORGANISM: Artificial Sequence
<220> FEATURE:
<223> OTHER INFORMATION: Synthetic forward primer of a nCas9 fragment

<400> SEQUENCE: 75
gaagaagcgg aaagtcgaca agaagtacag catcgg 36

<210> SEQ ID NO 76
<211> LENGTH: 36
<212> TYPE: DNA
<213> ORGANISM: Artificial Sequence
<220> FEATURE:
<223> OTHER INFORMATION: Synthetic reverse primer of a nCas9 fragment

<400> SEQUENCE: 76
ctgagctagc tgtcaacgag ccccagctgg ttcttt 36

<210> SEQ ID NO 77
<211> LENGTH: 42
<212> TYPE: DNA
<213> ORGANISM: Artificial Sequence
<220> FEATURE:
<223> OTHER INFORMATION: Synthetic forward primer of a KanR fragment

<400> SEQUENCE: 77
ctcactgatt aagcattggt aagcgcggaa cccctatttg tt 42

<210> SEQ ID NO 78
<211> LENGTH: 48
<212> TYPE: DNA
<213> ORGANISM: Artificial Sequence
<220> FEATURE:
<223> OTHER INFORMATION: Synthetic reverse primer of a KanR fragment

<400> SEQUENCE: 78
ccgtttcatg gtggcatgta tatctccttc ttaaagttaa acaaaatt 48

<210> SEQ ID NO 79
<211> LENGTH: 59
<212> TYPE: DNA
<213> ORGANISM: Artificial Sequence
<220> FEATURE:
<223> OTHER INFORMATION: Synthetic forward primer of a U6-sgRNA fragment

<400> SEQUENCE: 79
gtataatact agtgctcttg cccggcgtca atacgtttta gagctagaaa tagcaagtt 59

<210> SEQ ID NO 80
<211> LENGTH: 34
<212> TYPE: DNA
<213> ORGANISM: Artificial Sequence
<220> FEATURE:
<223> OTHER INFORMATION: Synthetic reverse primer of a U6-sgRNA fragment

<400> SEQUENCE: 80
gttagcagcc ggatcaaaaa aagcaccgac tcgg 34

<210> SEQ ID NO 81
<211> LENGTH: 44
<212> TYPE: DNA
<213> ORGANISM: Artificial Sequence
<220> FEATURE:
<223> OTHER INFORMATION: Synthetic forward primer of a J23119promoter-
gRNA fragment

<400> SEQUENCE: 81
ttgacagcta gctcagtcct aggtataata ctagtgctct tgcc 44

<210> SEQ ID NO 82
<211> LENGTH: 34
<212> TYPE: DNA
<213> ORGANISM: Artificial Sequence
<220> FEATURE:
<223> OTHER INFORMATION: Synthetic reverse primer of a J23119promoter-
gRNA fragment

<400> SEQUENCE: 82
gttagcagcc ggatcaaaaa aagcaccgac tcgg 34

<210> SEQ ID NO 83
<211> LENGTH: 35
<212> TYPE: DNA
<213> ORGANISM: Artificial Sequence
<220> FEATURE:
<223> OTHER INFORMATION: Synthetic forward primer of an AmpR-1 fragment

<400> SEQUENCE: 83
cttttcgggg aaatgtggga aatgtgcgcg gaacc 35

<210> SEQ ID NO 84
<211> LENGTH: 20
<212> TYPE: DNA
<213> ORGANISM: Artificial Sequence
<220> FEATURE:
<223> OTHER INFORMATION: Synthetic reverse primer of an AmpR-1 fragment

<400> SEQUENCE: 84
cccggcgtca atacgggata 20

<210> SEQ ID NO 85
<211> LENGTH: 35
<212> TYPE: DNA
<213> ORGANISM: Artificial Sequence
<220> FEATURE:
<223> OTHER INFORMATION: Synthetic forward primer of an AmpR-2 fragment

<400> SEQUENCE: 85
gtattgacgc cgggtaagag caactcggtc gccgc 35

<210> SEQ ID NO 86
<211> LENGTH: 27
<212> TYPE: DNA
<213> ORGANISM: Artificial Sequence
<220> FEATURE:
<223> OTHER INFORMATION: Synthetic reverse primer of an AmpR-2 fragment

<400> SEQUENCE: 86
ttaccaatgc ttaatcagtg aggcacc 27

<210> SEQ ID NO 87
<211> LENGTH: 35
<212> TYPE: DNA
<213> ORGANISM: Artificial Sequence
<220> FEATURE:
<223> OTHER INFORMATION: Synthetic forward primer for positive colonies

<400> SEQUENCE: 87
cttttcgggg aaatgtggga aatgtgcgcg gaacc 35

<210> SEQ ID NO 88
<211> LENGTH: 23
<212> TYPE: DNA
<213> ORGANISM: Artificial Sequence
<220> FEATURE:
<223> OTHER INFORMATION: Synthetic reverse primer for positive colonies

<400> SEQUENCE: 88
cggatgccta gacaggtgtt caa 23

<210> SEQ ID NO 89
<211> LENGTH: 34
<212> TYPE: DNA
<213> ORGANISM: Artificial Sequence
<220> FEATURE:
<223> OTHER INFORMATION: Synthetic forward primer for fragments of CE-ABE

<400> SEQUENCE: 89
agggagagcc gccaccatga aacggacagc cgac 34

<210> SEQ ID NO 90
<211> LENGTH: 37
<212> TYPE: DNA
<213> ORGANISM: Artificial Sequence
<220> FEATURE:

<223> OTHER INFORMATION: Synthetic reverse primer for fragments of
      CE-ABE

<400> SEQUENCE: 90
tcctcttctt cttgggctcg aattcgctgc cgtcggc 37

<210> SEQ ID NO 91
<211> LENGTH: 26
<212> TYPE: DNA
<213> ORGANISM: Artificial Sequence
<220> FEATURE:
<223> OTHER INFORMATION: Synthetic forward primer for the fragment of
      SEQ ID NO: 35

<400> SEQUENCE: 91
ggtggcggct ctccctatag tgagtc 26

<210> SEQ ID NO 92
<211> LENGTH: 26
<212> TYPE: DNA
<213> ORGANISM: Artificial Sequence
<220> FEATURE:
<223> OTHER INFORMATION: Synthetic reverse primer for the fragment of
      SEQ ID NO: 35

<400> SEQUENCE: 92
cccaagaaga agaggaaagt ctaacc 26

<210> SEQ ID NO 93
<211> LENGTH: 37
<212> TYPE: DNA
<213> ORGANISM: Artificial Sequence
<220> FEATURE:
<223> OTHER INFORMATION: Synthetic forward primer of the APOBEC1
      fragment

<400> SEQUENCE: 93
catgaacttt ttcaagtccg gatccgagac cccaggc 37

<210> SEQ ID NO 94
<211> LENGTH: 35
<212> TYPE: DNA
<213> ORGANISM: Artificial Sequence
<220> FEATURE:
<223> OTHER INFORMATION: Synthetic reverse primer of the APOBEC1
      fragment

<400> SEQUENCE: 94
tttcgccgtt tgtctcgctc tctggtgttg ctgac 35

<210> SEQ ID NO 95
<211> LENGTH: 37
<212> TYPE: DNA
<213> ORGANISM: Artificial Sequence
<220> FEATURE:
<223> OTHER INFORMATION: Synthetic forward primer of the APOBEC3A
      fragment

<400> SEQUENCE: 95
catgaacttt ttcaagtccg gatccgagac cccaggc 37

<210> SEQ ID NO 96
<211> LENGTH: 35
<212> TYPE: DNA
<213> ORGANISM: Artificial Sequence
<220> FEATURE:
<223> OTHER INFORMATION: Synthetic reverse primer of the APOBEC3A fragment

<400> SEQUENCE: 96
tttcgccgtt tgtctcgctc tctggtgttg ctgac 35

<210> SEQ ID NO 97
<211> LENGTH: 27
<212> TYPE: DNA
<213> ORGANISM: Artificial Sequence
<220> FEATURE:
<223> OTHER INFORMATION: Synthetic forward primer of the eukaryotic expression vector

<400> SEQUENCE: 97
gagacaaacg gcgaaaccgg ggagatc 27

<210> SEQ ID NO 98
<211> LENGTH: 23
<212> TYPE: DNA
<213> ORGANISM: Artificial Sequence
<220> FEATURE:
<223> OTHER INFORMATION: Synthetic reverse primer of the eukaryotic expression vector

<400> SEQUENCE: 98
cttgaaaaag ttcatgatgt tgc 23

<210> SEQ ID NO 99
<211> LENGTH: 22
<212> TYPE: DNA
<213> ORGANISM: Artificial Sequence
<220> FEATURE:
<223> OTHER INFORMATION: Synthetic forward primer for linearized fragment

<400> SEQUENCE: 99
atgcctgcta ttgtcttccc aa 22

<210> SEQ ID NO 100
<211> LENGTH: 21
<212> TYPE: DNA
<213> ORGANISM: Artificial Sequence
<220> FEATURE:
<223> OTHER INFORMATION: Synthetic reverse primer for linearized fragment

<400> SEQUENCE: 100
aacgggactt tccaaaatgt c 21

<210> SEQ ID NO 101
<211> LENGTH: 24
<212> TYPE: DNA
<213> ORGANISM: Artificial Sequence
<220> FEATURE:
<223> OTHER INFORMATION: Synthetic forward primer for sgRNA

<400> SEQUENCE: 101
tctcgcgcgt ttcggtgatg acgg 24

<210> SEQ ID NO 102
<211> LENGTH: 25
<212> TYPE: DNA
<213> ORGANISM: Artificial Sequence
<220> FEATURE:
<223> OTHER INFORMATION: Synthetic reverse primer for sgRNA

<400> SEQUENCE: 102
aaaaaaatct cgccaacaag ttgac 25

<210> SEQ ID NO 103
<211> LENGTH: 23
<212> TYPE: DNA
<213> ORGANISM: Artificial Sequence
<220> FEATURE:
<223> OTHER INFORMATION: Synthetic forward primer of the fragment of target sites

<400> SEQUENCE: 103
aaagatcttc acaggctacc ccc 23

<210> SEQ ID NO 104
<211> LENGTH: 22
<212> TYPE: DNA
<213> ORGANISM: Artificial Sequence
<220> FEATURE:
<223> OTHER INFORMATION: Synthetic reverse primer of the fragment of target sites

<400> SEQUENCE: 104
aatccacagc aacaccctct cc 22

<210> SEQ ID NO 105
<211> LENGTH: 45
<212> TYPE: PRT
<213> ORGANISM: Artificial Sequence
<220> FEATURE:
<223> OTHER INFORMATION: AmpR X118Q insert site

<400> SEQUENCE: 105

Gly Cys Gly Cys Gly Gly Thr Ala Thr Thr Ala Thr Cys Cys Cys Gly
1 5 10 15

Thr Ala Thr Thr Gly Ala Cys Gly Cys Cys Gly Gly Gly Thr Ala Ala
20 25 30

Gly Ala Gly Cys Ala Ala Cys Thr Cys Gly Gly Thr Cys
35 40 45

<210> SEQ ID NO 106
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_agalactiae

<400> SEQUENCE: 106

Tyr Ser Asn Ile Met Asn Phe Phe Lys Thr Lys Val Thr Leu Ala Asp
1 5 10 15

Gly Thr Val Val Val Lys Asp Asp Ile Glu Val Asn Asn Asp Thr Gly
20 25 30

Glu Ile Val Trp Asp Lys Lys Lys His Phe Ala Thr Val Arg Lys Val
35 40 45

Leu Ser Tyr Pro Gln Val Asn Ile Val Lys
50 55

<210> SEQ ID NO 107
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_mitis

<400> SEQUENCE: 107

Tyr Ser Asn Leu Leu Asn Phe Phe Lys Glu Glu Val His Tyr Ala Asp
1               5                   10                  15

Gly Thr Ile Val Lys Arg Glu Asn Ile Glu Tyr Ser Lys Asp Thr Gly
            20                  25                  30

Glu Ile Ala Trp Asn Lys Glu Lys Asp Phe Ala Thr Ile Lys Lys Val
        35                  40                  45

Leu Ser Phe Pro Gln Val Asn Ile Val Lys
    50                  55

<210> SEQ ID NO 108
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_pseudopneumoniae

<400> SEQUENCE: 108

Tyr Ser Asn Leu Leu Asn Phe Phe Lys Glu Glu Val His Tyr Ala Asp
1               5                   10                  15

Gly Thr Ile Val Lys Arg Glu Asn Ile Glu Tyr Ser Lys Asp Thr Gly
            20                  25                  30

Glu Ile Ala Trp Asn Lys Glu Lys Asp Phe Ala Thr Ile Lys Lys Val
        35                  40                  45

Leu Ser Phe Pro Gln Val Asn Ile Val Lys
    50                  55

<210> SEQ ID NO 109
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_oralis

<400> SEQUENCE: 109

Tyr Ser Asn Leu Leu Asn Phe Phe Lys Glu Glu Val His Tyr Ala Asp
1               5                   10                  15

Gly Thr Ile Val Lys Arg Glu Asn Ile Glu Tyr Ser Lys Asp Thr Gly
            20                  25                  30

Glu Ile Ala Trp Asn Thr Glu Lys Asp Phe Ala Thr Ile Lys Lys Ile
        35                  40                  45

Leu Ser Tyr Pro Gln Val Asn Ile Val Lys
    50                  55

<210> SEQ ID NO 110
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_sanguinis

<400> SEQUENCE: 110

Tyr Ser Asn Leu Leu Asn Phe Phe Lys Glu Lys Val Arg Tyr Ala Asp
1               5                   10                  15

Gly Thr Ile Lys Lys Arg Glu Asn Ile Glu Tyr Ser Asn Asp Thr Gly
            20                  25                  30

Glu Ile Ala Trp Asn Lys Glu Lys Asp Phe Ala Thr Ile Lys Lys Val

```
        35                  40                  45

Leu Ser Leu Pro Gln Val Asn Ile Val Lys
    50                  55


<210> SEQ ID NO 111
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_gordonii

<400> SEQUENCE: 111

Tyr Ser Asn Leu Leu Asn Phe Phe Lys Glu Glu Val His Tyr Ala Asp
1               5                   10                  15

Gly Thr Ile Val Lys Arg Glu Asn Ile Glu Tyr Ser Lys Asp Thr Gly
            20                  25                  30

Glu Ile Ala Trp Asn Lys Glu Lys Asp Phe Ala Ile Ile Lys Lys Val
        35                  40                  45

Leu Ser Leu Pro Gln Val Asn Ile Val Lys
    50                  55


<210> SEQ ID NO 112
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_cristatus

<400> SEQUENCE: 112

Tyr Ser Asn Leu Leu Asn Phe Phe Lys Glu Glu Val His Tyr Ala Asp
1               5                   10                  15

Gly Thr Ile Val Lys Arg Glu Asn Ile Glu Tyr Ser Lys Asp Thr Gly
            20                  25                  30

Glu Ile Ala Trp Asn Lys Glu Lys Asp Phe Ala Thr Ile Lys Lys Val
        35                  40                  45

Leu Ala Tyr Pro Gln Val Asn Ile Val Lys
    50                  55


<210> SEQ ID NO 113
<211> LENGTH: 59
<212> TYPE: PRT
<213> ORGANISM: Artificial Sequence
<220> FEATURE:
<223> OTHER INFORMATION: non-conservative regions of SpCas 9 of
      Streptococcus_uberis

<400> SEQUENCE: 113

Tyr Ser Asn Leu Met Asn Phe Phe Lys Lys Glu Val Arg Leu Ser Asp
1               5                   10                  15

Gly Thr Val Ile Thr Arg Pro Gln Ile Glu Thr Ser Ser Asp Asp Thr
            20                  25                  30

Gly Glu Ile Val Trp Asp Lys Val Lys Asp Ile Lys Thr Ile Arg Lys
        35                  40                  45

Val Leu Ser Met Pro Gln Ile Asn Val Val Lys
    50                  55


<210> SEQ ID NO 114
<211> LENGTH: 58
<212> TYPE: PRT
<213> ORGANISM: Artificial Sequence
```

<220> FEATURE:
<223> OTHER INFORMATION: non-conservative regions of SpCas 9 of Streptococcus_iniae

<400> SEQUENCE: 114

```
Tyr Ser Asn Leu Met Asn Phe Phe Lys Lys Glu Ile Lys Leu Ala Asp
1               5                   10                  15

Asp Thr Ile Phe Thr Arg Pro Gln Ile Glu Val Asn Thr Glu Thr Gly
            20                  25                  30

Glu Ile Val Trp Asp Lys Val Lys Asp Met Gln Thr Ile Arg Lys Val
        35                  40                  45

Met Ser Tyr Pro Gln Val Asn Ile Val Met
    50                  55
```

<210> SEQ ID NO 115
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_phocae

<400> SEQUENCE: 115

```
Tyr Ser Asn Leu Met Asn Phe Phe Lys Ser Glu Val Lys Leu Ala Asn
1               5                   10                  15

Gly Asn Ile Ile Lys Arg Ser Pro Ile Glu Val Asn Glu Glu Thr Gly
            20                  25                  30

Glu Ile Val Trp Asp Lys Thr Lys Asp Phe Gly Thr Val Arg Lys Val
        35                  40                  45

Leu Ser Ala Pro Gln Val Asn Ile Val Lys
    50                  55
```

<210> SEQ ID NO 116
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_canis

<400> SEQUENCE: 116

```
Tyr Ser Asn Ile Met Asn Phe Phe Lys Thr Glu Val Lys Leu Ala Asn
1               5                   10                  15

Gly Glu Ile Arg Lys Arg Pro Leu Ile Glu Thr Asn Gly Glu Thr Gly
            20                  25                  30

Glu Val Val Trp Asn Lys Glu Lys Asp Phe Ala Thr Val Arg Lys Val
        35                  40                  45

Leu Ala Met Pro Gln Val Asn Ile Val Lys
    50                  55
```

<210> SEQ ID NO 117
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_dysalactiae

<400> SEQUENCE: 117

```
Tyr Ser Asn Ile Met Asn Phe Phe Lys Thr Glu Ile Thr Leu Ala Asn
1               5                   10                  15

Gly Glu Ile Arg Lys Arg Pro Leu Ile Glu Thr Asn Glu Glu Thr Gly
```

```
            20                  25                  30

Glu Ile Val Trp Asp Lys Gly Arg Asp Phe Ala Thr Val Arg Lys Val
        35                  40                  45

Leu Ser Met Pro Gln Val Asn Ile Val Lys
    50                  55


<210> SEQ ID NO 118
<211> LENGTH: 58
<212> TYPE: PRT
<213> ORGANISM: Artificial Sequence
<220> FEATURE:
<223> OTHER INFORMATION: non-conservative regions of SpCas 9 of 4008

<400> SEQUENCE: 118

Tyr Ser Asn Ile Met Asn Phe Phe Lys Thr Glu Ile Thr Leu Ala Asn
1               5                   10                  15

Gly Glu Ile Arg Lys Arg Pro Leu Ile Glu Thr Asn Gly Glu Thr Gly
            20                  25                  30

Glu Ile Val Trp Asp Lys Gly Arg Asp Phe Ala Thr Val Arg Lys Val
        35                  40                  45

Leu Ser Met Pro Gln Val Asn Ile Val Lys
    50                  55


<210> SEQ ID NO 119
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_pyogenes

<400> SEQUENCE: 119

Tyr Ser Asn Ile Met Asn Phe Phe Lys Thr Glu Ile Thr Leu Ala Asn
1               5                   10                  15

Gly Glu Ile Arg Lys Arg Pro Leu Ile Glu Thr Asn Gly Glu Thr Gly
            20                  25                  30

Glu Ile Val Trp Asp Lys Gly Arg Asp Phe Ala Thr Val Arg Lys Val
        35                  40                  45

Leu Ser Met Pro Gln Val Asn Ile Val Lys
    50                  55


<210> SEQ ID NO 120
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_thermophilus

<400> SEQUENCE: 120

Tyr Ser Asn Ile Met Asn Ile Phe Lys Lys Ser Ile Ser Leu Ala Asp
1               5                   10                  15

Gly Arg Val Ile Glu Arg Pro Leu Ile Glu Val Asn Glu Glu Thr Gly
            20                  25                  30

Glu Ser Val Trp Asn Lys Glu Ser Asp Leu Ala Thr Val Arg Arg Val
        35                  40                  45

Leu Ser Tyr Pro Gln Val Asn Val Val Lys
    50                  55


<210> SEQ ID NO 121
<211> LENGTH: 58
```

```
<212> TYPE: PRT
<213> ORGANISM: Artificial Sequence
<220> FEATURE:
<223> OTHER INFORMATION: non-conservative regions of SpCas 9 of
      Streptococcus_salivarius

<400> SEQUENCE: 121

Tyr Ser Asn Ile Met Asn Ile Phe Lys Lys Phe Ile Ser Leu Ala Asp
1               5                   10                  15

Gly Thr Val Ile Glu Arg Pro Leu Ile Glu Val Asn Glu Glu Thr Gly
            20                  25                  30

Glu Ser Val Trp Asn Lys Val Ala Asp Leu Asn Thr Val Arg Lys Val
        35                  40                  45

Leu Ser Tyr Ser Gln Val Asn Ile Val Lys
    50                  55


<210> SEQ ID NO 122
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_mutans

<400> SEQUENCE: 122

Tyr Ser Asn Ile Met Asn Met Phe Lys Ser Lys Val Lys Leu Ala Asp
1               5                   10                  15

Asp Gln Ile Val Glu Arg Pro Met Ile Glu Val Asn Asp Glu Thr Gly
            20                  25                  30

Glu Ile Ala Trp Asp Lys Thr Lys His Ile Thr Thr Val Lys Lys Val
        35                  40                  45

Leu Ser Tyr Pro Gln Val Asn Ile Val Lys
    50                  55


<210> SEQ ID NO 123
<211> LENGTH: 59
<212> TYPE: PRT
<213> ORGANISM: Artificial Sequence
<220> FEATURE:
<223> OTHER INFORMATION: non-conservative regions of SpCas 9 of
      Streptococcus_suis

<400> SEQUENCE: 123

Tyr Ser Asn Ile Met Asn Phe Phe Lys Arg Val Val Lys Ser Ser Lys
1               5                   10                  15

Thr Gly Thr Val Lys Ile Arg Pro Ile Ile Glu Val Asn Lys Glu Thr
            20                  25                  30

Gly Glu Ile Val Trp Asp Lys Lys Ser Asp Phe Arg Thr Val Arg Lys
        35                  40                  45

Val Leu Ser Tyr Pro Gln Val Asn Val Val Lys
    50                  55


<210> SEQ ID NO 124
<211> LENGTH: 58
<212> TYPE: PRT
<213> ORGANISM: Artificial Sequence
<220> FEATURE:
<223> OTHER INFORMATION: non-conservative regions of SpCas 9 of
      Streptococcus_repiraculi

<400> SEQUENCE: 124

Tyr Ser Asn Leu Leu Asn Phe Phe Lys Thr Lys Ile Lys Leu Ala Asp
1               5                   10                  15
```

```
Gly Ser Glu Ile Lys Gln Ala Thr Val Glu Val Tyr Ser Glu Thr Gly
            20                  25                  30

Glu Ile Ile Trp Asn Lys Lys Lys Asp Phe Ala Thr Ile Arg Lys Val
        35                  40                  45

Leu Ala Tyr Pro Gln Val Asn Val Val Lys
    50                  55


<210> SEQ ID NO 125
<211> LENGTH: 45
<212> TYPE: PRT
<213> ORGANISM: Artificial Sequence
<220> FEATURE:
<223> OTHER INFORMATION: non-conservative regions of SpCas 9 of
      Streptococcus_intermedius

<400> SEQUENCE: 125

Tyr Ser Asn Ile Met Asn Phe Phe Lys Lys Asp Asp Val Arg Thr Asp
1               5                   10                  15

Lys Asn Gly Glu Ile Ile Trp Lys Lys Asp Glu His Ile Ser Asn Ile
            20                  25                  30

Lys Lys Val Leu Ser Tyr Pro Gln Val Asn Ile Val Lys
        35                  40                  45


<210> SEQ ID NO 126
<211> LENGTH: 45
<212> TYPE: PRT
<213> ORGANISM: Artificial Sequence
<220> FEATURE:
<223> OTHER INFORMATION: non-conservative regions of SpCas 9 of
      Streptococcus_orisasini

<400> SEQUENCE: 126

Tyr Ser Asn Ile Met Asn Phe Phe Lys Lys Asp Asp Val Arg Thr Asp
1               5                   10                  15

Glu Asn Gly Glu Ile Ile Trp Lys Lys Asp Glu His Ile Ser Asn Ile
            20                  25                  30

Lys Lys Val Leu Ser Tyr Pro Gln Val Asn Ile Val Lys
        35                  40                  45


<210> SEQ ID NO 127
<211> LENGTH: 57
<212> TYPE: PRT
<213> ORGANISM: Artificial Sequence
<220> FEATURE:
<223> OTHER INFORMATION: non-conservative regions of SpCas 9 of
      Streptococcus_anginosus

<400> SEQUENCE: 127

Tyr Ser Asn Leu Met Asn Phe Phe Lys Lys Glu Val Lys Phe Ala Asp
1               5                   10                  15

Gly Thr Val Val Glu Arg Pro Asp Ile Glu Thr Ser Glu Asp Gly Glu
            20                  25                  30

Ile Ala Trp Asn Lys Gln Thr Asp Phe Lys Ile Val Arg Lys Val Leu
        35                  40                  45

Ser Tyr Pro Gln Val Asn Ile Val Lys
    50                  55


<210> SEQ ID NO 128
<211> LENGTH: 57
<212> TYPE: PRT
<213> ORGANISM: Artificial Sequence
<220> FEATURE:
```

```
<223> OTHER INFORMATION: non-conservative regions of SpCas 9 of
      Streptococcus_milleri

<400> SEQUENCE: 128

Tyr Ser Asn Leu Met Asn Phe Phe Lys Lys Glu Val Lys Phe Ala Asp
1               5                   10                  15

Gly Thr Val Val Glu Arg Pro Asp Ile Glu Thr Ser Glu Asp Gly Glu
            20                  25                  30

Ile Ala Trp Asn Lys Gln Thr Asp Phe Lys Ile Val Arg Lys Val Leu
        35                  40                  45

Ser Tyr Pro Gln Val Asn Ile Val Lys
    50                  55


<210> SEQ ID NO 129
<211> LENGTH: 45
<212> TYPE: PRT
<213> ORGANISM: Artificial Sequence
<220> FEATURE:
<223> OTHER INFORMATION: non-conservative regions of SpCas 9 of
      Streptococcus_viridans

<400> SEQUENCE: 129

Tyr Ser Asn Ile Leu Arg Phe Phe Lys Lys Glu Asp Ile Gln Thr Asn
1               5                   10                  15

Glu Asp Gly Glu Ile Ala Trp Asn Lys Glu Lys His Ile Lys Ile Leu
            20                  25                  30

Arg Lys Val Leu Ser Tyr Pro Gln Val Asn Ile Val Lys
        35                  40                  45


<210> SEQ ID NO 130
<211> LENGTH: 57
<212> TYPE: PRT
<213> ORGANISM: Artificial Sequence
<220> FEATURE:
<223> OTHER INFORMATION: non-conservative regions of SpCas 9 of
      Streptococcus_lutetiensis

<400> SEQUENCE: 130

Tyr Ser Asn Leu Met Asn Phe Phe Lys Thr Glu Val Lys Tyr Ala Asp
1               5                   10                  15

Gly Arg Val Phe Glu Arg Pro Asp Ile Glu Thr Asn Ala Asp Gly Glu
            20                  25                  30

Val Val Trp Asn Lys Gln Lys Asp Phe Glu Ile Ile Arg Lys Val Leu
        35                  40                  45

Ser Tyr Pro Gln Val Asn Ile Val Lys
    50                  55


<210> SEQ ID NO 131
<211> LENGTH: 57
<212> TYPE: PRT
<213> ORGANISM: Artificial Sequence
<220> FEATURE:
<223> OTHER INFORMATION: non-conservative regions of SpCas 9 of
      Streptococcus_macedonicus

<400> SEQUENCE: 131

Tyr Ser Asn Leu Met Asn Phe Phe Lys Thr Glu Val Lys Tyr Ala Asp
1               5                   10                  15

Gly Arg Val Phe Glu Arg Pro Asp Ile Glu Thr Asn Ala Asp Gly Glu
            20                  25                  30

Val Val Trp Asn Lys Gln Lys Asp Phe Asp Ile Val Arg Lys Val Leu
        35                  40                  45
```

-continued

Ser Tyr Pro Gln Val Asn Ile Val Lys
50 55

<210> SEQ ID NO 132
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_pantholopis

<400> SEQUENCE: 132

Tyr Ser Asn Leu Met Asn Phe Phe Lys Arg Val Val Arg Tyr Ser Asn
1 5 10 15

Gly Arg Val Ile Val Arg Pro Val Ile Glu Tyr Ser Lys Asp Thr Gly
20 25 30

Glu Ile Val Trp Asn Lys Glu Thr Asp Phe Arg Thr Ile Cys Lys Val
35 40 45

Leu Ser Tyr Pro Gln Val Asn Ile Val Lys
50 55

<210> SEQ ID NO 133
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_gallolyticus

<400> SEQUENCE: 133

Tyr Ser Asn Leu Met Asn Phe Phe Lys Arg Val Ile Arg Tyr Ser Asn
1 5 10 15

Gly Lys Val Val Val Arg Pro Val Ile Glu Cys Ser Lys Asp Thr Gly
20 25 30

Glu Ile Ala Trp Asn Lys Gln Thr Asp Phe Glu Lys Val Arg Arg Val
35 40 45

Leu Ser Tyr Pro Gln Val Asn Ile Val Lys
50 55

<210> SEQ ID NO 134
<211> LENGTH: 58
<212> TYPE: PRT
<213> ORGANISM: Artificial Sequence
<220> FEATURE:
<223> OTHER INFORMATION: non-conservative regions of SpCas 9 of Streptococcus_equinus

<400> SEQUENCE: 134

Tyr Ser Asn Leu Met Asn Phe Phe Lys Arg Ile Ile Arg Tyr Ser Asn
1 5 10 15

Gly Lys Val Val Val Arg Pro Val Ile Glu Cys Ser Lys Asp Thr Gly
20 25 30

Glu Ile Ala Trp Asn Lys Gln Thr Asp Phe Glu Lys Val Arg Met Val
35 40 45

Leu Ser Tyr Pro Gln Val Asn Ile Val Lys
50 55